(12) United States Patent
Tang

(10) Patent No.: US 11,413,329 B2
(45) Date of Patent: Aug. 16, 2022

(54) CANCER CELL TRAP

(71) Applicant: BOARD OF REGENTS, THE UNIVERSITY OF TEXAS SYSTEM, Austin, TX (US)

(72) Inventor: Liping Tang, Arlington, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 14/436,601

(22) PCT Filed: Oct. 19, 2013

(86) PCT No.: PCT/US2013/065803
§ 371 (c)(1),
(2) Date: Apr. 17, 2015

(87) PCT Pub. No.: WO2014/063128
PCT Pub. Date: Apr. 24, 2014

(65) Prior Publication Data
US 2015/0283073 A1    Oct. 8, 2015

Related U.S. Application Data

(60) Provisional application No. 61/716,526, filed on Oct. 20, 2012.

(51) Int. Cl.
| | | |
|---|---|---|
| *A61K 9/06* | (2006.01) |
| *A61K 47/32* | (2006.01) |
| *A61L 31/04* | (2006.01) |
| *A61L 31/12* | (2006.01) |
| *A61L 31/16* | (2006.01) |
| *A61K 9/50* | (2006.01) |
| *A61L 31/14* | (2006.01) |
| *A61K 38/18* | (2006.01) |
| *A61K 38/19* | (2006.01) |
| *A61K 38/20* | (2006.01) |
| *A61K 38/28* | (2006.01) |
| *A61K 38/30* | (2006.01) |
| *A61K 38/38* | (2006.01) |
| *A61K 45/06* | (2006.01) |
| *A61K 47/10* | (2017.01) |
| *A61K 47/34* | (2017.01) |
| *G01N 33/50* | (2006.01) |

(52) U.S. Cl.
CPC ........ *A61K 38/1816* (2013.01); *A61K 9/5036* (2013.01); *A61K 38/195* (2013.01); *A61K 38/28* (2013.01); *A61K 38/30* (2013.01); *A61K 38/385* (2013.01); *A61K 45/06* (2013.01); *A61K 47/10* (2013.01); *A61K 47/34* (2013.01); *A61L 31/041* (2013.01); *A61L 31/129* (2013.01); *A61L 31/145* (2013.01); *A61L 31/16* (2013.01); *G01N 33/5091* (2013.01); *A61K 9/06* (2013.01); *A61K 38/18* (2013.01); *A61K 38/1833* (2013.01); *A61K 38/1866* (2013.01); *A61K 38/2053* (2013.01); *A61K 47/32* (2013.01); *A61L 2300/414* (2013.01); *A61L 2300/416* (2013.01); *A61L 2300/426* (2013.01); *G01N 2800/7028* (2013.01)

(58) Field of Classification Search
CPC ........................ A61L 2300/62; A61K 38/1816
See application file for complete search history.

(56) References Cited

U.S. PATENT DOCUMENTS

| 5,595,756 A * | 1/1997 | Bally .................. A61K 9/1272 264/4.1 |
| 2010/0159008 A1 * | 6/2010 | Barron .................... C12P 21/00 424/484 |

FOREIGN PATENT DOCUMENTS

| JP | 2006131577 A | 5/2006 |
| JP | 2008523061 A | 7/2008 |
| JP | 2008274267 A | 11/2008 |
| WO | 2009/002401 | 12/2008 |
| WO | WO 2009002401 A2 * | 12/2008 ............. A61L 27/50 |
| WO | 2011/090778 | 7/2011 |

OTHER PUBLICATIONS

Ko, 2010. Novel animal model and in vivo imaging system to study inflammatory response-mediated cancer metastasis (Order No. 3408934). Available from ProQuest Dissertations & Theses Global. (609525310). Retrieved from http://search.proquest.com/docview/609525310?accountid=14753.*
Ko (2010. Novel animal model and in vivo imaging system to study inflammatory response-mediated cancer metastasis (Order No. 3408934). Available from ProQuest Dissertations & Theses Global. (609525310). Retrieved from http://search.proauest.com/docview/609525310?accountid=14753).*
Cocconi et al. Treatment of metastatic malignant melanoma with dacrazine plus tamoxifen. New England Journal of Medicine, 1992; 327:516-523.*
Heppner et al. Tumor heterogeneity:biological implications and therapeutic consequences. Cancer Metastasis Review 2:5-23; 1983.*
Jain RK. Barriers to drug delivery in solid tumors. Scientific American, Jul. 1994, 58-65.*
Lollini et al. Vaccines for tumor prevention. Nature Review Cancer. Mar. 2006;6(3):204-16.*
Bei et al. Engineering nanomedicines for improved melanoma therapy: progress and promises. Nanomedicine, 2010, 5(9): 1385-1399 (Year: 2010).*

(Continued)

*Primary Examiner* — Vanessa L. Ford
*Assistant Examiner* — Sandra Dillahunt
(74) *Attorney, Agent, or Firm* — Nevrivy Patent Law Group P.L.L.C.

(57) ABSTRACT

The present invention is directed to cancer cell traps and methods of using cancer cell traps to treat and detect metastatic cancer in subjects. The cancer cell traps are administered to subjects and induce the migration and accumulation of metastatic cancer cells in the cancer cell traps.

7 Claims, 41 Drawing Sheets

(56) References Cited

OTHER PUBLICATIONS

Ko 2010. Novel animal model and in vivo imaging system to study inflammatory response-mediated cancer metastasis Available from ProQuest Dissertaions & Theses Global. (Year: 2010).*

Cocconi et al. Treatment of metastatic malignant melanoma with dacarbazine plus tamoxifen. New England Journal of Medicine, 1992; 327:516-523 (Year: 1992).*

Tran et al. Use of liposomes as drug delivery vehicles for treatment of melanoma. Pigment Cell Melanoma Res. 2009; 22:388-399 (Year: 2009).*

Ko (2010. Novel animal model and in vivo imaging system to study inflammatory response-mediated cancer metastasis (Order No. 3408934). Available from ProQuest Dissertations & Theses Global. (609525310). Retrieved from http://search.proauest.com/docview/609525310?accountid=14753) (Year: 2010).*

Cocconi et al. New England Journal of Medicine, 1992; 327:516-523 (Year: 1992).*

Tran et al. Pigment Cell Melanoma Res. 2009; 22:388-399). (Year: 2009).*

International Search Report for PCT/US2013/065803 dated Feb. 6, 2014.

Raja et al., A new diagnostic for cancer dynamics: Status and initial tests of the NANIVID, Proc. of SPIE, 7207: 72070E-1-8 (2009).

European Search Report from Appl. No. 13846518.2, dated Feb. 10, 2017.

Japanese Office Action from Appl. No. 2015-38095, dated Jul. 11, 2017.

English language translation of Japanese Office Action from Appl. No. 2015-38095, dated Jul. 11, 2017.

Chinese Office Action from Appl. No. 201380067121.1, dated Aug. 5, 2017.

English language translation of Chinese Office Action from Appl. No. 201380067121.1, dated Aug. 5, 2017.

Office Action from Japanese Appl. No. 2015-38095, dated Apr. 24, 2018.

English language translation of Office Action from Japanese Appl. No. 2015-38095, dated Apr. 24, 2018.

* cited by examiner

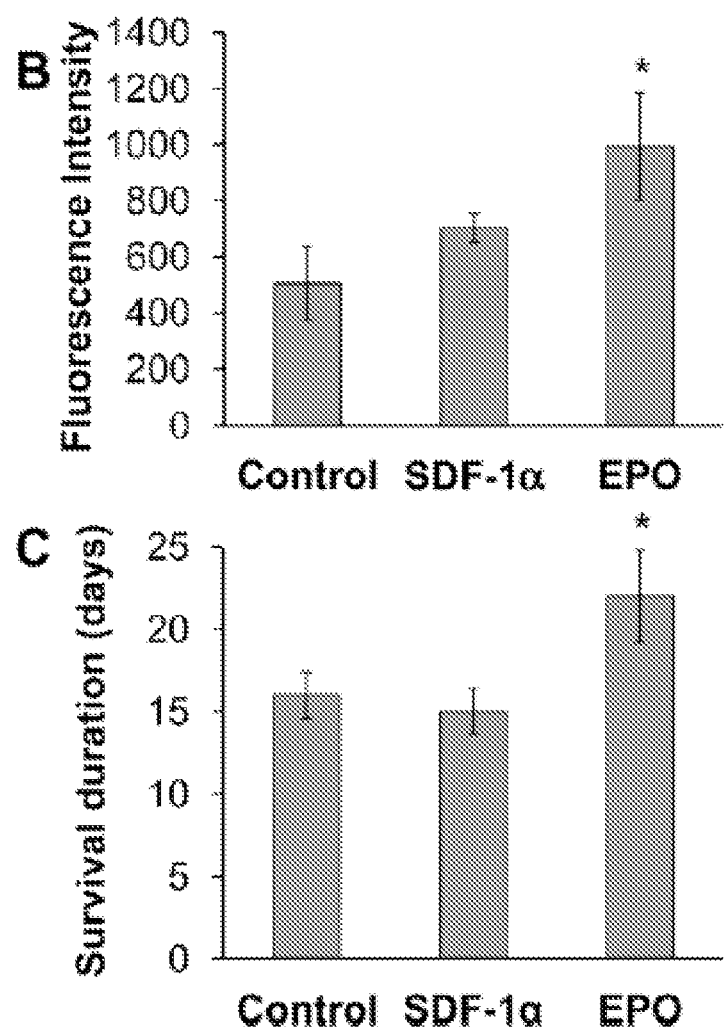
FIG. 7B-C

FIG. 10A-C
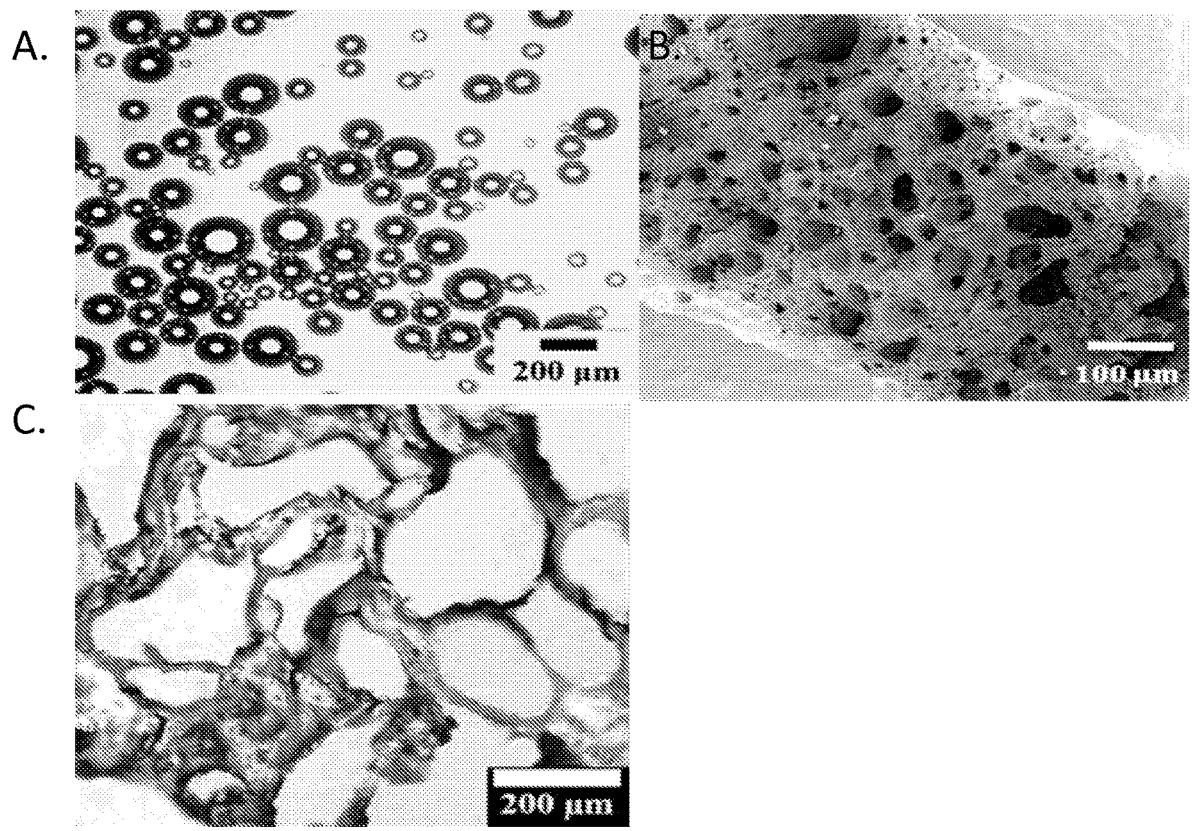

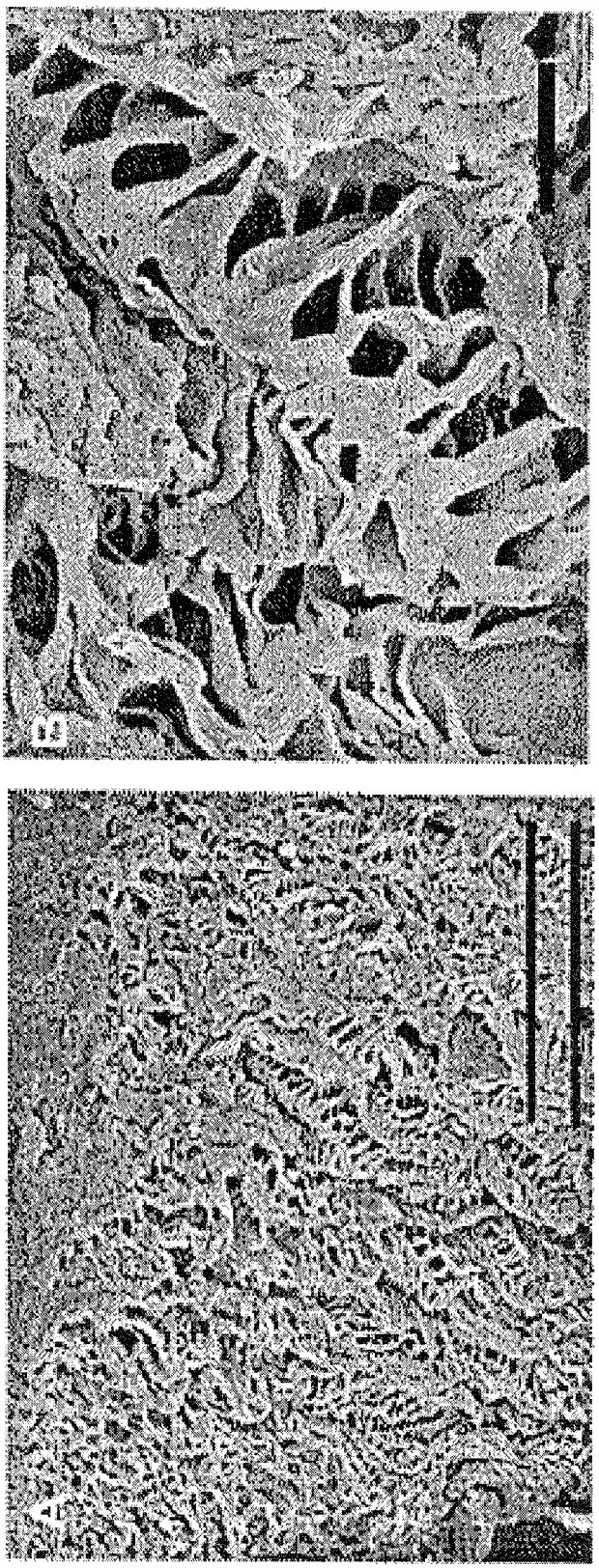
FIG. 12A-B

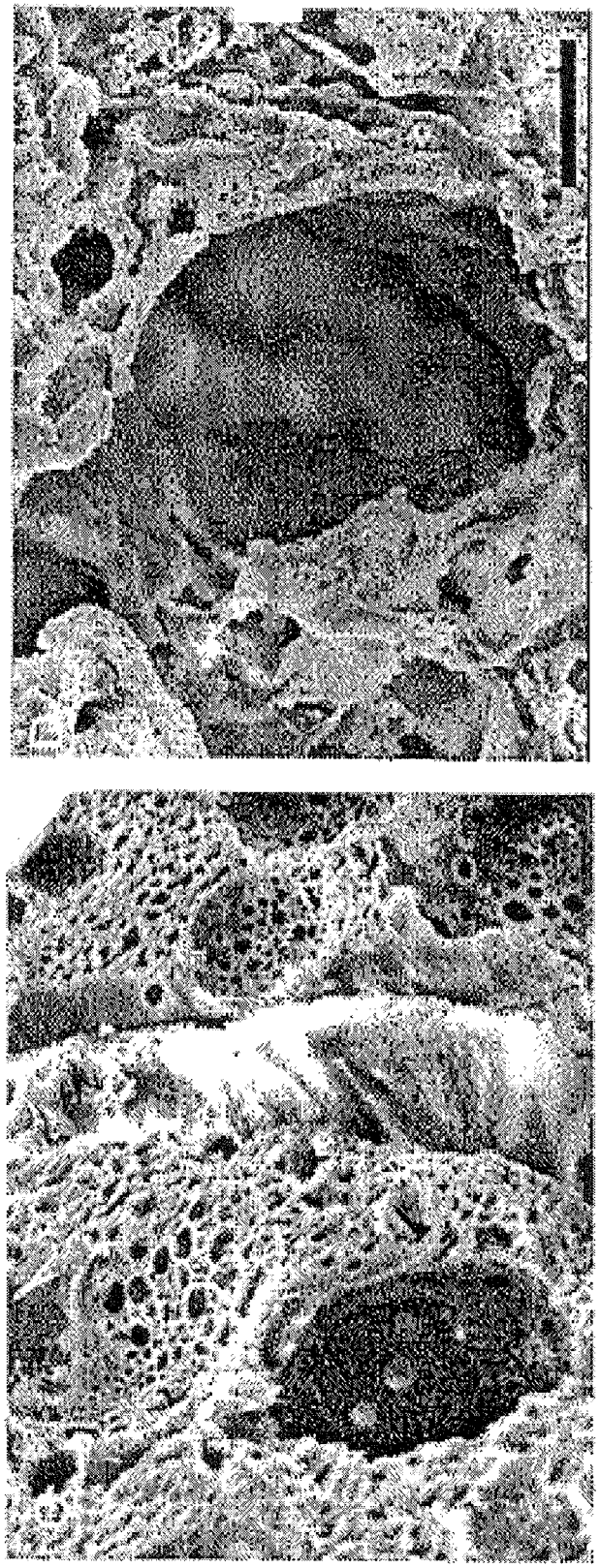
FIG. 12C-D

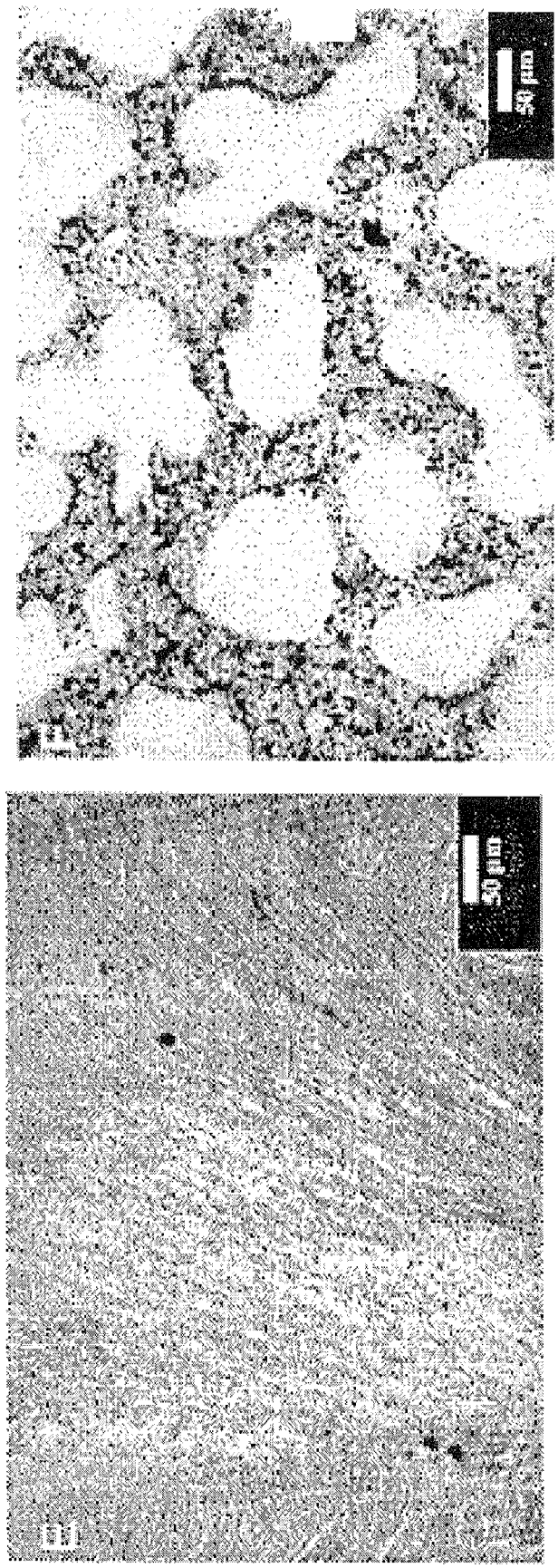
FIG. 12E-F

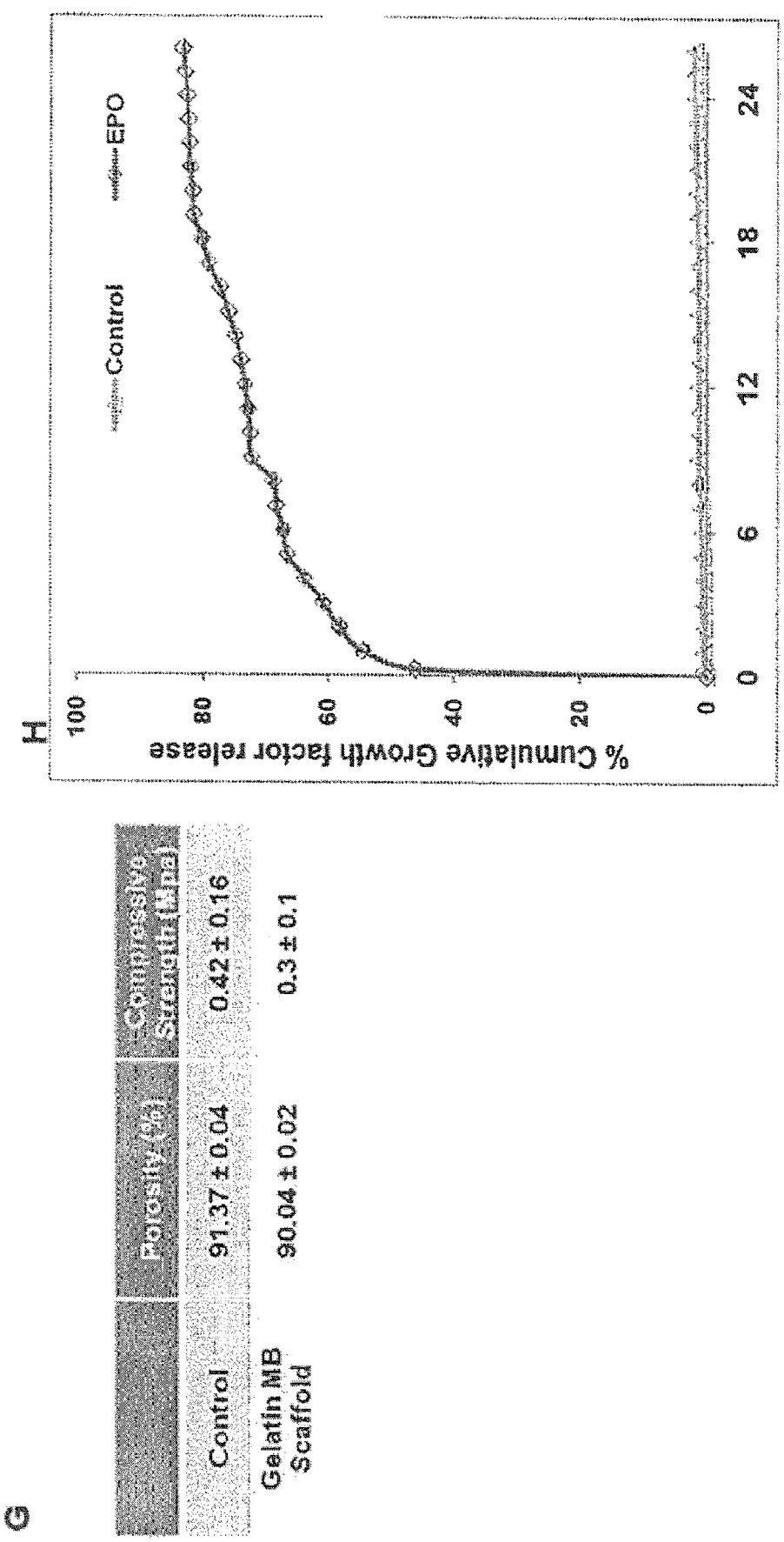
FIG. 12G-H

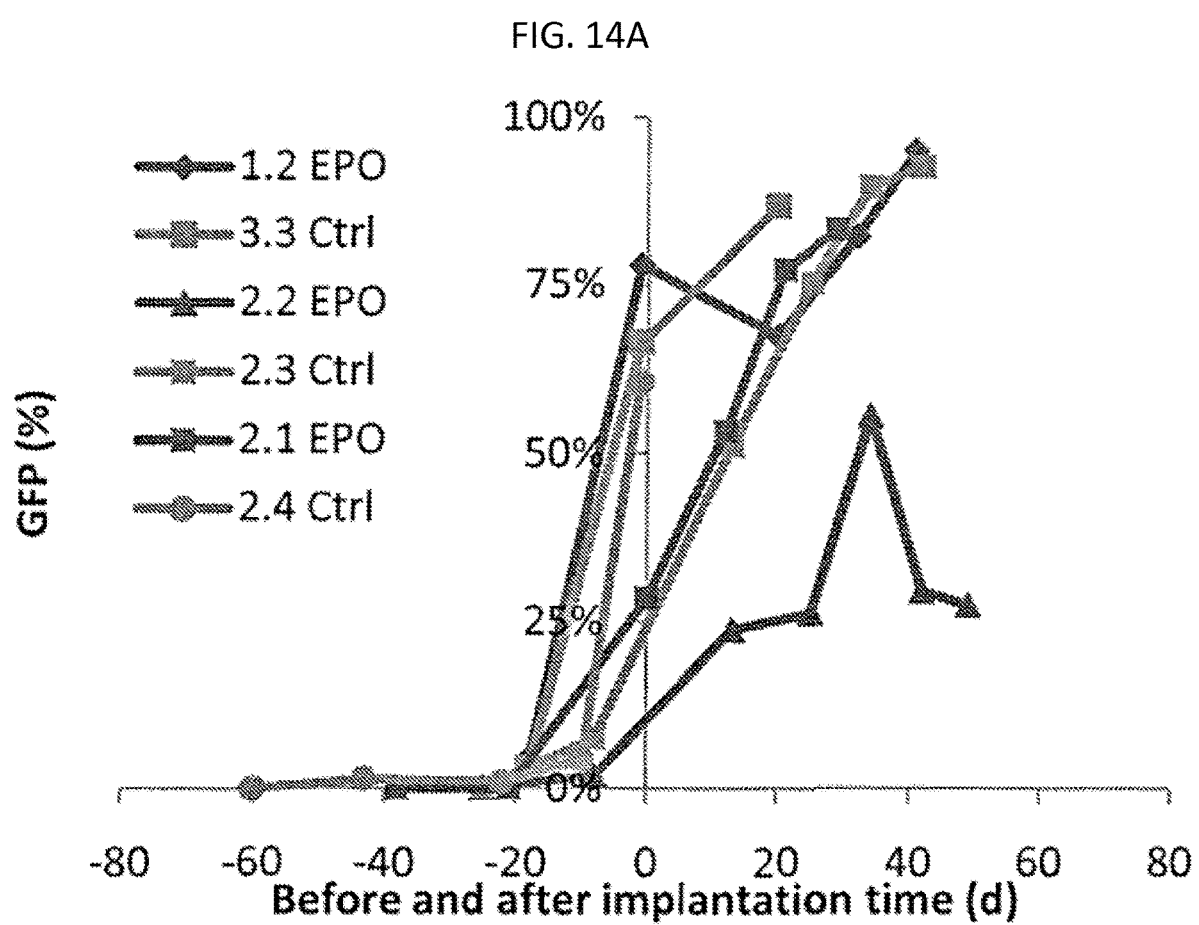

FIG. 15
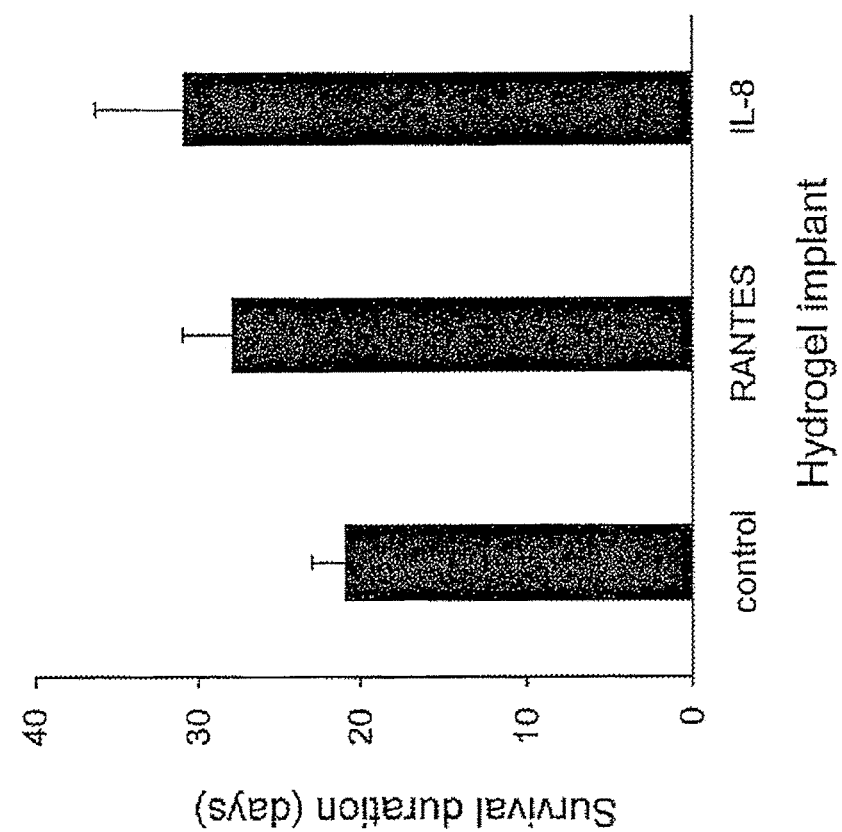
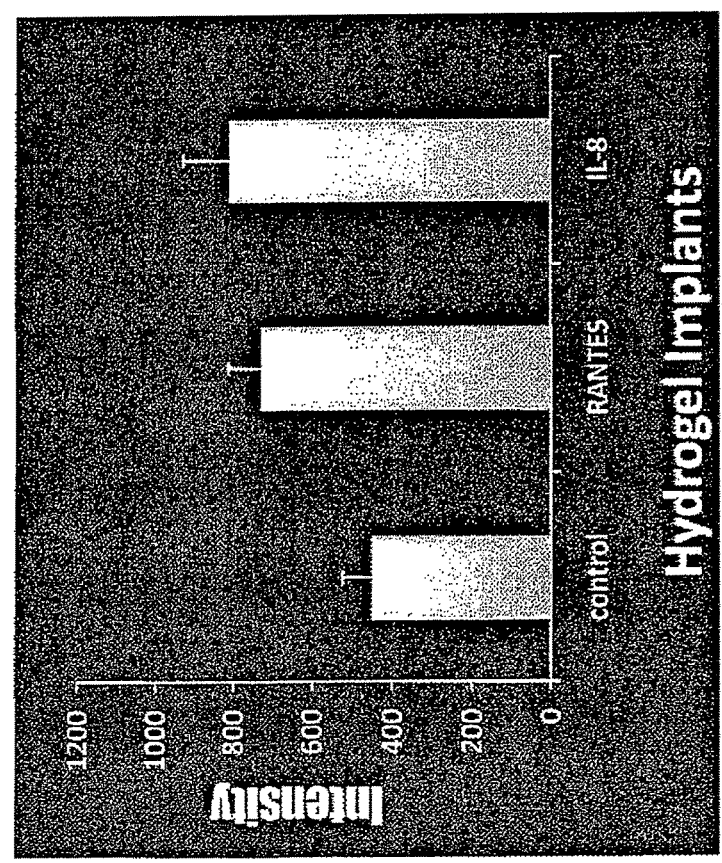

FIG. 16
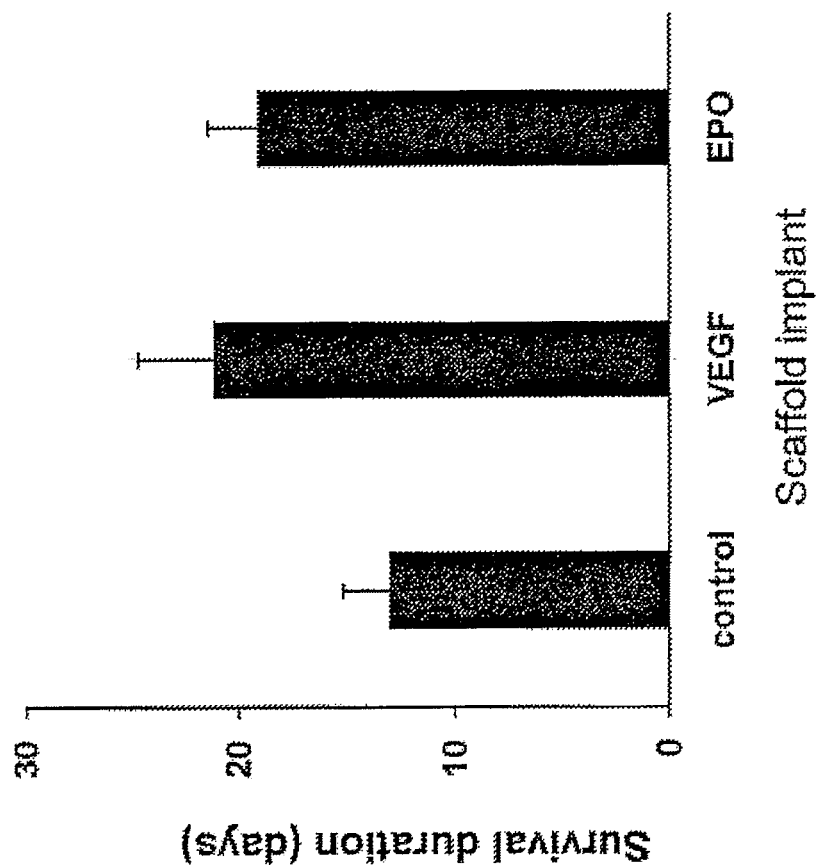
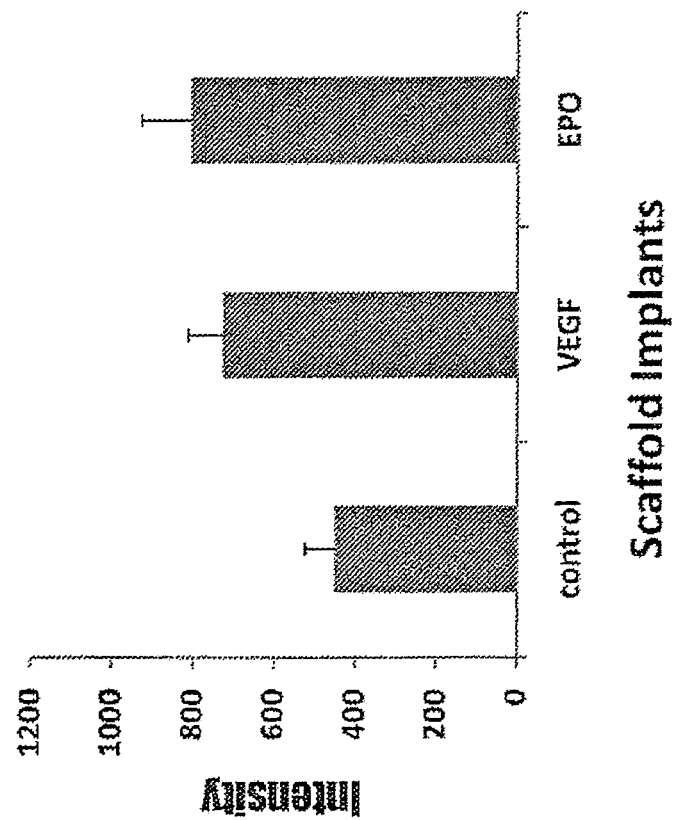

FIG. 18A-B

CANCER CELL TRAP

CROSS-REFERENCE TO RELATED APPLICATIONS

This application claims the benefit of U.S. Provisional Appl. No. 61/716,526 filed on Oct. 20, 2012, the contents of which are hereby incorporated by reference in their entirety.

STATEMENT OF FEDERALLY SPONSORED RESEARCH AND DEVELOPMENT

This invention was made with government support under Grant No. RO1, EB007271-01 awarded by The National Institutes of Health. The government has certain rights in the invention.

FIELD OF THE INVENTION

The field of the invention relates generally to the field of cancer. The field of the invention also relates to cancer cell traps and the use thereof for treating and/or preventing cancer metastasis, and for diagnosis and detection of cancer metastasis.

BACKGROUND OF THE INVENTION

Metastasis or metastatic disease is the spread of a disease from one organ or part to another non-adjacent organ or part. Metastatic disease is primarily but not uniquely associated with malignant tumor cells and infections (Klein, 2008, Science 321(5897):1785-88; Chiang & Massague, 2008, New Engl. J. Med. 359(26):2814-23). Metastatic tumors are very common in the late stages of cancer. For example, the high lethality of melanoma is caused by melanoma cells' ability to metastasize to almost any part of the body. It should be noted that cancer metastasis to different organs is a common complication of many cancers and is responsible for 90% of human cancer deaths. Currently, patients with stage III and IV metastatic melanoma are often treated with surgical resection, radiation, chemotherapy, biochemotherapy, or combinations thereof. Unfortunately, these treatments, often associated with profound systemic side-effects, do not substantially improve outcome.

The most common places for the metastases to occur are the lungs, liver, brain, and the bones. There is also a propensity for certain tumors to seed in particular organs. For example, prostate cancer usually metastasizes to the bones. In a similar manner, colon cancer has a tendency to metastasize to the liver. Stomach cancer often metastasizes to the ovary in women. Breast tumor cells often metastasize to bone tissue. Studies have suggested that these tissue-selective metastasis processes are due to specific anatomic and mechanical routes.

Cancer metastasis can be divided into a series of steps and pathways including invasion through extracellular matrix, intravasation into lymphatic or blood vessels, survival in circulation, extravasation to a distant site, and progressive growth at that site. See e.g., Chambers, A. F., A. C. Groom, and L C. MacDonald, *Nat Rev Cancer,* 2002. 2(8): p. 563-72; Fidler, I. J., *Nat Rev Cancer,* 2003. 3(6): p. 453-8; and Folkman, J., *Semin Cancer Biol,* 1992. 3(2): p. 65-71.

Despite intensive research efforts, detailed mechanisms of cancer metastasis are not entirely understood. The lack of an animal model, which can be used to quantify the extent of cancer metastasis in a controllable manner is, at least partially, responsible for this deficiency. Several in vitro and in vivo models have been used in the past to assess cancer metastasis. Most studies of metastasis have been carried out on rodents with tumor xenografts. See e.g., Welch D R. *Clin Exp Metastasis* 1997; 15:272-306; Gupta G P, Perk J, Acharyya S, de Candia P, Mittal V, Todorova-Manova K, et al., *Proc Natl Acad Sci USA* 2007; 104:19506-19511; and Yamamoto M, Kikuchi H, Ohta M, Kawabata T, Hiramatsu Y, Kondo K, et al. *Cancer Res* 2008; 68:9754-9762.

In assays of spontaneous metastasis, tumor cells are injected into a site, preferably an orthotopic location. The primary tumor forms and metastases develop which are then monitored through time. Although this assay measures the complete metastatic process, this method is usually qualitative and time consuming. See e.g., Cespedes M V, Casanova I, Parreno M, Mangues R. *Clin Transl Oncol* 2006; 8:318-329; and Talmadge J E, Singh R K, Fidler I J, Raz A. *Am J Pathol* 2007; 170:793-804.

Metastasis evaluation has also been carried out by quantifying tumor growth in vital organs following by injection of tumor cells into the bloodstream. This method can only provide information about the post-intravasation stage of metastasis. It should also be noted that several transgenic mouse strains have been used to study primary tumorigenesis and spontaneous metastases. See e.g., Talmadge J E, Singh R K, Fidler I J, Raz A. *Am J Pathol* 2007; 170:793-804; Khanna C, Hunter K. *Carcinogenesis* 2005; 26:513-523; Schwertfeger K L, Xian W, Kaplan A M, Burnett S H, Cohen D A, Rosen J M. *Cancer Res* 2006; 66:5676-5685; and Taketo M M, Edelmann W. *Gastroenterology* 2009; 136:780-798. A significant disadvantage of these systems however is the expense, unpredictability, and lack of versatility.

Numerous reports implicate inflammatory signals in the facilitation of metastatic cell escape from the original tumor and spread to new sites. See e.g., Lorusso, G. and C. Ruegg, *Histochem Cell Biol,* 2008. 130(6): p. 1091-103; Lu, H., W. Ouyang, and C. Huang, *Mol Cancer Res,* 2006. 4(4): p. 221-33; Marx, J., *Science,* 2004. 306(5698): p. 966-8; and Pollard, J. W., *Nat Rev Cancer,* 2004. 4(1): p. 71-8.

Furthermore, increasing evidence suggests that inflammatory responses play an important role in tumor development and progression. See e.g., Lorusso, G. and C. Ruegg, *Histochem Cell Biol,* 2008. 130(6): p. 1091-103; Lu, H., W. Ouyang, and C. Huang, *Mol Cancer Res,* 2006. 4(4): p. 221-33; Aggarwal, B. B., et al., *Biochem Phamacol,* 2006. 72(11): p. 1605-21; Arias, J. I., M. A. Aller, and J. Arias, *Mol Cancer,* 2007. 6: p. 29; and Melnikova, V. O. and M. Bar-Eli, *Pigment Cell Melanoma Res,* 2009. 22(3): p. 257-67.

For example, inflammatory chemokines, such as CXCL12 (SDF-1)/CXCR4, CCR7/CCL21, MIP-1 a/CCL3, IL-8/CXCL8 and RANTES/CCL5, have been associated with metastasis of breast cancer, melanoma, myeloma, colorectal carcinoma, ovarian carcinoma and lung cancer. Ben-Baruch, A., *Cancer Metastasis Rev,* 2006. 25(3): p. 357-71; Gomperts, B. N. and R. M. Strieter, *Contrib Microbiol,* 2006. 13:170-90; Kakinuma, T. and S. T. Hwang, *J Leukoc Biol,* 2006. 79(4):639-51; Opdenakker, G. and J. Van Damme, *Int J Dev Biol,* 2004. 48(5-6): p. 519-27; Shields, J. D., et al. *Oncogene,* 2007. 26(21): p. 2997-3005; and Soria, G. and A. Ben-Baruch, *Cancer Lett,* 2008. 267(2): p. 271-85.

Human and murine tumors are also found to secrete various inflammatory cytokines, CXC chemokines and their receptors. Ben-Baruch, A., *Cancer Metastasis Rev,* 2006. 25(3): p. 357-71; Germano, G., P. Allavena, and A. Mantovani, *Cytokine,* 2008. 43(3): p. 374-9; Luboshits, G., et al., *Cancer Res,* 1999. 59(18): p. 4681-7; Mantovani, A., et al.,

*Immunol Today*, 1992. 13(7): p. 265-70; and Negus, R. P., et al., *J Clin Invest*, 1995. 95(5): p. 2391-6.

Inflammatory chemokine receptors such as CXCR4 and CCR7 are commonly expressed in human breast cancer. Muller, A., et al., *Nature*, 2001. 410(6824): p. 50-6. Blocking CCL21 has been shown to reduce the migration of metastatic melanoma cells. Lanati, S., et al., *Cancer Res*, 2010.

These results support the idea that inflammatory chemokines play an important role in triggering the cancer cell migration in vivo. Recent studies have revealed that B16F10 melanoma cells contain 280-fold higher histamine than non-cancerous melanocytes and histamine release may be important in melanoma cell migration and growth. See e.g., Davis, S. C., et al., *Inflamm Res*, 2010; Medina, V. A. and E. S. Rivera, *Br J Pharmacol*, 2010. 161(4): p. 755-67; and Medina, V. A., et al., *Free Radic Biol Med*, 2009. 46(11): p. 1510-5.

In addition, many growth factors, such as erythropoietin (EPO), have been shown to promote the migration and spreading of melanoma cells and other cancer cells. See e.g., Mirmohammadsadegh, A., et al., *J Invest Dermatol*, 2010. 130(1): p. 201-10; and Shi, Z., et al., *Mol Cancer Res*, 2010. 8(4): p. 615-26.

Some recent publications allege that nanospheres can be fabricated to target and then to eradicate tumor cells via localized drug delivery or induced immune reactions. See Hara, K., et al., *Oncol Rep*, 2006. 16(6): p. 1215-20; Ruoslahti, E., S. N. Bhatia, and M. J. Sailor, *J Cell Biol*, 2010. 188(6): p. 759-68; Torchilin, V. P., *Handb Exp Pharmacol*, 2010(197): p. 3-53.

Early detection of metastatic cancer can significantly impact the prognosis of individuals suffering from cancer and determine appropriate course of treatment. In general, when a primary tumor is detected, one or more of the nearby (regional) lymph nodes may be removed and assayed for spread of the cancer to the lymph nodes. Detection of cancer cells in lymph nodes (diagnosis of lymph node metastasis) provides useful information for determining operation range or for determining postoperative chemotherapy. However, even if cancer cells are present in lymph nodes, the cancer cells may be overlooked if a section is prepared from a cancer cell-free cut surface and the section is subjected to tissue diagnosis. In addition, diagnosis results may vary depending on the level of skill of a medical pathologist who makes the diagnosis. Further, cancer cells may not be present in a nearby lymph node even though the cancer cells have metastasized to distant locations or have metastatic potential.

Despite extensive research on the mechanisms of cancer metastasis, there is not an effective approach to suppress or prevent the development of metastasis. There is an urgent need in the art to efficiently suppress, minimize or prevent the development of metastatic tumors in patients. There is also a need in the art for sensitive and robust methods to detect metastatic cancer cells. The present invention fulfills these and other needs.

The foregoing description includes information that may be useful in understanding the present invention. It is not an admission that any of the information provided herein is prior art or relevant to the presently claimed invention, or that any publication specifically or implicitly referenced is prior art.

SUMMARY OF THE INVENTION

In one aspect, the invention provides a cancer cell trap, wherein metastatic cancer cells migrate and accumulate in the cancer cell trap. In some embodiments, the cancer cell trap optionally comprises one or more bioactive agents. In some embodiments, the cancer cell trap comprises one or more chemotherapeutic agents. In some embodiments, the chemotherapeutic agent and/or bioactive agent is released from the cancer cell trap.

In some embodiments, the cancer cell trap is formulated as a pharmaceutical composition, comprising one or more pharmaceutically acceptable excipients.

In some embodiments, the cancer cell trap is capable of releasing one or more bioactive agents such as proteins, chemokines, and growth factors. In some embodiments, the release is controlled release or extended release over a period of time, enabling the recruitment and accumulation of cancer cells in the cancer cell trap over time.

In some embodiments, the cancer cell trap is selected from the group consisting of a scaffold structure, a hydrogel, microparticles and nanoparticles. In some embodiments, the cancer cell trap comprises a microbubble scaffold. In some embodiments, the cancer cell trap is a tissue scaffold. In some embodiments, the scaffold comprises a degradable polymer and polypeptides. In some embodiments, the scaffold is highly porous, enabling the release of bioactive agents and accumulation of cells therein.

In some embodiments, the cancer cell trap comprises an in situ solidified hydrogel. In some embodiments, the cancer cell trap is fabricated from a polyethylene glycol based in situ gelling hydrogel.

In some embodiments, the hydrogel comprises materials selected from the group consisting of one or more polymeric materials, polysaccharides, polyethylene glycol-poly acrylic acid interpenetrating network (PEG-PAA-IPN) hydrogel, polyethylene glycol, extracellular matrix proteins, fibrinogen, hydrogel microparticles and combinations thereof.

In some embodiments, the scaffold comprises poly(lactide-co-glycolide) (PLGA) copolymers, albumin, collagen, gelatin, immunoglobulins, extracellular matrix proteins, fibronectin and combinations thereof.

In some embodiments, the cancer cell trap comprises one or more bioactive proteins or molecules. In some embodiments, the bioactive proteins or molecules are selected from the group consisting of IL-1, IL-4, IL-8, IL-10, IL-13, IL-17, CCL2, CCL5, CCL9, CCL18, CCL19, CCL20, CCL21, CCL25, CCL27, CCR4, CCR5, CCR7/CCL21, CCR9, CCR10, CCL18, CCL2/MCP-1, MIP-1α/CCL3, CXCL1, CXCL2, CXCL3, CXCL4, CXCL5, CXCL8, CXCL12/SDF-1α, CXCR2, CXCR3, CXCR4, CXCR7, erythropoietin (EPO), CCL5/RANTES, hepatocyte growth factor activator (HGFA), insulin-like growth factor-1 (IGF-1), cylooxygenase-2 (COX-2), CXCL14, prostaglandin E2, platelet derived growth factor, vascular endothelial growth factor (VEGF) and combinations thereof.

In another aspect, the invention provides a method of treating or preventing cancer metastasis comprising administering to a subject in need thereof an effective amount of a cancer cell trap of the invention, wherein metastatic cancer cells migrate and accumulate in the cancer cell trap, thereby treating or preventing metastasis in the subject.

In some embodiments, cancer stem cells migrate to the cancer cell trap.

In some embodiments, the cancer is selected from the group consisting of melanoma, prostate cancer, leukemia, squamous cell carcinoma, astrocytoma, Kaposi's sarcoma, glioblastoma, lung cancer, bladder cancer, head and neck cancer, ovarian cancer, uterine cancer, breast cancer, lung cancer, glioma, colorectal cancer, genitourinary cancer, gastrointestinal cancer, thyroid cancer and skin cancer.

The cancer cell trap may be administered to the subject or patient using methods known in the medical and pharmaceutical arts. In some embodiments, the cancer cell trap is implanted into the subject. In some embodiments, the cancer cell trap is injected into the subject. In some embodiments, the subject is a mammal such as a human.

In some embodiments, the methods of the invention can be combined with any cancer treatment. In some embodiments, the treatment is selected from the group consisting of surgery, chemotherapy, and radiation.

In some embodiments, the method of the invention further comprises subjecting the implanted or injected cancer cell trap to radiation treatment thereby killing the metastatic cancer cells that have migrated to the cancer cell trap. In some embodiments, the cancer cell trap is removed from the patient after a period of time.

In another aspect, the invention provides a method of detecting cancer metastasis, comprising administering to a subject in need thereof a cancer cell trap, wherein metastatic cancer cells migrate and accumulate in the cancer cell trap; and assaying the cancer cell trap for the presence of metastatic cancer cells, thereby detecting cancer metastasis in the subject. In some embodiments, the cancer cells are removed from the cancer cell trap and evaluated. In some embodiments, the cells are removed from the trap while the trap is still present in the subject. In some embodiments, the cancer cell trap is removed from the subject and the cells are optionally removed before they are evaluated.

It is to be understood that both the foregoing general description of the invention and the following detailed description are exemplary, and thus do not restrict the scope of the invention.

BRIEF DESCRIPTION OF THE FIGURES

The skilled artisan will understand that the drawings, described below, are for illustration purposes only. The drawings are not intended to limit the scope of the present teachings in any way.

FIG. 12. (A-H) Characterization of gelatin MB scaffolds. Scanning electron microscopy images of (A) control (low mag) and (B) Gelatin MB scaffold (low mag). Scale bar: 100 µm. Scanning electron microscopy images of (C) control (high mag) and (D) gelatin MB (high mag). Scale bar: 50 µm. Coomassie blue staining of internal cross sections was done to determine the internal architecture and protein localization in (E) control and (F) gelatin MB scaffolds. (G) Chart showing porosity and mechanical strength of control and gelatin MB scaffolds. (H) Chart showing release of NIR dye conjugated EPO was determined using a fluorescence plate reader.

FIG. 15. Effect of Cancer cell traps on Melanoma Cancer Cells. The number of melanoma cancer cells were recruited to the implant sites of hydrogel cancer cell traps releasing with either RANTES, IL-8, or saline (as control) was monitored. The results of these experiments are demonstrated in chart (A). The survival duration of the treated animals was also monitored. The results of these experiments are summarized in chart (B).

FIG. 16. Effect of Cancer cell traps On PC3 Prostate Cancer Cells. The number of prostate cancer cells at the sites of implanted tissue scaffolds capable of releasing either VEGF (50 ng/implant) or EPO (1,000 ID/implant) was monitored. The results of these experiments are demonstrated in chart (A). The survival duration of the treated animals was also monitored. The results of these experiments are summarized in chart (B).

DETAILED DESCRIPTION OF THE INVENTION

Figure 1:
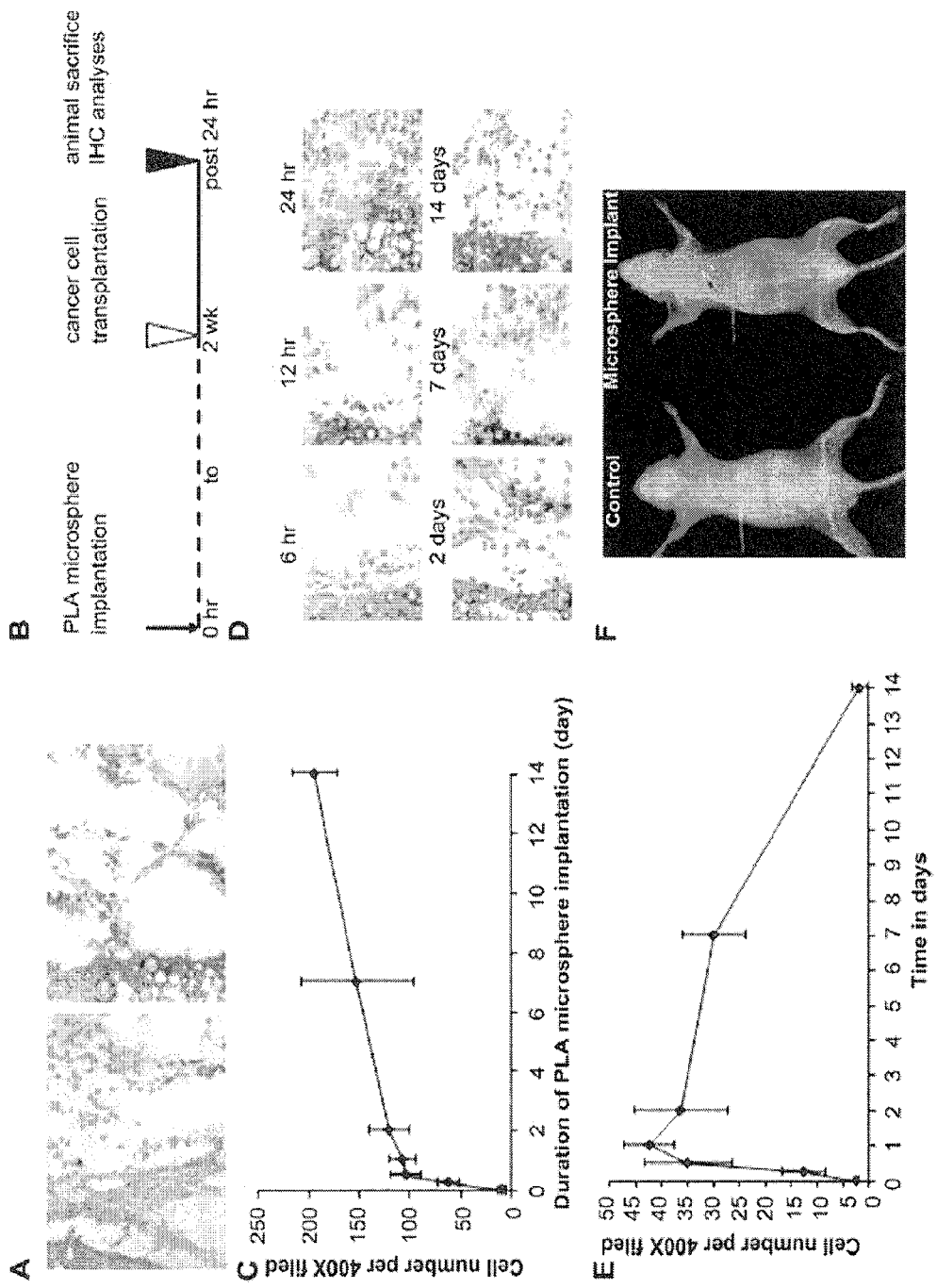
FIG. 1. Foreign body reactions trigger tumor cell migration. Pre-existing 1-day old subcutaneous implants were found to attract the immigration of CD11b. inflammatory cells (A, left) and intraperitoneally transplanted B16F10 melanoma cells (A, right). To determine the influence of inflammatory signals in cancer cell migration, varying degrees of inflammatory stimuli intensities were stimulated from 6 h to 2 weeks according to the experimental time table (B). It was found that large numbers of CD11b. inflammatory cells were recruited to the implantation sites in 12 h and the influx of inflammatory cells was slowed down after that. These results depict different stages of biomaterial-mediated inflammatory responses (C). The stages of inflammatory responses also affect the extent of melanoma cell recruitment (D). Melanoma cell accumulation in the implant area reached a peak around 24 h post microsphere implantation (E). Inflammation-induced cancer metastasis is also detected in optical imaging method by labeling melanoma cells with Kodak X-Sight 761 near-infrared nanospheres (F).

The present invention is based on the surprising discovery that metastatic cancer cells migrate and accumulate in a "cancer cell trap" when placed in a subject. The metastasis of the cancer can thereby be detected in the subject having cancer. In some embodiments, the cancer cell trap can also suppress or prevent metastatic tumor formation in the subject, thereby prolonging survival of the subject. Without being bound by theory as to how the invention works, it is believed that the cancer cell trap may induce a chemokine concentration gradient in blood and as a result, circulating metastatic cancer cells preferentially migrate and accumulate in the cancer cell trap instead of vital organs.

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

"Cancer cell trap" as encompassed by the present invention refers to a material that enables the migration and accumulation of metastatic cancer cells in the material for a period of time. In some embodiments, the cancer cell trap is capable of releasing one or more molecules selected from proteins, chemokines, growth factors, therapeutics, chemotherapeutic agents, anti-cancer agents and combinations thereof.

As used herein, the term "about" means plus or minus 10% of the numerical value of the number with which it is being used.

A "therapeutically effective amount" or "effective amount" as used herein is an amount sufficient to decrease, suppress, prevent or ameliorate the symptoms associated with cancer, including suppressing or decreasing the formation of metastatic tumors.

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the pathological condition. In other certain aspects of the invention, those in need of treatment include those already with cancer as well as those prone to have cancer or in those in whom cancer metastasis is to be prevented.

As used herein, "cancer" refers to a pathophysiological condition whereby a cell or cells is characterized by dysregulated and/or proliferative cellular growth and the ability to induce said growth, either by direct growth into adjacent tissue through invasion or by growth at distal sites through metastasis, which includes but is not limited to, carcinomas and sarcomas, such as, for example, acute lymphoblastic leukemia, acute myeloid leukemia, adrenocortical cancer, AIDS-related cancers, AIDS-related lymphoma, anal cancer, astrocytoma (including, for example, cerebellar and cerebral), basal cell carcinoma, bile duct cancer, bladder cancer, bone cancer, brain stem glioma, brain tumor (including, for example, ependymoma, medulloblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (including, for example, gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (including, for example, intraocular melanoma, retinoblastoma, gallbladder cancer, gastric cancer, gastrointestinal carcinoid tumor, gastrointestinal stromal tumor (GIST), germ cell tumor (including, for example, extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (including, for example, endocrine pancreas), Kaposi's sarcoma, laryngeal cancer, leukemia, lip and oral cavity cancer, liver cancer, lung cancer (including, for example, non-small cell), lymphoma, macroglobulinemia, malignant fibrous histiocytoma of bone/osteosarcoma, medulloblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (including, for example, ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sézary syndrome, skin cancer (including, for example, non-melanoma or melanoma), small intestine cancer, supratentorial primitive neuroectodermal tumors, T-Cell lymphoma, testicular cancer, throat cancer, thymoma, thymoma and thymic carcinoma, thyroid cancer, transitional cell cancer of the renal pelvis and ureter, trophoblastic tumor (including, for example, gestational), unusual cancers of childhood and adulthood, urethral cancer, endometrial uterine cancer, uterine sarcoma, vaginal cancer, viral induced cancers (including, for example, HPV induced cancer), vulvar cancer, Waldenström's macroglobulinemia, Wilms' Tumor, and women's cancers.

The term "hydrogel" is used in the conventional sense to refer to water-swellable polymeric or polysaccharide-based matrices that can absorb a substantial amount of water to form elastic gels, wherein "matrices" are three-dimensional networks of macromolecules held together by covalent or noncovalent crosslinks. Some of these hydrogel can be solidified with temperature- or pH-changes. Upon placement in the body, the hydrogel can be used as carrier to release a variety of biomolecules.

As used herein, terms such as "drug," "agent," "pharmaceutical" may be used interchangeably. In general, these terms refer to any chemical substance used in the treatment, cure, prevention, or diagnosis of a disease or condition or to otherwise change the physical or mental status of a human or other animal, regardless of molecular weight. A pharmaceutical composition may also be prepared using a drug in combination with a drug delivery vehicle of the invention. The pharmaceutical composition can comprise a drug in a suitable polymeric form and a biologically acceptable carrier. Suitable polymeric forms include microcapsules, microparticles, films, polymeric coatings, and nanoparticles.

Cancer Cell Trap

In one embodiment, the invention provides a cancer cell trap for treating, preventing and/or diagnosing cancer metastasis, wherein metastatic cancer cells are capable of migrating and accumulating in the cancer cell trap over a period of time when the cancer cell trap is placed into a subject.

In accordance with some embodiments of the invention, the cancer cell trap can be fabricated with the capability to release one or more bioactive molecules and/or drugs, such as proteins, chemokines, growth factors and chemotherapeutic or anti-cancer agents.

The cancer cell trap can be made from one or more materials and the materials that can be used in fabricating the cancer cell trap are not limiting. Preferably, the material is biocompatible and generally non-toxic to the subject's healthy, non-cancerous cells.

In some embodiments, the cancer cell trap comprises one or more materials selected from water soluble polymers, including, but not limited to, dextran, derivatives of polymethacrylamide, PEG, maleic acid, malic acid, and maleic acid anhydride and may include these polymers and a suitable coupling agent, including 1-ethyl-3 (3-dimethylaminopropyl)-carbodiimide, also referred to as carbodiimide. In some embodiments, polymers may be degradable or nondegradable or of a polyelectrolyte material. In some embodiments, degradable polymer materials include poly-L-glycolic acid (PLGA), poly-DL-glycolic, poly-L-lactic acid (PLLA), PLLA-PLGA copolymers, poly(DL-lactide)-block-methoxy polyethylene glycol, polycaprolacton, poly (caprolacton)-block-methoxy polyethylene glycol (PCL-MePEG), poly(DL-lactide-co-caprolactone)-block-methoxy polyethylene glycol (PDLLACL-MePEG), some polysaccharide (e.g., hyaluronic acid, polyglycan, chitoson), proteins (e.g., fibrinogen, albumin, collagen, extracellular matrix), peptides (e.g., RGD, polyhistidine), nucleic acids (e.g., RNA, DNA, single or double stranded), viruses, bacteria, cells and cell fragments, organic or carbon-containing materials, as examples. Nondegradable materials include natural or synthetic polymeric materials (e.g., polystyrene, polypropylene, polyethylene teraphthalate, polyether urethane, polyvinyl chloride, silica, polydimethyl siloxane, acrylates, arcylamides, poly(vinylpyridine), polyacroleine, polyglutaraldehyde), some polysaccharides (e.g., hydroxypropyl cellulose, cellulose derivatives, dextran®, dextrose, sucrose, ficoll®, percoll®, arabinogalactan, starch), and hydrogels (e.g., polyethylene glycol, ethylene vinyl acetate, N-isopropylacrylamide, polyamine, polyethyleneimine, poly-aluminum chloride).

In some embodiments, the cancer cell trap comprises materials selected from the group consisting of a scaffold structure, hydrogel, nanoparticles and/or microparticles. In some embodiments, the cancer cell trap comprises one or more materials with controlled release properties capable of releasing bioactive molecules and/or chemotherapeutic agents. In some embodiments, the hydrogel cancer cell trap is a liquid composition and is injected or implanted in the subject. In some embodiments, the nanoparticles and/or microparticles cancer cell trap is a liquid composition of particles and is injected or implanted in the subject. In some embodiments, the scaffold structure is a solid composition and is implanted in the subject or injected via a surgical procedure. In some embodiments, the scaffold structure, hydrogel, microparticles and/or nanoparticles are injected via 19-21 gauge needles.

In some embodiments, the cancer cell traps are implanted or injected in the subcutaneous space and/or intraperitoneal cavities.

In some embodiments, the cancer cell trap comprises effective amounts of one or more bioactive molecules. In some embodiments, the bioactive molecules are added to the cancer cell trap by physical absorption. In some embodiments, the bioactive molecules facilitate the recruitment and migration of metastatic cancer cells to the cancer cell trap. In some embodiments, the bioactive molecules are selected from the group consisting of IL-1, IL-4, IL-8, IL-10, IL-13, IL-17, CCL2, CCL5, CCL9, CCL18, CCL19, CCL20, CCL21, CCL25, CCL27, CCR4, CCR5, CCR7/CCL21, CCR9, CCR10, CCL18, CCL2/MCP-1, MIP-1α/CCL3, CXCL1, CXCL2, CXCL3, CXCL4, CXCL5, CXCL8, CXCL12/SDF-1α, CXCR2, CXCR3, CXCR4, CXCR7, erythropoietin (EPO), CCL5/RANTES, hepatocyte growth factor activator (HGFA), insulin-like growth factor-1 (IGF-1), cylooxygenase-2 (COX-2), CXCL14, prostaglandin E2, platelet derived growth factor, vascular endothelial growth factor (VEGF) and combinations thereof. Bioactive fragments and variants can also be used.

In some embodiments, the cancer cell trap releases an effective amount of bioactive molecules after it is injected or implanted in a subject. In some embodiments the release is over an extended period of time. In some embodiments, the bioactive molecules are released over a period of 1-6 months. In some embodiments, the bioactive molecules are released over a period of about 1 week, 2 weeks, 3 weeks, or 4 weeks. In some embodiments, the bioactive molecules are released over a period of about 14 days. In some embodiments, the bioactive molecules are released over a period of about 7-10 days. In some embodiments, the bioactive molecules are released over a period of about 2-7 days.

By the term "effective amount" with regard to the bioactive molecules, is meant an amount that produces the desired effect for which it is administered, viz., inducing the recruitment and migration of the metastatic cancer cells to the cancer cell trap. The exact amount will depend on the particular agent, the subject to be treated, and will be ascertainable by a person skilled in the art using known methods and techniques for determining effective doses. In some embodiments, the amount of the bioactive molecule to be administered includes between about 0.05 ng/kg/day to about 1 mg/kg/day. In some embodiments, the amount of bioactive molecule that can be administered in amounts between about 0.1 ng/kg/day to about 1 µg/kg/day.

In some embodiments, the bioactive molecules may be released in the following concentrations ranges: IL-8 (0.01-250 ng/day/1 ml or 1 cubic cm of implant), CCLI9 (10 µg-1000 ng/day/1 ml or 1 cubic cm of implant), CCL20 (0.1-4000 nano moles/day/1000 ml or 1000 cubic cm of implant), CCL21 (0.01-100 micro moles/day/1000 ml or 1000 cubic cm of implant), CCL2/MCP-1 (0.05-100 ng/day/1 ml or 1 cubic cm of implant), CCL3 (10-1000 ng/day/1 ml or 1 cubic cm of implant), CXCL12/SDF-1α (0.5-500 nano moles/day/1000 ml or 1000 cubic cm of implant), CCL5/RANTES (0.01-1000 ng/day/1 ml or 1 cubic cm of implant), and EPO (1-10000 I.U./day/1 ml or 1 cubic cm of implant), CCL5/RANTES (0.2-500 ng/day/1 ml or 1 cubic cm of implant), and VEGF (0.01-100 ng/day/1 ml or 1 cubic cm of implant).

In some embodiments, the bioactive molecules may be released in the following concentrations ranges: IL-8 (0.1-20 ng/day/1 ml or 1 cubic cm of implant), CCLI9 (100 µg-100 ng/day/1 ml or 1 cubic cm of implant), CCL20 (1-400 nano moles/day/1000 ml or 1000 cubic cm of implant), CCL21 (0.1-10 micro moles/day/1000 ml or 1000 cubic cm of implant), CCL2/MCP-1 (0.5-10 ng/day/1 ml or 1 cubic cm of implant), CCL3 (1-100 ng/day/1 ml or 1 cubic cm of implant), CXCL12/SDF-1α (5-50 nano moles/day/1000 ml or 1000 cubic cm of implant), CCL5/RANTES (0.1-10 ng/day/1 ml or 1 cubic cm of implant), and EPO (1-100 I.U./day/1 ml or 1 cubic cm of implant), CCL5/RANTES (2-50 ng/day/1 ml or 1 cubic cm of implant), and VEGF (0.1-10 ng/day/1 ml or 1 cubic cm of implant).

In some embodiments, the cancer cell trap may be fabricated to release independently or combinations of recombinant human HGF/SF (10 ng/day/1 ml or 1 cubic cm of implant), MCP-1 (0.5 to 10 ng/day/1 ml or 1 cubic cm of implant), CXCL12/SDF-1α (5 to 50 nano moles/day/1000 ml or 1000 cubic cm of implant), CCL5/RANTES (0.5 to 10 ng/day/1 ml or 1 cubic cm of implant), and EPO (1 to 100 I.U./day/1 ml or 1 cubic cm of implant).

In some embodiments, the cancer cell trap may be fabricated to release hepatocyte growth factor/scatter factor (HGF/SF), MCP-1α, RANTES, SDF-1α, MCP-1, EPO, histamine, or MIP-1α, and combinations thereof. In some embodiments, these cancer cell traps may be fabricated using methods described in Otsuka, S. and G. Bebb, *J Thorac Oncol*, 2008. 3(12): p. 1379-83.

In some embodiments, the cancer cells are recruited to the cancer cell trap based on the chemokine gradient and localized concentrations of the chemokine In some embodiments wherein EPO is released, the injection quantity is about 600 units/0.027 milliliter of hydrogel/particle cancer traps or 27 cubic millimeters scaffold traps. In some embodiments, the release rate is about 1.5 to about 2.5 international units/day. In some embodiments, EPO is released over a period of greater than about 30 days.

In some embodiments wherein RANTES/CCL5 is released, the injection quantity is about 600 ng/milliliter of hydrogel/particle cancer traps or 1 cubic centimeters scaffold traps. In some embodiments, the release rate is about 10 ng/day. In some embodiments, RANTES/CCL5 is released over a period of greater than about 21 days.

In some embodiments wherein hepatocyte growth factor (HGF/SF) is released, the injection quantity is about 900 ng/milliliter of hydrogel/particle cancer traps or 1 cubic centimeters scaffold traps. In some embodiments, the release rate is about 15 ng/day. In some embodiments, hepatocyte growth factor (HGF/SF) is released over a period of greater than about 28 days.

In some embodiments wherein SDF-1α is released, the injection quantity is about 10 µg/milliliter of hydrogel/particle cancer traps or 1 cubic centimeters scaffold traps. In some embodiments, the release rate is about 100 ng/day. In some embodiments, SDF-1α is released over a period of greater than about 24 days.

In some embodiments, the cancer cell trap of the present invention may be fabricated to release: RANTES (10-500 µg/kg body weight), EPO (1-20 IU/kg body weight), SDF-1α (0.1-10 mg/kg body weight), MCP-1 (0.1-10 mg/kg body weight), and MIP-1α (0.1-10 mg/kg body weight).

In some embodiments, two or more bioactive molecules are released from the cancer cell trap.

The cancer cell trap is used to recruit metastatic cancer cells. The metastatic cancer cell is not limiting, and can include any metastatic cancer cell. In some embodiments, the metastatic cancer cell is selected from the group consisting of melanoma, prostate cancer, leukemia, squamous cell carcinoma, astrocytoma, Kaposi's sarcoma, glioblastoma, lung cancer, bladder cancer, head and neck cancer, ovarian cancer, uterine cancer, breast cancer, lung cancer, glioma, colorectal cancer, genitourinary cancer, gastrointestinal cancer, thyroid cancer and skin cancer.

In some embodiments, the cancer cell trap may comprise effective amounts of one or more anti-cancer or chemotherapeutic agents, which can be used to kill or inhibit the growth of metastatic cancer cells. In some embodiments, the chemotherapeutic agent is released from the cancer cell trap and also kills or inhibits circulating metastatic cells in addition to the cells accumulated in the cancer cell trap. A suitable chemotherapeutic or anti-cancer agent for use in the invention can be any chemical substance known to be useful for treating cancer, for example, Abraxane, Aldara, Alimta, Aprepitant, Arimidex, Aromasin, Arranon, Arsenic Trioxide, Avastin, Bevacizumab, Bexarotene, Bortezomib, Cetuximab, Clofarabine, Clofarex, Clolar, Dacogen, Dasatinib, Ellence, Eloxatin, Emend, Erlotinib, Faslodex, Femara, Fulvestrant, Gefitinib, Gemtuzumab Ozogamicin, Gemzar, Gleevec, Herceptin, Hycamtin, Imatinib Mesylate, Iressa, Kepivance, Lenalidomide, Levulan, Methazolastone, Mylosar, Mylotarg, Nanoparticle Paclitaxel, Nelarabine, Nexavar, Nolvadex, Oncaspar, Oxaliplatin, Paclitaxel, Paclitaxel Albumin-stabilized Nanoparticle Formulation, Palifermin, Panitumumab, Pegaspargase, Pemetrexed Disodium, Platinol-AQ, Platinol, Revlimid, Rituxan, Sclerosol Intrapleural Aerosol, Sorafenib Tosylate, Sprycel, Sunitinib Malate, Sutent, Synovir, Tamoxifen, Tarceva, Targretin, Taxol, Taxotere, Temodar, Temozolomide, Thalomid, Thalidomide, Topotecan Hydrochloride, Trastuzumab, Trisenox, Vectibix, Velcade, Vidaza, Vorinostat, Xeloda, Zoledronic Acid, Zolinza, Zometa, doxorubicin, adriamycin, bleomycin, daunorubicin, dactinomycin, epirubicin, idarubicin, mitoxantrone, valrubicin, hydroxyurea, mitomycin, fluorouracil, 5-FU, methotrexate, floxuridine, interferon alpha-2b, glutamic acid, plicamycin, 6-thioguanine, aminopterin, pemetrexed, raltitrexed, cladribine, clofarabine, fludarabine, mercaptopurine, pentostatin, capecitabine, cytarabine, carmustine, BCNU, lomustine, CCNU, cytosine arabinoside, cyclophosphamide, estramustine, hydroxyurea, procarbazine, mitomycin, busulfan, medroxyprogesterone, estramustine phosphate sodium, ethinyl estradiol, estradiol, megestrol acetate, methyltestosterone, diethylstilbestrol diphosphate, chlorotrianisene, testolactone, mephalen, mechlorethamine, chlorambucil, chlormethine, ifosfamide, bethamethasone sodium phosphate, dicarbazine, asparaginase, mitotane, vincristine, vinblastine, etoposide, tenoposide, Topotecan, IFN-gamma, irinotecan, campto, irinotecan analogs, carmustine, fotemustine, lomustine, streptozocin, carboplatin, oxaliplatin, BBR3464, busulfan, dacarbazine, mechlorethamine, procarbazine, thioTEPA, uramustine, vindesine, vinorelbine, alemtuzumab, tositumomab, methyl aminolevulinate, porfimer, verteporfin, lapatinib, nilotinib, vandetanib, ZD6474, alitretinoin, altretamine, amsacrine, anagrelide, denileukin diftitox, estramustine, hydroxycarbamide, masoprocol, mitotane, tretinoin, or other anticancer agents, including, for example, cytotoxic agents, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial or exotoxic agents. In further particular aspects of the invention, an anticancer agent comprises two or more of the foregoing anticancer agents.

In some embodiments, the cancer cell trap can be fabricated with a combination of anti-cancer or chemotherapeutic agents. In some embodiments, a combination of agents includes, for example, CHOP (Cytoxan, Hydroxyrubicin (Adriamycin), Oncovin (Vincristine), Prednisone), CHOP-R (CHOP, rituximab), FOLFOX (Fluorouracil, leucovorin (folinic acid), oxaliplatin), VAD (Vincristine, Adriamycin (doxorubicin), dexamethasone), Thal/Dex (Thalidomide, dexamethasone), COP or CVP (Cyclophosphamide, vincristine (Oncovin), and prednisone), m-BACOD (Methotrexate, bleomycin, doxorubicin (Adriamycin), cyclophosphamide, vincristine (Oncovin), dexamethasone (Decadron)), ProMACE-CytaBOM (Prednisone, doxorubicin (adriamycin), cyclophosphamide, etoposide, cytarabine, bleomycin, vincristine (Oncovin), methotrexate, leucovorin), COPP (Cyclophosphamide, Oncovin (vincristine), procarbazine, prednisone), MACOP-B (Methotrexate, leucovorin, doxorubicin (Adriamycin), cyclophosphamide, vincristine (Oncovin), prednisone, bleomycin), MOPP (Mechlorethamine, vincristine (oncovin), procarbazine, prednisone), ProMACE-MOPP (Methotrexate, doxorubicin (Adriamycin), cyclophosphamide, etoposide, MOPP), ABVD (Adriamycin, bleomycin, vinblastine, dacarbazine), BEACOPP (Bleomycin, etoposide, Adriamycin (doxorubicin), cyclophosphamide, Oncovin (vincristine), procarbazine, prednisone), Stanford V (Doxorubicin (Adriamycin), mechlorethamine, bleomycin, vinblastine, vincristine (Oncovin), etoposide (VP-16), prednisone), ECF (Epirubicin, cisplatin, fluorouracil), BEP (Bleomycin, etoposide, platinum (cisplatin)), and PCV (Procarbazine, lomustine (CCNU), vincristine).

By the term "effective amount" with regard to the chemotherapeutic agent is meant an amount that produces the desired effect for which it is administered, viz., killing or inhibiting the growth of the metastatic cancer cells. The exact amount will depend on the particular agent, the subject to be treated, and will be ascertainable by a person skilled in the art using known methods and techniques for determining effective doses. In some embodiments, the amount of the chemotherapeutic agent to be administered includes between about 0.01 µg/kg/day to about 100 mg/kg/day. In some embodiments, the amount of chemotherapeutic agent that can be administered includes between about 0.1 mg/kg/day to about 10 mg/kg/day.

In some embodiments, the cancer cell trap is fabricated to incorporate and/or release paclitaxel, doxorubicin, and/or vincristine. In some embodiments, the cancer cell traps can be fabricated to release doxorubicin at a rate of about 0.1-1000 µg/day, 0.5-500 µg/day, 1-100 µg/day or 2-20 µg/day per 1 ml of hydrogel/particle cancer traps or 1 cubic centimeters scaffold traps. In some embodiments, the cancer cell traps can be fabricated to release paclitaxel at a rate of about 0.01-500 mg/day, 0.1-100 mg/day, 0.1-50 mg/day, 0.2-20 mg/day or 0.2-2 mg/day per 1 ml of hydrogel/particle cancer traps or 1 cubic centimeters scaffold traps.

The cancer cell traps can be fabricated into any type of shape. In some embodiments, solid cancer cell traps have a disc shape. In some embodiments, solid cancer cell traps can be fabricated to have a tubular shape. In some embodiments, the tubular structure has an opening on one or both sides. In some embodiments, the tubular structure has a porous structure which allows infiltration of cancer cells from the sides and the opening to the inner lumen of the cancer cell trap. In some embodiments, the cancer cells can be recovered from the inner lumen of the cancer cell trap via a needle, such as an 18-21 gauge needle.

Scaffold Cancer Cell Trap

In some embodiments, the cancer cell trap is fabricated as a scaffold structure. In some embodiments, the cancer cell trap is a tissue scaffold. In some embodiments, the cancer cell trap comprises one or more extracellular matrix components. In some embodiments, the cancer cell trap is a microbubble scaffold. In some embodiments, the cancer cell trap is made from synthetic polymers. In some embodiments, the cancer cell trap is made from polymers and proteins. In some embodiments, the scaffold structure is prepared from one or more proteins, polymers, and combinations thereof. In some embodiments, the proteins are extracellular matrix proteins, such collagen I, collagen III, elastin and fibronectin. In some embodiments, the scaffold is degradable. In some embodiments, the scaffold comprises a biodegradable polymer and one or more polypeptides. In some embodiments, scaffolds can be created from tissues wherein the cells are removed, leaving behind a scaffold structure comprising extracellular matrix components.

In some embodiments, the scaffold structure is generally porous in nature. In some embodiments, the porosity ranges from about 10-97%, about 25-98%, about 50-95% and about 80-90%.

In some embodiments, the scaffolds can be fabricated from biodegradable polymers such as aliphatic polyesters, alginate, cellulose, chitin, chitosan, collagen, copolymers of glycolide, copolymers of lactide, elastin, fibrin, glycolide/l-lactide copolymers (PGA/PLLA), glycolide/trimethylene carbonate copolymers (PGA/TMC), glycosaminoglycans, lactide/tetramethylglycolide copolymers, lactide/trimethylene carbonate copolymers, lactide/ε-caprolactone copolymers, lactide/σ-valerolactone copolymers, L-lactide/dl-lactide copolymers, methyl methacrylate-N-vinyl pyrrolidone copolymers, modified proteins nylon-2 PHBA/γ-hydroxyvalerate copolymers (PHBA/HVA), PLA/polyethylene oxide copolymers, PLA-polyethylene oxide (PELA), poly (amino acids), poly(trimethylene carbonates), poly hydroxyalkanoate polymers (PHA), poly(alklyene oxalates), poly (butylene diglycolate), poly(hydroxy butyrate) (PHB), poly (n-vinyl pyrrolidone), poly(ortho esters), polyalkyl-2-cyanoacrylates, polyanhydrides, polycyanoacrylates, polydepsipeptides, polydihydropyrans, Poly-dl-lactide, (PDLLA), polyesteramides, polyesters of oxalic acid, polyglycolide (PGA), polyiminocarbonates, polylactides (PLA), poly-l-lactide (PLLA), polyorthoesters, poly-p-dioxanone (PDO), polypeptides, polyphosphazenes, polysaccharides, polyurethanes (PU) polyvinyl alcohol (PVA) poly-β-hydroxypropionate (PHPA), poly-β-hydroxybutyrate (PBA), poly-α-valerolactone poly-β-alkanoic acids, poly-β-malic acid (PMLA), poly-ε-caprolactone (PCL), pseudo-Poly(Amino Acids), starch, trimethylene carbonate (TMC), and/or tyrosine based polymers.

In some embodiments, the scaffold is fabricated from PLGA, albumin, collagen, gelatin, immunoglobulins, extracellular matrix proteins, fibronectin and combinations thereof. In some embodiments, the scaffold comprises a degradable polymer and polypeptides.

In some embodiments, the scaffold structure is a microbubble scaffold (MB), which results in a porous scaffold that is capable of incorporating cells and also releasing bioactive molecules. Microbubble scaffolds can be prepared, for example, according to techniques discussed in Nair et al., Novel polymeric scaffolds using protein microbubbles as porogen and growth factor carriers. *Tissue Eng Part C Methods*, 2010. 16(1): p. 23-32. In some embodiments, microbubbles are first prepared and then combined with polymers to form the microbubble scaffold. Microbubbles can also be loaded with bioactive molecules to produce scaffolds that release bioactive molecules in accordance with some embodiments of the invention.

In some embodiments, the microbubbles can be prepared as follows: a solution of protein such as BSA (e.g., 5% w/v, 10% w/v, 20% w/v or 50% w/v) is overlaid with nitrogen gas. The mixture is sonicated using a probe sonicator (Ultrasonix, Bothell, Wash.) at 20 kHz for 10 s. This procedure results in the formation of nitrogen gas-filled MB that are surrounded by a BSA protein shell. The MBs can be transferred to glass tubes and kept at 48° C. To observe the physical structure of MB, a small droplet of the MB can be placed on a glass slide and then imaged under a microscope (Leica Microsystems, Wetzlar, Germany). The MB size distribution generally ranges from 50 to 200 μm in diameter. To synthesize a biomolecule-loaded MB (labeled as MB-chemokine), a chemokine, such as IGF-1 (for example, 500 ng/mL) solution is mixed with BSA solution before sonication under nitrogen gas as described above.

In some embodiments, the microbubbles can then be combined with various concentrations of polymer solution (e.g., 5% w/v, 7.5% w/v, and 10% w/v) to create MB-embedded porous scaffolds. Such MB-polymer mixtures can be phase separated at various temperatures (0° C., 20° C., and 196° C.). Briefly, in some embodiments, 7.5% w/v PLGA can be dissolved in 1,4-dioxane by vortexing for about 20 min until the polymer completely dissolved in the solvent. In some embodiments, the polymer solution can then be mixed with the BSA-MB or biomolecule-loaded BSA-MB (e.g., 5% w/v BSA) in a ratio of 1:1. After gentle agitation for about 3 min at room temperature, the polymer-solution mixtures in glass Petri dishes (5 cm diameter) are then quenched in liquid nitrogen to induce phase separation. The solidified scaffolds can then lyophilized for 48 h at 0.03 mbar vacuum, for example, in a Freezone 12 lyophilizer (Labconco, Kansas City, Mo.). For producing biomolecule loaded MB-embedded scaffolds, biomolecule-loaded MB (for example, MB-IGF-1, MB manufactured in the presence of 500 ng/mL IGF-1) is used as porogens.

In some embodiments, the microbubble scaffold of the present invention may be fabricated from a single protein or protein mixtures in different ratios. In some embodiments, the microbubble scaffold is fabricated from albumin, collagen, gelatin, immunoglobulins, extracellular matrix proteins, fibronectin, and combinations thereof.

In some embodiments, the microbubble scaffold releases one or more biomolecules. In some embodiments, the microbubble scaffold is capable of releasing biomolecules in the following concentrations ranges: IL8 (0.1-20 ng/1 cubic centimeters scaffold/day), CCLI9 (100 μg-100 ng/1 cubic centimeters scaffold/day), CCL20 (1-400 nmole/1000 cubic centimeter scaffold/day), CCL2I (0.1-10 micromole/1000 cubic centimeter scaffold/day), CCL2/MCP-1 (0.5-10 ng/1 cubic centimeter scaffold/day), CCL3 (1-100 ng/1 cubic centimeter scaffold/day), CXCLI2/SDF-Ia (5-50 nanonmole/1000 cubic centimeter scaffold/day), CCL5/RANTES (0.1-10 ng/1 cubic centimeter scaffold/day), and EPO (1-100 I.U./1 cubic centimeter scaffold/day), CCL5/RANTES (2-50 ng/1 cubic centimeter scaffold/day), and VEGF (0.1-10 ng/1 cubic centimeter scaffold/day).

In some embodiments, the microbubble scaffolds have a porosity ranging from 70-98%. In some embodiments, the microbubble scaffold has a pore size ranging from 10 μm to 300 μm. In some embodiments, the pore size is selected from about 20 μm to about 200 μm, from about 40 μm to about 150 μm, from about 80 μm to about 130 μm, and from about 100 μm to about 120 μm.

The microbubble scaffold may have a bolus release of 5 to 35% of loaded biomolecule. For example, the microbubble scaffold may be fabricated to have a bolus release of 20% of biomolecule, including chemokine, growth factor or protein, within the first 24 hours.

In some embodiments, the scaffolds are fabricated to provide a sustained release biomolecules of approximately 2-10% of total amounts per day.

Nanoparticles and or Microparticles

In some embodiments, the cancer cell traps can also be fabricated using microparticles and/or nanoparticles. In some embodiments, the particles are capable of releasing various bioactive molecules.

In some embodiments, the nanoparticles and microparticles can be fabricated from a single protein or protein mixtures in different ratios. For instance, the scaffolds may be fabricated from PLGA, albumin, collagen, gelatin, immunoglobulins, extracellular matrix proteins, or fibronectin, and combinations thereof.

As used herein, terms such as "microparticle," "nanoparticle," "microscopic particle" or "functionalized particle" are used to refer to microscopic (few micrometers in size to few millimeters in size) or submicroscopic (less than one micrometer) solid colloidal objects, generally cylindrical or spherical in shape with a semipermeable shell or shaped like a permeable nano-ball. In some embodiments, the nanoparticle and microparticle compositions are in liquid form. In some embodiments, the compositions are injected or implanted surgically in a subject. In some embodiments, the particles are injected using an 18-23 gauge needle.

One or more biomolecules or drugs or other relevant materials (e.g., those used for diagnostic purposes, such as in nuclear medicine or in radiation therapy) may be dissolved within the nanoparticles or microparticles, entrapped, encapsulated, absorbed, adsorbed, covalently linked, or otherwise attached, using techniques known by persons skilled in the art.

Furthermore, particles of the present invention may be coated. When a relevant material as just described is added to a particles, it may be considered a tagged particle.

In some embodiments, the particles of the present invention can be made as a metal particle, carbon particle, graphite particle, polymer particle, hydrogel particle, polysaccharide particle, liquid particle or porous particle. Thus, micro- and nanoparticles may be metal, carbon, graphite, polymer, and may be loaded with a light or color absorbing dye, an isotope, biomolecules/cytokines/chemokines/growth factors, a radioactive species, chemotherapy drugs, or be porous having gas-filled pores.

In some embodiments, the particles comprise one or more polymers or polyelectrolytes, including copolymers of water soluble polymers, including, but not limited to, dextran, derivatives of poly-methacrylamide, PEG, maleic acid, malic acid, and maleic acid anhydride and may include these polymers and a suitable coupling agent, including 1-ethyl-3(3-dimethylaminopropyl)-carbodiimide, also referred to as carbodiimide. Polymers may be degradable or nondegradable in the body or polyelectrolyte materials. Degradable polymer materials include poly-L-glycolic acid (PLGA), poly-DL-glycolic, poly-L-lactic acid (PLLA), PLLA-PLGA copolymers, poly(DL-lactide)-block-m-ethoxy polyethylene glycol, polycaprolacton, poly(caprolacton)-block-methoxy polyethylene glycol (PCL-MePEG), poly(DL-lactide-co-caprolactone)-block-methoxy polyethylene glycol (PDL-LACL-MePEG), some polysaccharide (e.g., hyaluronic acid, polyglycan, chitoson), proteins (e.g., fibrinogen, albumin, collagen, extracellular matrix), peptides (e.g., RGD, polyhistidine), nucleic acids (e.g., RNA, DNA, single or double stranded), viruses, bacteria, cells and cell fragments, as examples. Nondegradable materials include natural or synthetic polymeric materials (e.g., polystyrene, polypropylene, polyethylene teraphthalate, polyether urethane, polyvinyl chloride, silica, polydimethyl siloxane, acrylates, arcylamides, poly(vinylpyridine), polyacroleine, polyglutaraldehyde), some polysaccharides (e.g., hydroxypropyl cellulose, cellulose derivatives, dextran®, dextrose, sucrose, ficoll®, percoll®, arabinogalactan, starch), and hydrogels (e.g., polyethylene glycol, ethylene vinyl acetate, N-isopropylacrylamide, polyamine, polyethyleneimine, poly-aluminum chloride).

In some embodiments, the particles of the present invention are produced by conventional methods known to those of ordinary skill in the art. Techniques include emulsion polymerization in a continuous aqueous phase, emulsion polymerization in continuous organic phase, interfacial polymerization, solvent deposition, solvent evaporation, dissolvation of an organic polymer solution, cross-linking of water-soluble polymers in emulsion, dissolvation of macromolecules, and carbohydrate cross-linking These fabrication methods can be performed with a wide range of polymer materials mentioned above. Examples of materials and fabrication methods for making nanoparticles have been published. (See Kreuter, J. 1991. *Nanoparticles-preparation and applications*. In: M. Donbrow Ed.): *Microcapsules and nanoparticles in medicine and pharmacy*. CRC Press, Boca Raton, Fla., pp. 125-148; Hu, Z, Gao J. Optical properties of N-isopropylacrylamide microgel spheres in water. *Langmuir* 2002; 18:1306-67; Ghezzo E, et al., Hyaluronic acid derivative microspheres as NGF delivery devices: Preparation methods and in vitro release characterization. *Int J Pharm* 1992; 87:21-29; incorporated by reference herein.)

In some embodiments, the nanoparticles and microparticles are prepared in accordance with methods disclosed in U.S. Patent Publication No. 2006/0040892, entitled Process for synthesizing oil and surfactant-free hyaluronic acid nanoparticles and microparticles; Fessi et al., *International Journal of Pharmaceutics*, 55 (1989) R1-R4; and Weng et al., *J. Biomater. Sci. Polymer Edn, Vol.* 15, No. 9, pp. 1167-1180 (2004), which are hereby incorporated by reference.

In some embodiments, the drug and/or biomolecule can either be adsorbed or absorbed to a premade nanoparticle or it can be incorporated into the nanoparticle during the manufacturing process. Methods of absorption, adsorption, and incorporation are common knowledge to those skilled in the art. In some embodiments, the choice of the monomer and/or polymer, the solvent, the emulsifier, the coating and other auxiliary substances will be dictated by the particular nanoparticle being fabricated and can be chosen, without limitation and difficulty, by those skilled in the art. The ratio of drug to particle (e.g., polymer) may be varied as appropriate for drug delivery. In addition, the removal of solvent or emulsifier may include a number of methods well known to one of ordinary skill in the art.

Hydrogel Cancer Cell Traps

In some embodiments, the cancer cell trap comprises a hydrogel. In some embodiments, the hydrogel possess controlled release properties. For example, in some embodiments, the cancer cell trap can be an in situ solidified hydrogel. In some embodiments, the cancer cell trap can be fabricated using a hydrogel base.

In some embodiments, the cancer cell trap is fabricated from a polyethylene glycol based in situ gelling hydrogel. In some embodiments, the hydrogel releases one or more chemotherapeutics. In some embodiments, the hydrogel releases one or more biomolecules.

The hydrogel may be fabricated from a material selected from the group consisting of one or more polymeric materials, polysaccharides, polyethylene glycol-poly acrylic acid interpenetrating network (PEG-PAA-IPN) hydrogel, polyethylene glycol, extracellular matrix proteins, fibrinogen, hydrogel microparticles and combinations thereof.

Various native and synthetic hydrogel and hydrogel-derived compounds are useful in the cancer cell traps of the present invention. In some embodiments, the hydrogel gel may include, but is not limited to, alginate hydrogels SAF-Gel (ConvaTec, Princeton, N.J.), Duoderm Hydroactive Gel (ConvaTec), Nu-gel (Johnson & Johnson Medical, Arlington, Tex.); Carrasyn (V) Acemannan Hydrogel (Carrington Laboratories, Inc., Irving, Tex.); glycerin gels Elta Hydrogel (Swiss-American Products, Inc., Dallas, Tex.) and K-Y Sterile (Johnson & Johnson).

Hydrogels obtained from natural sources can also be used. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof.

Synthetic hydrogels include, but are not limited to those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. In some embodiments, the hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

The hydrogel of the present invention can also be made from one or more materials capable of forming a viscous gel upon solvation. (e.g., poly lactic acids (PLA), poly lactic coglycolic acids (PLGA), collagen, hyaluronic acid (HY), alginate, chitosan, glycosaminoglycans (GAGS), etc.). Other resorbable and non-resorbable polymer materials may be suitable for practicing this invention. The appropriate polymer matrix or material to be processed in practicing the present invention may be determined by several factors including, but not limited to, the desired mechanical and material properties, the surgical application for which the material is being produced, and the desired degradation rate of the device in its final application.

The hydrogel cancer cell trap may be prepared using various known methods. For example, the hydrogel cancer cell trap can be prepared using coacervation, spray drying, or emulsion. In some embodiments, the hydrogels are prepared in accordance with the methods described in Ta et al., *Journal of Controlled Release* 126 (2008) 205-216, which is incorporated herein by reference. In some embodiments, the hydrogel cancer cell trap can be prepared using the methods described in Kuzma et al., U.S. Pat. No. 8,475,820 (Method of manufacturing an implantable device), which is incorporated herein by reference.

In some embodiments, the hydrogel comprises hyaluronic acid (HA) particles encapsulated with BSA. In some embodiments, the cancer cell trap may be comprised of uniformly sized hyaluronic acid ("HA") particles that are substantially free from oil and surfactant contaminants.

In some embodiments, the polymeric matrix of the hydrogel cancer cell trap can be hydrated prior to implantation to form the hydrogel, and the device implanted into a subject in a hydrated state. Alternatively, the implant may self-hydrate upon implantation as a dry implant, and thus, no hydration of the implant prior to implantation is necessary.

In some embodiments, the hydrogel of the present invention may be porous. For example, the pores in the hydrogel system may range in size from 10 Angstroms ($1 \times 10^{-9}$ m) to several microns. Other suitable ranges include from 50 Angstroms to 0.1 microns and from 0.1 microns to 1 micron. When the molecule for delivery is a macromolecule, the pore size is suitably over 50 Angstroms.

In some embodiments, the pores may contain diffusion enhancers. Diffusion enhancers include, but are not limited to, saline, isotonic water, and phosphate buffered saline. These pores provide larger spaces that permit the passage of macromolecular active agents into the surrounding environment.

When a hydrogel attains it maximum level of hydration, the water content of the hydrogel is referred to as "equilibrium water content" (EWC). The percent water content of the hydrogel (any state of hydration) is determined as described in U.S. Pat. No. 6,361,797. See also U.S. Pat. No. 8,475,820.

In some embodiments, a hydrogel described herein can have an EWC value in the range of from about 20% to about 90%, about 35% to about 85%, or about 50% to about 80%, as desired. In some embodiments, increases in EWC value can correspond with an increase in release rate.

Method of Treating or Preventing Cancer Metastasis

In some embodiments, the invention provides a method of treating or preventing cancer metastasis comprising administering to a subject in need thereof an effective amount of a cancer cell trap of the invention, wherein metastatic cancer cells migrate and accumulate in the cancer cell trap, thereby treating or preventing metastasis in the subject.

In some embodiments, the duration of cancer cell trap treatment should be based on the stage of the cancer metastasis. In some embodiments, the subject is treated for 1, 2, 3, 4, 5, 6, 7, 8, 9, 10, 11, or 12 months or longer. In some embodiments, additional treatments may be needed.

In some embodiments, the amount of the cancer cell traps needed for each treatment ranges from about 1 to about 500 ml(cubic centimeter)/subject. In some embodiments, the amount ranges from about 1 to about 100 ml (cubic centimeter)/subject, from about 3 to about 50 ml (cubic centimeter)/subject, and from about 5 to about 15 ml (cubic centimeter)/subject.

In some embodiments, the cancer cell trap is placed into a subject, such as by implantation or injection for a period of time. In some embodiments, the cancer cell trap is removed after a period of time. In some embodiments, the cancer cell trap is replaced with a new cancer cell trap after a period of time. In some embodiments, the cancer cell trap is removed and replaced with a new cancer cell trap every 1-2 weeks, 3 weeks 4 weeks, 5 weeks 6 weeks, 7 weeks, 8 weeks, 3 months, 4 months 5 months 6 months, or about every year.

In some embodiments, the subject is administered a single cancer cell trap. In some embodiments, more than one trap is administered to the subject. In some embodiments, about 2, 3, 4, 5, 6, 7, 8, 9, 10, 11, 12, 13, 14, 15, 16, 17, 18 19 or 20 or more cancer cell traps are administered.

In some embodiments, the cancer cell traps useful in the methods of the invention comprise one or more chemotherapeutic agents. In some embodiments, the cancer cell trap is exposed to localization radiation after a period of time following administration, allowing the recruited cancer cells to be killed and eradicated at the implant sites(s).

In some embodiments, the methods of the present invention are combined with one or more other known cancer treatments, such as radiation, surgery, chemotherapy or administration of other anti-cancer agents. In some embodiments, the cancer cell trap may be combined with a chemotherapeutic agent. For example, the cancer cell trap may release one or more chemotherapy drugs or chemotherapeutic agents.

The terms "subject", "individual" and "patient" are defined herein to include animals such as mammals, including but not limited to primates, cows, sheep, goats, horses, dogs, cats, rabbits, guinea pigs, rats, mice or other bovine, ovine, equine, canine, feline, rodent, or murine species. In some embodiments, the subject is a human.

The cancer cell trap may be administered to the subject or patient using methods known in the medical arts. In some embodiments, the cancer cell trap is implanted into the subject. In some embodiments, the cancer cell trap is injected into the subject.

Diagnosis and/or Detection of Cancer Metastasis

In some embodiments, the cancer cell trap of the present invention can be used as a diagnostic tool to evaluate the existence and/or extent of cancer metastasis in a subject. When used as a diagnostic tool, the cancer cell trap is introduced in the subject to recruit cancer cells. In some embodiments, the present invention is a method for detecting cancer metastasis comprising administering a cancer cell trap to a subject, wherein cancer cells in said subject migrate to the trap and the cancer cell is recovered and evaluated.

In some embodiments, the invention provides a method of detecting cancer metastasis, comprising administering to a subject in need thereof a cancer cell trap, wherein metastatic cancer cells migrate and accumulate in the cancer cell trap; and assaying the cancer cell trap for the presence of metastatic cancer cells, thereby detecting cancer metastasis in the subject. In some embodiments, the cancer cells are removed from the cancer cell trap or the region surrounding the trap and evaluated. In some embodiments, the cells are removed from the trap while the trap is still present in the subject. In some embodiments, the cancer cell trap is removed from the subject and the cells optionally removed from the trap before they are evaluated. The cells can be evaluated using known methods and techniques in the identification of metastatic cells, such as, for example, histological staining, polymerase chain reaction, immunocytochemistry and flow cytometry.

In some embodiments, the present invention provides a method of monitoring the effectiveness of a treatment for cancer in a subject, comprising introducing a cancer cell trap in a subject, and assaying for the presence of cancer cells over one or more periods of time.

In some embodiments, the cancer cell traps can be fabricated as a tubular structure. In some embodiments, the tubular structure has an opening on one or both sides. In some embodiments, the tubular structure has a porous structure which allows infiltration of cancer cells from the sides and the opening to the inner lumen of the cancer cell trap. In some embodiments, the cancer cells can be recovered from the inner lumen of the cancer cell trap via a needle, such as an 18-23 gauge needle.

Compositions Comprising Cancer Cell Trap

In some embodiments, the cancer cell traps of the present invention are administered to a subject as a pharmaceutical composition, which may contain salts, buffers, preservatives, or other pharmaceutical excipients.

The compositions can be formulated for parenteral, subcutaneous, intradermal, intramuscular, intraperitoneal or intravenous administration, or injectable administration. In some embodiments, suitable forms for such administration include sterile suspensions and emulsions. Such compositions can be in admixture with a suitable carrier, diluent, or excipient such as sterile water, physiological saline, glucose, and the like. In some embodiments, the compositions can also be lyophilized. The compositions can contain auxiliary substances such as wetting or emulsifying agents, pH buffering agents, gelling or viscosity enhancing additives, preservatives, and the like, depending upon the route of administration and the preparation desired. Texts, such as *Remington: The Science and Practice of Pharmacy,* Lippincott Williams & Wilkins; 20th edition (Jun. 1, 2003) and *Remington's Pharmaceutical Sciences,* Mack Pub. Co.; 18$^{th}$ and 19$^{th}$ editions (December 1985, and June 1990, respectively), incorporated herein by reference in their entirety, can be consulted to prepare suitable preparations. The presence of such additional components can influence the physical state, solubility, stability, rate of in vivo release, and rate of in vivo clearance, and are thus chosen according to the intended application, such that the characteristics of the carrier are tailored to the selected route of administration.

Suitable parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In some embodiments, the compositions for parenteral administration may be in the form of a sterile injectable preparation, such as a sterile injectable aqueous or nonaqueous solutions, suspensions, and emulsions. Examples of non-aqueous solvents are propylene glycol, polyethylene glycol, vegetable oils such as olive oil, and injectable organic esters such as ethyl oleate. Suspensions may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

In some embodiments, the compositions are preferably isotonic with the blood or other body fluid of the recipient. The isotonicity of the compositions can be attained using various excipients, such as sodium tartrate, propylene glycol or other inorganic or organic solutes. In some embodiments, sodium chloride is used. Buffering agents can be employed, such as acetic acid and salts, citric acid and salts, boric acid and salts, and phosphoric acid and salts. In some embodiments of the invention, phosphate buffered saline is used for suspension.

In some embodiments, the viscosity of the compositions can be maintained at the selected level using a pharmaceutically acceptable thickening agent. In some embodiments, methylcellulose is used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. In some embodiments, viscous compositions are prepared from solutions by the addition of such thickening agents.

In some embodiments, a pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

In some embodiments the composition is designed for immediate release of bioactive molecules and/or chemotherapeutic agents. In other embodiments the composition is designed for sustained release. In further embodiments, the composition comprises one or more immediate release surfaces and one or more sustained release surfaces.

The compositions of the present invention may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient, which would be administered to a subject, and/or a convenient fraction of such a dosage such as, for example, one-half or one-third of such a dosage.

Although the descriptions of pharmaceutical compositions provided herein are principally directed to pharmaceutical compositions, which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

The cancer cell trap may be administered to the subject or patient using methods known in the medical arts. In some embodiments, the cancer cell trap is implanted into the subject. In other embodiments, the cancer cell trap is injected into the subject. For example, the cancer cell trap may be injected intravenously, intraocularly, intravitreally, intramuscularly, intracardiacly, intraperitoneally, or subcutaneously.

Application of the teachings of the present invention to a specific problem is within the capabilities of one having ordinary skill in the art in light of the teaching contained herein. Examples of the compositions and methods of the invention appear in the following non-limiting Examples.

All publications herein are incorporated by reference to the same extent as if each individual publication or patent application was specifically and individually indicated to be incorporated by reference.

EXAMPLES

Example 1

Two Step In Vivo Model to Study Cancer Metastasis

The present investigations were aimed at the development of a reproducible animal model to investigate the processes governing inflammation-mediated cancer metastasis.

First, subcutaneous implantation of biomaterial microspheres was used to create localized inflammatory responses. This maneuver is based on extensive studies showing that the implantation of biomaterials will prompt varying levels of inflammatory responses. See e.g., Kamath S, Bhattacharyya D, Padukudru C, Timmons R B, Tang L. *J Biomed Mater Res A* 2008; 86:617-626; Nair A, Zou L, Bhattacharyya D, Timmons R B, Tang L. *Langmuir* 2008, 24:2015-2024; and Weng H, Zhou J, Tang L, Hu Z. Tissue responses to thermally-responsive hydrogel nanoparticles. *J Biomater Sci Polym Ed* 2004, 15:1167-1180.

Second, metastatic cancer cells were then injected into the peritoneal cavity, which has widely been used to study cancer migration via lymph nodes and circulation. See e.g., Carvalho M A, Zecchin K G, Seguin F, Bastos D C, Agostini M, Rangel A L, et al. *Int J Cancer* 2008; 123:2557-2565; Gerber S A, Rybalko V Y, Bigelow C E, Lugade A A, Foster T H, Frelinger J G, et al. *Am J Pathol* 2006; 169:1739-1752; and Hippo Y, Yashiro M, Ishii M, Taniguchi H, Tsutsumi S, Hirakawa K, et al. Differential gene expression profiles of scirrhous gastric cancer cells with high metastatic potential to peritoneum or lymph nodes. *Cancer Res* 2001; 61:889-895.

After cancer cell transplantation for different periods of time, lymph nodes, subcutaneous microsphere implants, and surrounding tissues were recovered for histological analyses. The numbers of cancer cells can be quantified in both lymph nodes and implantation site tissues to reflect the extent of cancer metastasis. Finally, chemokine-releasing scaffolds were fabricated to test the influence of various chemokines on promoting melanoma recruitment to scaffold implants in vivo.

Materials & Methods

Cancer Cell Culture

B16F10 melanoma cells, Lewis Lung carcinoma (LLC) cells, rat prostate cancer cell line UHU-31), human prostate adenocarcinoma (PC-3), and human breast cancer cell line (MDA-MB-231) used in this investigation were purchased from American Type Culture Collection (ATCC) (Manassas, Va., USA). B16F10 melanoma cells are skin melanoma cell line isolated from C57BL/6 J mice. LLC cells isolated from C57BL/6J mice are widely used as a model for cancer metastasis. JHU-31 cells are derived from rat and exhibit a high rate of metastasis to the lung and lymph nodes (>75%). PC-3 cells originate from a 62-year-old male Caucasian with bone metastatic prostate adenocarcinoma. MDA-MB-231 cells are derived from breast adenocarcinoma metastasized pleural effusion. All cells were maintained in DMEM supplemented with 10% heat inactivated fetal bovine serum at 37° (5% $CO_2$ humidified environment. For in vivo tracking, some of the cancer cells were labeled with Kodak X-Sight 761 Nanospheres (Carestream Health Inc., New Haven, Conn., USA) using known methods (including a method from the user manual). Nair A, Shen J, Lotfi P, Ko C Y, Zhang C C, Tang L. Biomaterial implants mediate autologous stem cell recruitment in mice. *Acta Biomater* 2011; and Thevenot P T, Nair A M, Shen J, Lotfi P, Ko C Y, Tang L. The effect of incorporation of SDF-1alpha into PLGA scaffolds on stem cell recruitment and the inflammatory response. *Biomaterials* 2010; 31:3997-4008.

Microsphere Preparation

To prompt various degrees of foreign body reactions, microspheres made of different materials, including poly-L-lactic acid (PLA), aluminum hydroxide (ALHYDROGEL® 85), glass (Glasperlen®), was used in this investigation. PLA microspheres were synthesized according to a modified precipitation method. See Weng H, Zhou J, Tang L, Hu Z. Tissue responses to thermally-responsive hydrogel nanoparticles. *J Biomater Sci Polym Ed* 2004; 15:1167-1180; Carvalho M A, Zecchin K G, Seguin F, Bastos D C, Agostini M, Rangel A L, et al. Fatty acid synthase inhibition with Orlistat promotes apoptosis and reduces cell growth and lymph node metastasis in a mouse melanoma model. *Int J Cancer* 2008; 123:2557-2565; Gerber S A, Rybalko V Y, Bigelow C E, Lugade A A, Foster T H, Frelinger J G, et al. Preferential attachment of peritoneal tumor metastases to omental immune aggregates and possible role of a unique vascular microenvironment in metastatic survival and growth. *Am J Pathol* 2006; 169:1739-1752; Hippo Y, Yashiro M, Ishii M, Taniguchi H, Tsutsumi S, Hirakawa K, et al. Differential gene expression profiles of scirrhous gastric cancer cells with high metastatic potential to peritoneum or lymph nodes. *Cancer Res* 2001; 61:889-895; Nair A, Shen J, Lotfi P, Ko C Y, Zhang C C, Tang L. Biomaterial implants mediate autologous stem cell recruitment in mice. *Acta Biomater* 2011; Thevenot P T, Nair A M, Shen J, Lotfi P, Ko C Y, Tang L. The effect of incorporation of SDF-1alpha into PLGA scaffolds on stem cell recruitment and the inflammatory response. *Biomaterials* 2010; 31:3997-4008; and Fessi H, Puisieux F, Devissaguet J P, Ammoury N, Benita S. Nanocapsules formation by interfacial polymer deposition following solvent displacement. *Int J Pharm* 1989; 55:R1-R4.

The average sizes of the microspheres were 8.23±2.12, 10, and 450-500 µm in diameter, respectively. All microspheres were sterilized with 70% ethanol and then transferred to phosphate buffered saline (PBS, 100 mM, pH 7.2) prior to experiments.

Chemokine-Releasing Scaffold Fabrication

Chemokines SDF-1α: (Prospec-Tany TechnoGene Ltd., Rehovot, Israel) and EPO (Cell Sciences, Canton, Mass., USA) releasing PLGA scaffolds were fabricated using our previously published method. Nair A, Thevenot P, Dey J, Shen J, Sun M W, Yang J, et al. Novel polymeric scaffolds using protein microbubbles as porogen and growth factor carriers. *Tissue Eng Part C Methods* 2010; 16:23-32.

Briefly, albumin microbubbles made by sonicating 10% w/v bovine serum albumin under nitrogen gas bubbling, loaded with SDF-α: (1 µg/ml) or EPO (100 IU) were added to 10% w/v PLGA solution in 1,4-dioxane. Such mixtures were frozen in liquid nitrogen and lyophilized for at least 72 h to result in the formation of 3-D degradable cancer cell traps loaded with either SDF-α or EPO.

Cancer Metastasis Animal Model

The animal experiments were carried out using C57BL/6 mice (6-10 week old) from Jackson Laboratory (Bar Harbor, Me., USA). This murine cancer metastasis model comprised of two consecutive steps. First, biomaterial microspheres (75 mg/0.5 ml saline/mouse) were implanted in the dorsal subcutaneous space of mice to elicit localized subcutaneous inflammation. Second, after microsphere implantation for different periods of time (6 hours-14 days), cancer cells (5×106 cells/0.2 ml/mouse) were transplanted in the peritoneal cavity. 24 h after tumor cell trans-plantation the animals were sacrificed. The vital organs, lymph nodes, the microsphere implants and surrounding tissues were then recovered and frozen in OCT embedding media (Polysciences Inc., Warrington, Pa., USA) at −80° C. The peripheral blood was also collected for further analysis. Eight µm thick sections were sliced using a Leica Cryostat (CM1850) and placed on poly-L-lysine coated slides for histological and immunohistochemical analyses. To reduce the extent of foreign body responses, some PLA microspheres, prior to administration were soaked with anti-inflammatory agent, dexamethasone (0.1 mg drug/0.5 ml microsphere suspension). For whole body imaging of cancer cell migration, parallel studies were carried out to monitor the migration of X-Sight 761 Nanosphere-labeled B16F10 cells in C57BL/B6 mice. The animals were then imaged using Kodak In-Vivo Imaging System FX Pro (Carestream Health Inc., New Haven, Conn., USA).

Biodistribution Analysis

To track the cell migration in animals, B16F 10 cells were transduced by Ad5 virus bearing green fluorescent protein (pEGFP-N1, Clontech Laboratories Inc., Mountain View, Calif., USA) at MOI of 50 for 24 h before injection to the peritoneal cavity. The GFP Ad5 infectivity to B16F10 was assessed by GFP expression visualized by fluorescent microscopy prior to experiments. For biodistribution analyses, GFP-B16F10 (1.0×107) suspended in the culture medium (0.2 ml) were injected into the peritonea of C57BL/6 mice as described before. After sacrificing the animals, the tissue sections were analyzed under fluorescent microscope. Cancer cell densities in different tissues were quantified to reflect the degree of cancer metastasis. In some studies, biodistribution analyses can also be done using FITC-labeled cancer cells and ex vivo organ imaging method. At the end of study, all organs were isolated from the animals and the distribution of cancer cells in various organs was determined using Kodak In-Vivo Imaging Systems.

Influence of Chemokine Inhibitors and Neutralizing Antibodies in Cancer Cell Migration.

To determine the role of CXCR4/SDF-1α: and CCR7/CCL21 pathways in cancer metastasis, AMD3100 and CCL21 neutralizing antibodies were used to block CXCR4/SDF-1α and CCR7/CCL21 pathways, respectively. Specifically, microsphere-implanted animals were injected intraperitoneally with either AMD3100 (250 µg/0.1 ml/mouse, Sigma-Aldrich Inc., St. Louis, Mo., USA) or CCL21 neutralizing antibody (1 mg/0.1 ml/mouse: R&D Systems Inc., Minneapolis, Minn., USA) 1 h prior and 12 h post tumor injection.

Histological Quantification of Inflammatory Responses and Cancer Cell Migration.

Immunohistological analyses for CD11b+ inflammatory cells and HMB45+ melanoma cells were carried out to assess the degree of implant-mediated inflammatory responses and melanoma cell migration, respectively. Briefly, tissue sections were incubated with the primary anti-melanoma antibody (HMB45, 1:50 dilution, Abeam, Cambridge, Mass., USA) or anti-mouse CD11b antibody (1:20 dilution, Serotec Inc., Raleigh, N.C., USA) for 1 h at 37° C. After washing thrice with PBS, the slides were then incubated with either HRP-conjugated or FITC-conjugated secondary antibody (1:500 dilution, Jackson ImmunoResearch Laboratories, West Grove, Pa., USA) for 1 h at 37° C. FITC-conjugated antibody incubated tissue section was ready for image analysis. HRP-conjugated antibody incubated sections were developed with a DAB liquid Substrate System for 15 min. All tissue section images were taken using a Leica fluorescence microscope (Leica Microsystems GmbH, Wetzlar, Germany) equipped with a Retiga-EXi CCD camera (QImaging, Surrey, BC, Canada) as described earlier. Nair A, Shen J, Lotfi P, Ko C Y, Zhang C C, Tang L. Biomaterial implants mediate autologous stem cell recruitment in mice. *Acta Biomater* 2011; Thevenot P T, Nair A M, Shen J, Lotfi P, Ko C Y, Tang L. The effect of incorporation of SDF-1alpha into PLGA scaffolds on stem cell recruitment and the inflammatory response. *Biomaterials* 2010; 31:3997-4008; and Nair A, Thevenot P, Dey J, Shen J, Sun M W, Yang J, et al. Novel polymeric scaffolds using protein microbubbles as porogen and growth factor carriers. *Tissue Eng Part C Methods* 2010; 16:23-32.

Statistical Analyses

Statistical comparison between different groups was carried out using Student t-test or one-way ANOVA. Differences were considered statistically significant when $p<0.05$.

Recruitment of Cancer Cells Toward Biomaterial Implants

Biomaterial-mediated inflammatory responses involve a series of processes with the participation of various immune cells and inflammatory cytokines/chemokines. It was found that 1-day old subcutaneous implants attract the infiltration of inflammatory cells (CD11b+) and intraperitoneally transplanted B16F10 melanoma cells (HMB45+) (FIG. 1A). The immigration of melanoma cells into distant inflammatory sites suggests that inflammatory signals may serve as chemoattractants for melanoma cells. To test this, the influence of varying degrees of inflammatory responses on melanoma cell migration was analyzed. To create a localized environment with varying inflammatory intensities, poly-L-lactic acid (PLA) microspheres were implanted in the subcutaneous space for different periods of time (6 h, 12 h, 24 h, 2 days, 7 days and 14 days) (FIG. 1B). As expected, most of the inflammatory cell (CD11b+) recruitment occurs within 12 h following microsphere implantation with insignificant increase after 24 h (FIG. 1C). To determine the importance of stage and intensity of the inflammatory processes in cancer cell migration, B16F10 melanoma cells were transplanted in the peritonea of mice bearing subcutaneous microsphere implants for different periods of time. At various time points following the initiation of inflammation, the numbers of melanoma cells immigrating into subcutaneous microsphere implantation sites were analyzed (FIGS. 1D and E). Interestingly, it was found that the numbers of recruited melanoma cells varied greatly in mice bearing implants for different periods of time (FIGS. 1D and E). The accumulation of melanoma cells appears to be responding to acute inflammatory responses triggered by microsphere implantation for 12 h up to 7 days. However, only a few melanoma cells were recruited to the sites with microspheres implanted for less than 6 h and longer than 2 weeks (FIG. 1D). The specificity of the inflammatory response-mediated cancer metastasis could also be demonstrated by an optical imaging method using B16F10 melanoma cells labeled with near-infrared Kodak X-Sight 761 Nanospheres. The in vivo image shows that transplanted melanoma cells were only recruited to the dorsal skin site with microsphere implants (FIG. 1F).

Effect of Inflammation-Suppression on Cancer Cell Immigration

Figure 2:
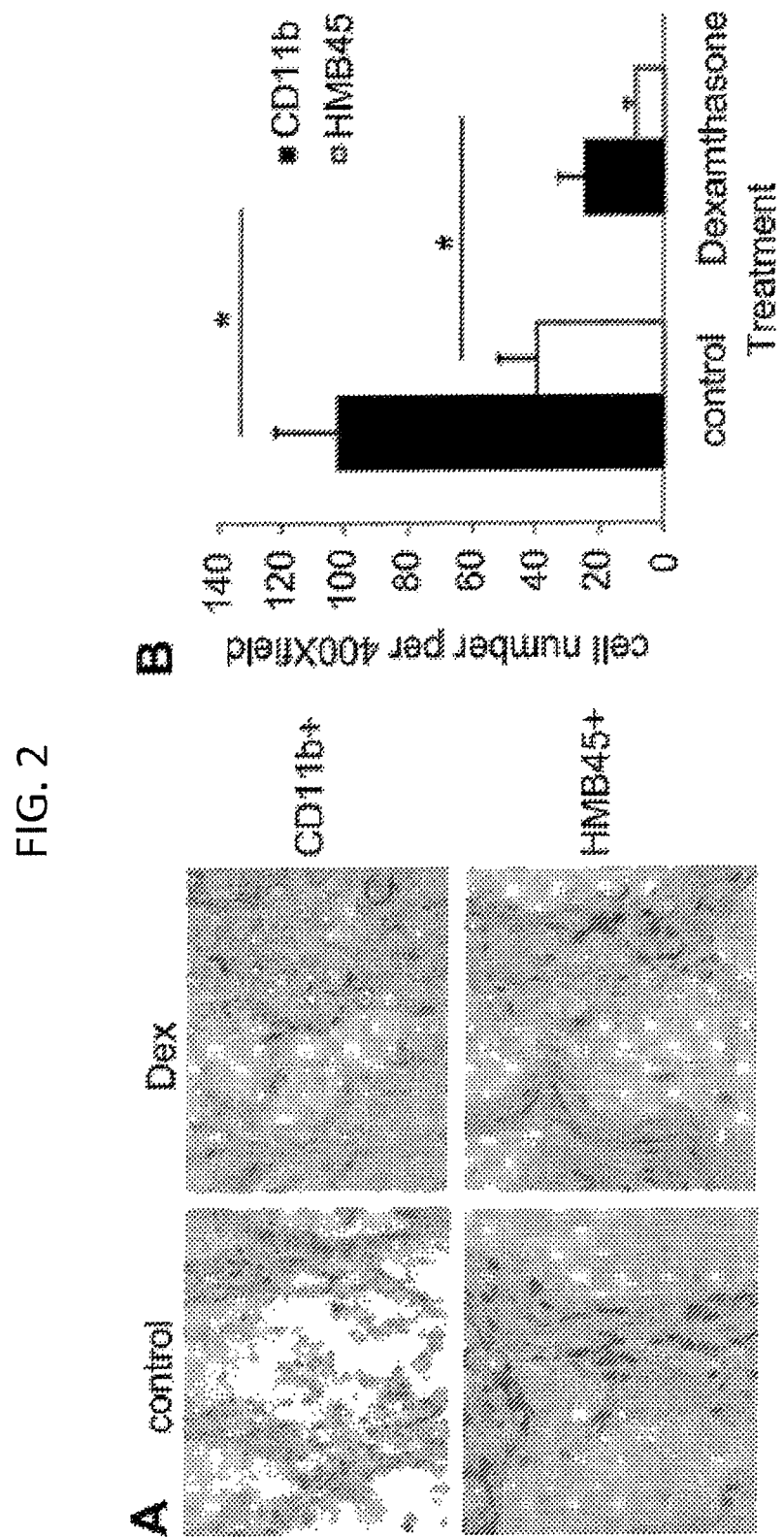
FIG. 2. Immunohistochemical staining of subcutaneous tissues surrounding the PLA microspheres with or without the treatment of dexamethasone (Dex). The accumulation of inflammatory cell (CD11b.) in tissue implanted with PLA microspheres (A, top left) or PLA microspheres soaked with dexamethasone (A, top right) can be observed (200×). The recruitment of melanoma cells (HMB45.) was also observed in tissues implanted with PLA microspheres (A, bottom left) or dexamethansone embedded PLA microspheres (A, bottom right) (400×). Quantification of the numbers of inflammatory cells and melanoma cells in the subcutaneous tissues with both treatments were graphed and statistically analyzed (B). Data are mean±SD (n. 6 per group). *P<0.05, t-test.

To verify the importance of inflammatory reactions in triggering melanoma cell immigration, similar subcutaneous PLA microsphere implantations were carried out in the presence or absence of the anti-inflammatory agent, dexamethasone. As expected, dexamethasone-treated microspheres prompted substantially less inflammatory cell (CD11b+) recruitment than saline-incubated microsphere controls (FIG. 2A, panel of photos: CD11b+ vs. HMB45+, dexamethasone-treated vs. controls). Coincidentally, the recruitment of melanoma cells (HMB45+) was also diminished by localized release of dexamethasone (FIG. 2A). The effects of locally released dexamethasone on the reduction of inflammatory cell and melanoma cells are statistically significant (FIG. 2B). These results provide strong support to the idea that inflammatory reactions are essential for the initiation of cancer cell migration from the peritoneal cavity to subcutaneous microsphere implantation sites.

Effect of Biomaterial Properties on Cancer Cell Recruitment.

Figure 3:
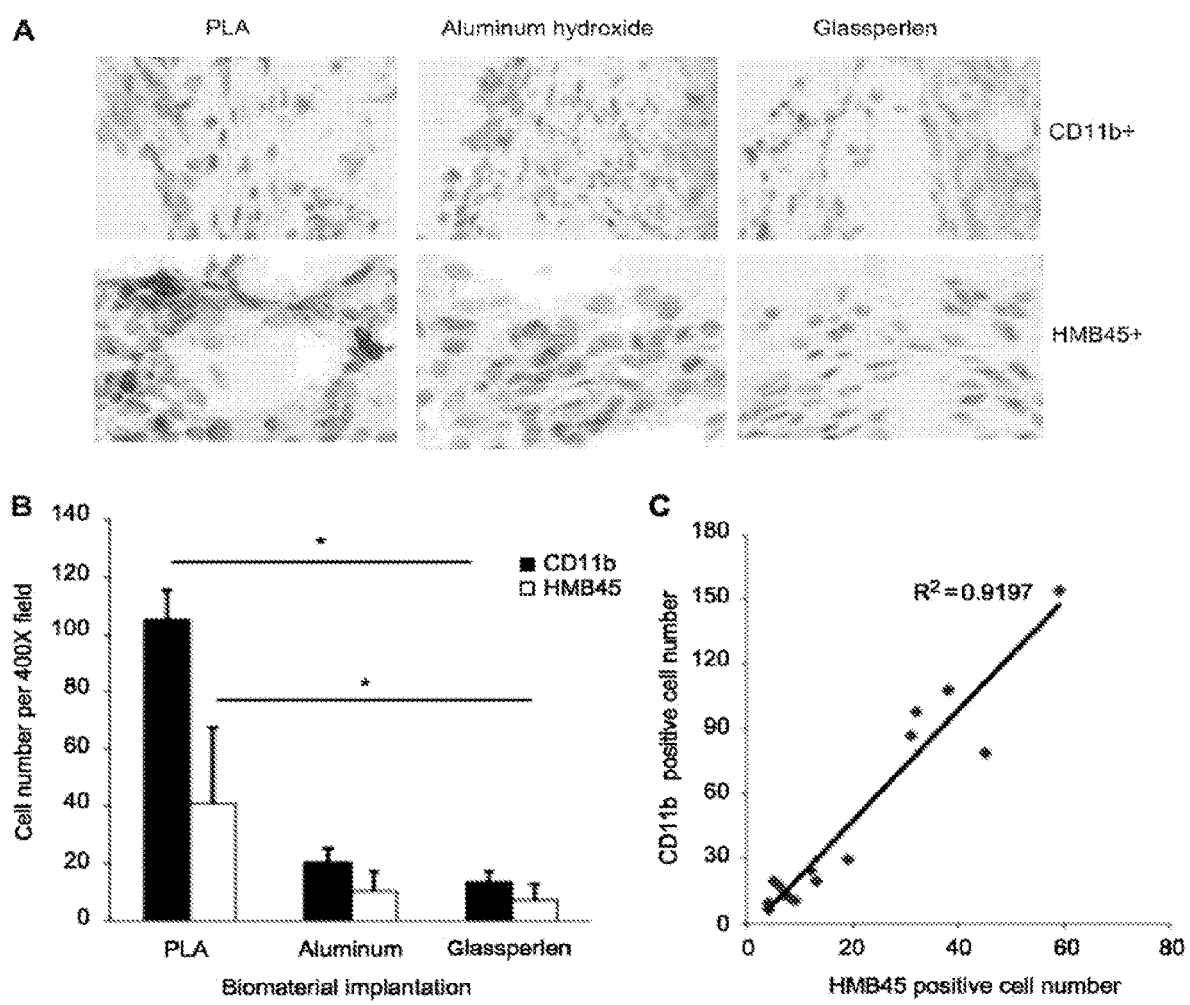
FIG. 3. Extent of foreign body responses and melanoma cell recruitment to different biomaterial implants. Immunohistochemistry staining of the tissue was carried out to assess the degree of foreign body reactions and quantify the accumulation of CD11b. inflammatory cells and HMB45. melanoma cells surround the implants, including PLA, aluminum hydroxide and Glasperlen (A). The quantification analysis of cell recruitment was graphed (B) and the correlation between the melanoma cell numbers and inflammatory cell numbers in surrounding tissue of implanted microspheres statistically analyzed (C). Data are mean±SD (n. 5 per group). *P<0.05, ANOVA.

It is well established that different materials trigger varying degrees of inflammatory responses. If the extent of biomaterial-mediated inflammatory responses affects the degree of cancer cell immigration, materials with different tissue compatibility might differentially influence melanoma cell recruitment. To test this hypothesis, microspheres made of PLA, aluminum hydroxide, and glass were tested using the same animal model. As expected, these implanted microspheres triggered different extent of inflammatory responses and melanoma cell immigration as shown by immunohistochemical analysis (FIG. 3A). PLA microspheres were found to prompt more inflammatory cell (CD11b+) and melanoma cell (HMB45+) recruitment than microspheres made of aluminum hydroxide and glass (FIG. 3B). By comparing the numbers of both cell types, our results showed that there is an excellent correlation ($R2=0.9197$) between the extent of inflammatory reactions and melanoma cell recruitment (FIG. 3C). These results lend strong support to our hypothesis that inflammatory responses influence the migration and, perhaps, metastatic behavior of melanoma cells.

Assessment of Cancer Cell Biodistribution

Figure 4:
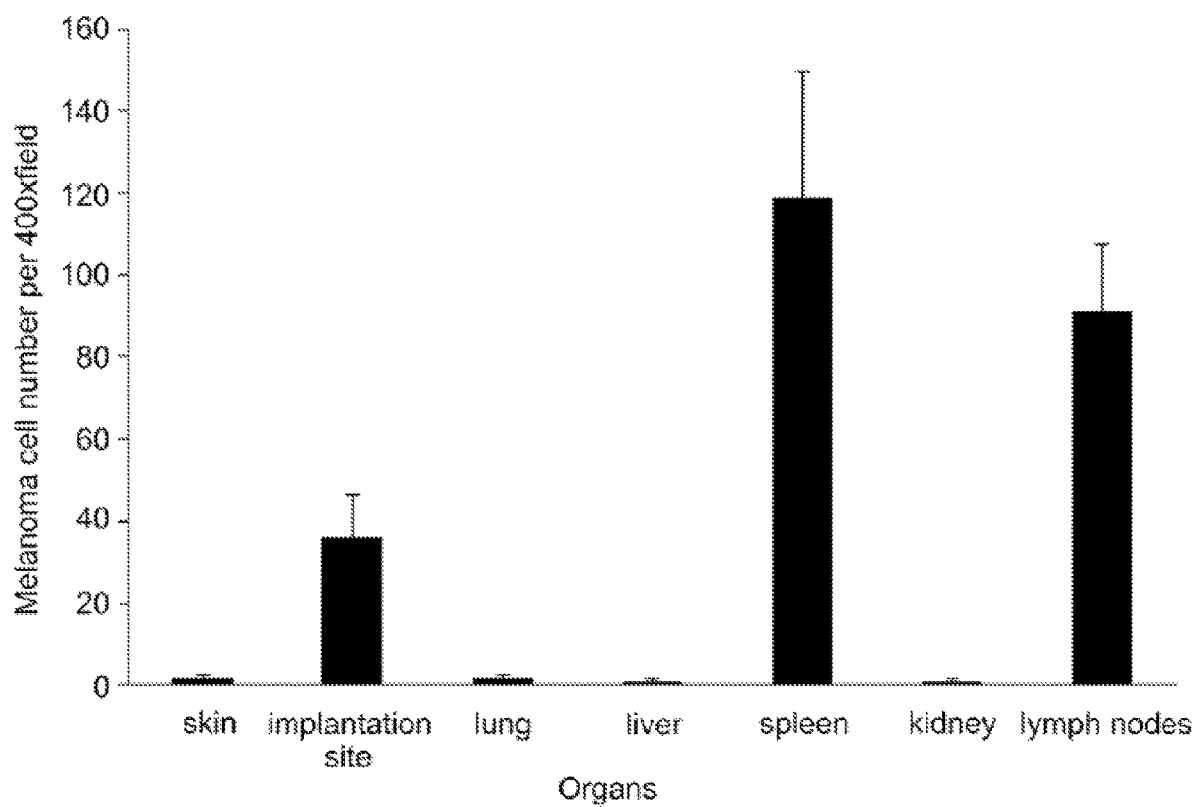
FIG. 4. Biodistribution evaluation of B16F10 cell recruitment to the microsphere implant area based on immunohistological analyses. To observe the biodistribution, GFP-expressing B16F 10 cells were administered intraperitoneally 24 h following PLA microsphere implantation. High densities of cancer cells were found in the lymph nodes, spleen and implantation area. However, relatively low densities of cancer cells were found in skin, lung, liver, and kidney.

Although our histological results support the idea that localized inflammatory responses attract melanoma cell immigration from the peritoneal cavity to the subcutaneous implantation site, it is not clear whether the inflamed tissue/microsphere implantation site is the only target for the migrating melanoma cells. The overall distribution of GFP-expressing B16F10 melanoma cells in major organs (including lung, liver, kidney, spleen, and lymph nodes) was assessed using histological analyses. In addition to the subcutaneous implantation site, high numbers of cancer cells were found in the lymph nodes and spleen. However, relatively low densities of cancer cells were found in skin, lung, liver, and kidney (FIG. 4). The accumulation of melanoma cells in the spleen may be associated with its blood filter activities. The accumulation of large numbers of cancer cells in the lymph nodes suggests that melanoma cell migration from peritoneum to the blood might involve passage through the lymphatic system.

Inflammatory responses have been implicated in the process of metastasis of various cancers. Ikebe M, Kitaura Y, Nakamura M, Tanaka H, Yamasaki A, Nagai S, et al. Lipopolysaccharide (LPS) increases the invasive ability of pancreatic cancer cells through the TLR4/MyD88 signaling pathway. *J Surg Oncol* 2009; 100:725-731; and Koller F L, Hwang D G, Dozier E A, Fingleton B. Epithelial interleukin-4 receptor expression promotes colon tumor growth. *Carcinogenesis* 2010; 31:1010-1017.

Figure 5:
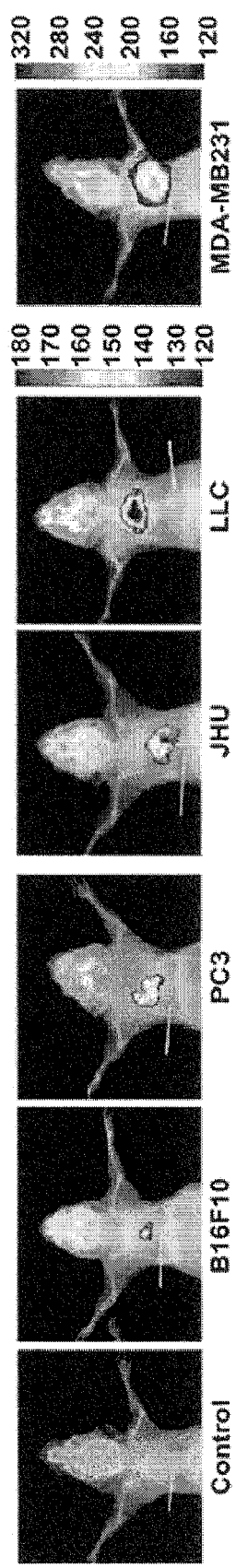
FIG. 5. Cancer cell recruitment in response to inflammatory stimulus is universal in different cancer cell types, including Lewis lung cancer (LLC), human MDA-MB-231 breast cancer, human PC-3 prostate cancer, JHU-31 rat prostate cancer. Animal bearing PLA implant transplanted with non-labeled cancer cells served as control FIG. 6. AMD3100 treatment inhibited the cell recruitment of B16F10 melanoma to the implant site (A). However, AMD3100 blockage exerted no effect on the accumulation of melanoma cells in lymph node (B). On the other hand, CCR7/CCL21 pathway in B16F 10 melanoma cell accumulation in the inflamed sites was also examined by CCL21 neutralizing antibody treatments. In contrast, the number of tumor cells migration to microsphere implantation site was not affected (C). However, the presence of B16F10 melanoma cells in the lymph node drastically diminished (D). *P<0.05, t-test.

Although our results so far support the hypothesis that inflammation will cause B16F10 melanoma cells to accumulate in the inflamed area, it was not clear whether other types of cancer cells might respond similarly. By labeling several cancer cells (Lewis lung cancer, human MDA-MB-231 breast cancer, human PC-3 prostate cancer, rat JHU-31 prostate cancer), originating from different sources, with a NIR probe, the same animal model was tested. Interestingly, it was found that all cancer cells tested here migrated to the subcutaneous implantation sites, although the extent of cancer cell migration varied between the cell types (FIG. 5).

Molecular Pathway Associated with Inflammation-Mediated Cancer Migration

Despite of the above observations on the recruitment of cancer cells to microsphere implantation sites, it was still not clear whether this animal model might reflect cellular and physiological responses resembling other earlier cancer metastasis models. To test the relevance of this model, the molecular processes governing the foreign body reaction-mediated cancer migration was first identified. Since both CXCR4/CXCL12 and CCR7/CCL21 pathways have been shown to play an important role in melanoma cancer metastasis, the potential role of both pathways in foreign body reaction-mediated cancer migration was assessed.

Figure 6:
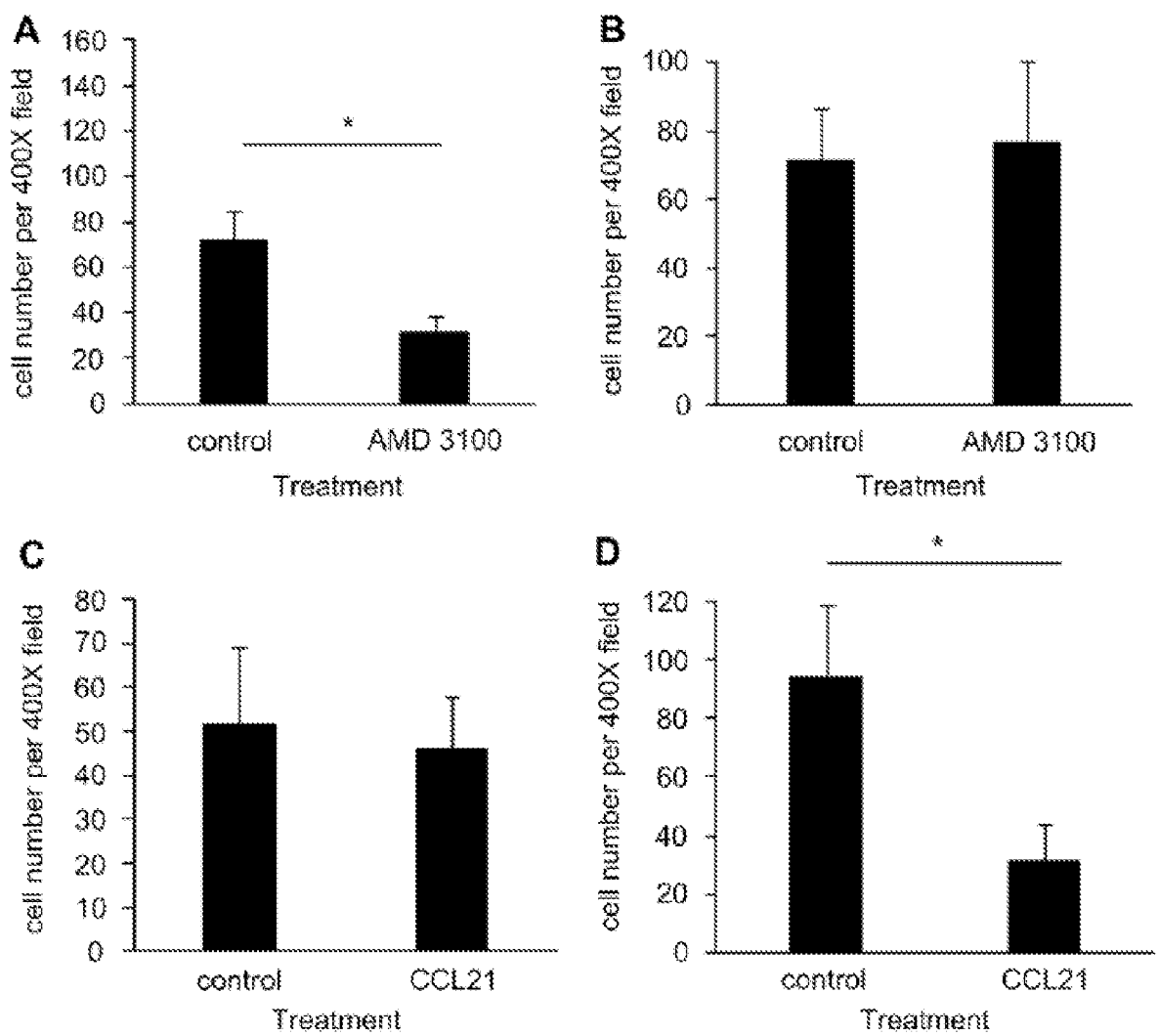

It was first tested whether CXCR4/CXCL12 pathway was involved in our animal model. Indeed, treatment with AMD3100, an antagonist of the SDF-1α receptor-CXCR4, drastically reduced the recruitment of both melanoma cells and inflammatory cells to the subcutaneous microsphere implantation sites (FIG. 6A). On the other hand, AMD3100 treatment had no effect on the accumulation of melanoma cells in lymph nodes (FIG. 6B). To test the importance of CCR7/CCL21 pathway in B16F10 melanoma cell accumulation in the inflamed sites, microsphere-bearing mice were treated with either CCL21 neutralizing antibody or saline prior to melanoma cell trans-plantation. It was observed that the number of tumor cells migrating to the microsphere implantation site was not affected by the treatment with CCL21 neutralizing antibody (FIG. 6C). On the other hand, CCL21 neutralizing antibody treatment dramatically diminished the presence of B16F10 melanoma cells in the lymph nodes (FIG. 6D). These results show that CCR7/CCL21 pathway, but not CXCR4/CXCL12 pathway, is critical to melanoma migration through lymphatic system. On the other hand, CXCR4/CXCL12 pathway, but not CCR7/CCL21 pathway, is essential to cell immigration into the subcutaneous implantation site.

Application of Chemokine-Releasing Scaffolds to Enhance Cancer Cell Recruitment

Previous results support that implant-associated inflammatory products actively recruit circulating cancer cells. The next question is whether cancer cell recruitment can be enhanced by cancer cell migration-specific chemokines. To find the answer, I was interested in SDF-1α and EPO, since both of these chemokines have been shown to enhance cancer cell migration and are also upregulated on metastatic cancer cells. Gomperts B N, Strider R M. Chemokine-directed metastasis. Contrib Microbiol 2006; 13:170-190; and Lugade, A. A., et al., J Immunol, 2005. 174(12): p. 7516-23.

Figure 7A:
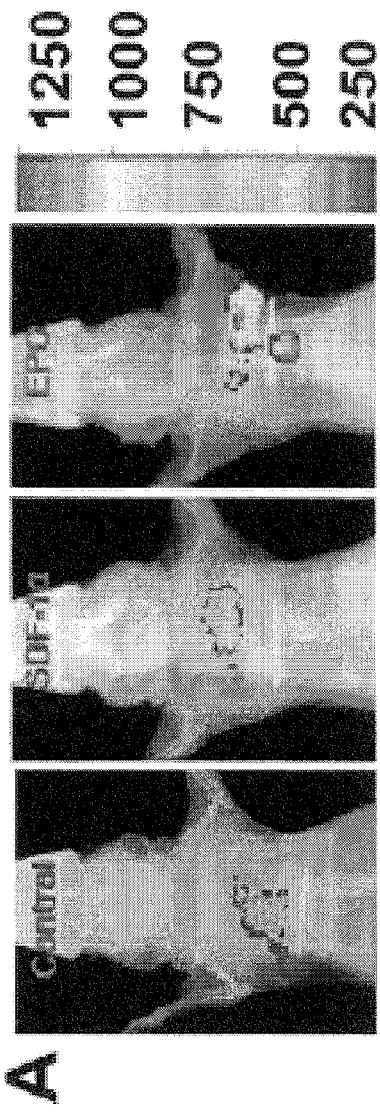
FIG. 7. (A). EPO and SDF-1α loaded tissue scaffold along with control scaffolds were tested for their melanoma recruitment ability using a murine melanoma metastasis model. Real time in vivo imaging showed accumulation of labeled B16F10 melanoma cells around the tissue scaffolds. (B). EPO and SDF-1α loaded tissue scaffold along with control scaffolds were tested for their melanoma recruitment ability using a murine melanoma metastasis model. EPO-releasing tissue scaffolds showed enhanced >1 fold accumulation of melanoma cells detected using Kodak imaging system. (C) EPO releasing scaffolds significantly enhanced the life span of cancer bearing animals. *P<0.05, t-test.
Figure 8:
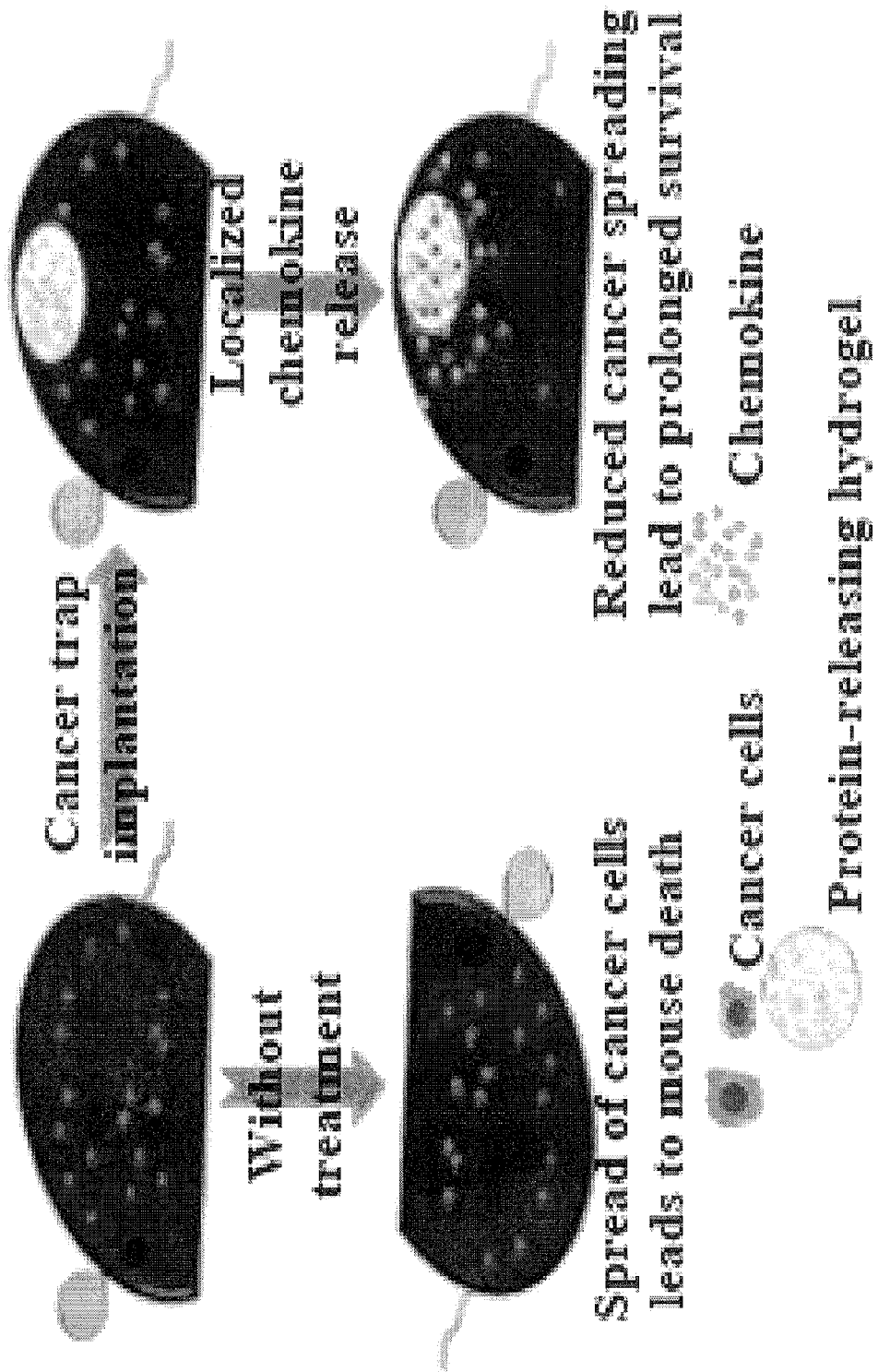
FIG. 8. Metastatic cancer cell trap using chemokine-releasing hydrogel.
Figure 9:
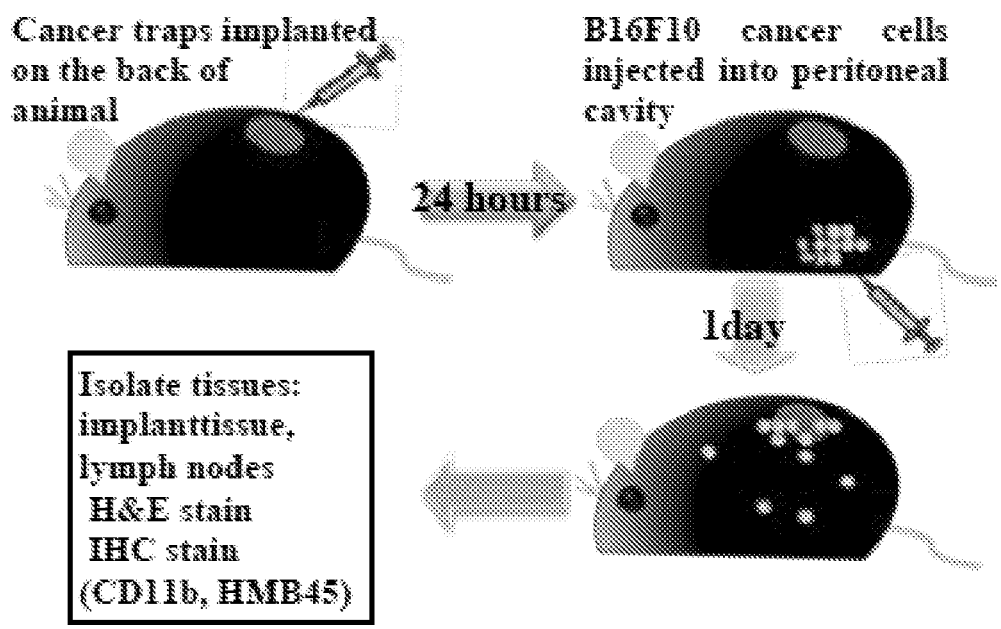
FIG. 9. Schematic illustration of the cancer metastasis animal model.

To test this hypothesis, SDF-1-releasing scaffolds and EPO-releasing scaffolds were fabricated. Our results have shown that these scaffolds are capable of releasing 10% of the loaded drug for duration of approximately 10 days. When implanted subcutaneously in mice and followed with NIR-labeled B16F10 melanoma cell transplantation, it was found that the localized release of EPO prompted the highest cancer cell recruitment, as compared to SDF-1α; which was not significantly different from the control (FIGS. 7A&B). The survival duration of scaffold-bearing animals was also evaluated after completion of the in vivo imaging detection. Very interestingly, it was found that the release of EPO significantly prolonged the survival (>30%) of the cancer bearing mice as compared to SDF-1α; loaded scaffolds (FIG. 7C).

Example 2

Efficacy of Cancer Cell Traps in Treating Various Metastatic Cancers

Leukemia Cancer

Figure 14B:
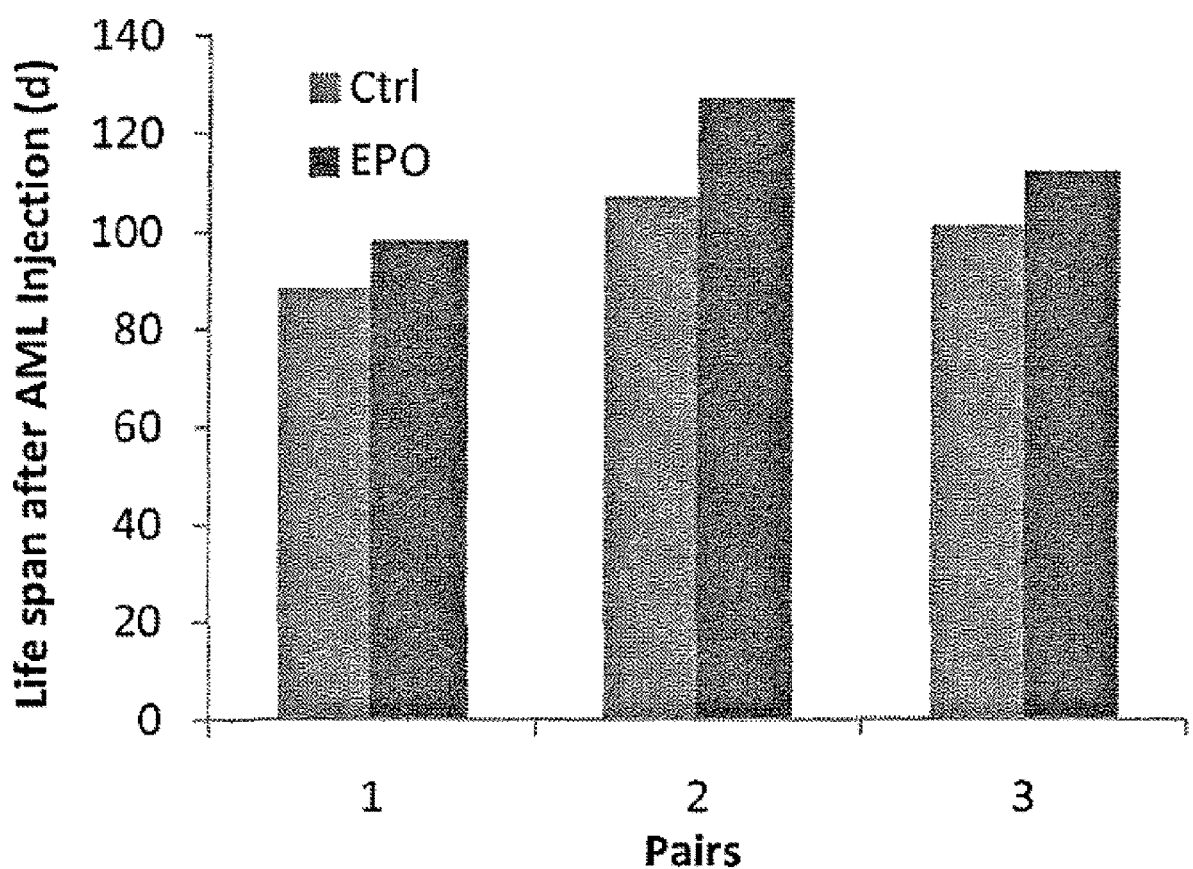
FIG. 14. Effect of Cancer cell traps On Leukemia Cancer Cells. (A) Mice infected with leukemia cancer were implanted with either EPO releasing scaffolds or control scaffold (no EPO). After implantation of the cancer cell traps, the numbers of leukemia cells in the blood in both groups of animals was monitored. It was found that while leukemia cell numbers increased with time, the leukemia cell number increase was substantially slowed down. These results are demonstrated in chart (A). With the release of EPO, it was found that leukemia transplanted mice survival was around ~90 days. However, cancer cell traps (EPO-releasing) had ~20% increase of survival duration as shown in the following chart (B).

Using AML cell line, the effectiveness of cancer cell traps to treat leukemia was tested. Mice were induced with leukemia with AML cell line injection. After implanted for different periods of time to achieve 40% leukemia cells in circulation, the animals were then implanted with either EPO releasing scaffolds or control scaffold (no EPO). The numbers of leukemia cells in the blood in both groups of animals was then monitored. It was found that leukemia cell numbers increased with time. On the other hand, the leukemia cell number increase was substantially slow down as shown in FIG. 14.

With the release of EPO, it was found that leukemia transplanted mice survival around 90 days. However, cancer cell traps (EPO-releasing) have 20% increase of survival duration as shown in FIG. 14.

Melanoma Cancer

Using near-infrared labeled B16FIO melanoma cell transplanted mice; the effect of cancer cell traps in reducing cancer metastasis was studied. Specifically, PEG hydrogel was used as the carrier of the cancer cell traps. PEG hydrogel was mixed with RANTES (100 ng/ml), IL8 (10 ng/ml) or saline (as control). C57 mice were transplanted intravenously with melanoma cells (107/mouse) and followed with subcutaneous injection of I ml of cancer cell trap gel. After implantation for 24 hours, it was found that there are substantially more melanoma cells were recruited to the cancer cell traps releasing either RANTES or IL-8 than control as shown in FIG. 15. In addition, by compared with control, the numbers of melanoma cells in the peripheral blood were reduced 76% or 82% in mice bearing RANTES or IL-8 releasing hydrogel, respectively.

The survival duration of various treated animals was also monitored. It was found that RANTES-releasing and IL-8-releasing hydrogel implants substantially increase the lifespan of animals for >20% by compared with controls (see FIG. 15).

Prostate Cancer

Using near-infrared labeled PC-3 prostate cancer cell (107/animal) intraperitoneally transplanted mice, the efficacy of various cancer cell traps in reducing prostate cancer metastasis was determined. For that, tissue scaffolds capable of releasing either VEGF (50 ng/implant) or EPO (1,000 ID/implant) were fabricated. These cancer cell traps were implanted in the peritonea of cancer-bearing mice. The extent of cancer cell recruitment using Kodak in vivo imaging system was monitored. After implantation for 24 hours, there was substantially more prostate cancer cells were recruited to the cancer cell traps releasing either VEGF or EPO than control as shown in FIG. 16. Furthermore, the numbers of prostate cancer in the peritoneal lavage fluids was also measured. It was found that, compared with control, the numbers of prostate cancers in the peritonea fluids were reduced 86% or 91% in mice bearing VEGF-releasing or EPO-releasing scaffolds, respectively.

The survival duration of various treated animals was also monitored. It was found that VEGF-releasing and EPO-releasing implants substantially increase the lifespan of animals for >25% by compared with controls (see FIG. 16).

Example 3

Fabrication of Protein-Releasing Degradable Tissue Scaffolds

Although physical adsorption has been used in many studies to create growth factor releasing scaffolds, such methods only permit the release of growth factors for 1-2 days. To improve release duration, chemical conjugation processes have been developed to produce growth factor-coated scaffolds. Unfortunately, such chemical reactions often alter the scaffold material properties and bioactivity of incorporated protein and require additional complex chemical reactions. To overcome such deficiencies, a novel two-step porous scaffold fabrication procedure has been created in which albumin micro bubbles (MB) were used as a porogen (FIG. 10A) and growth factor carrier. Nair, A., et al., *Novel polymeric scaffolds using protein microbubbles as porogen and growth factor carriers*. Tissue Eng Part C Methods, 2010. 16(1): p. 23-32.

Figure 10D:
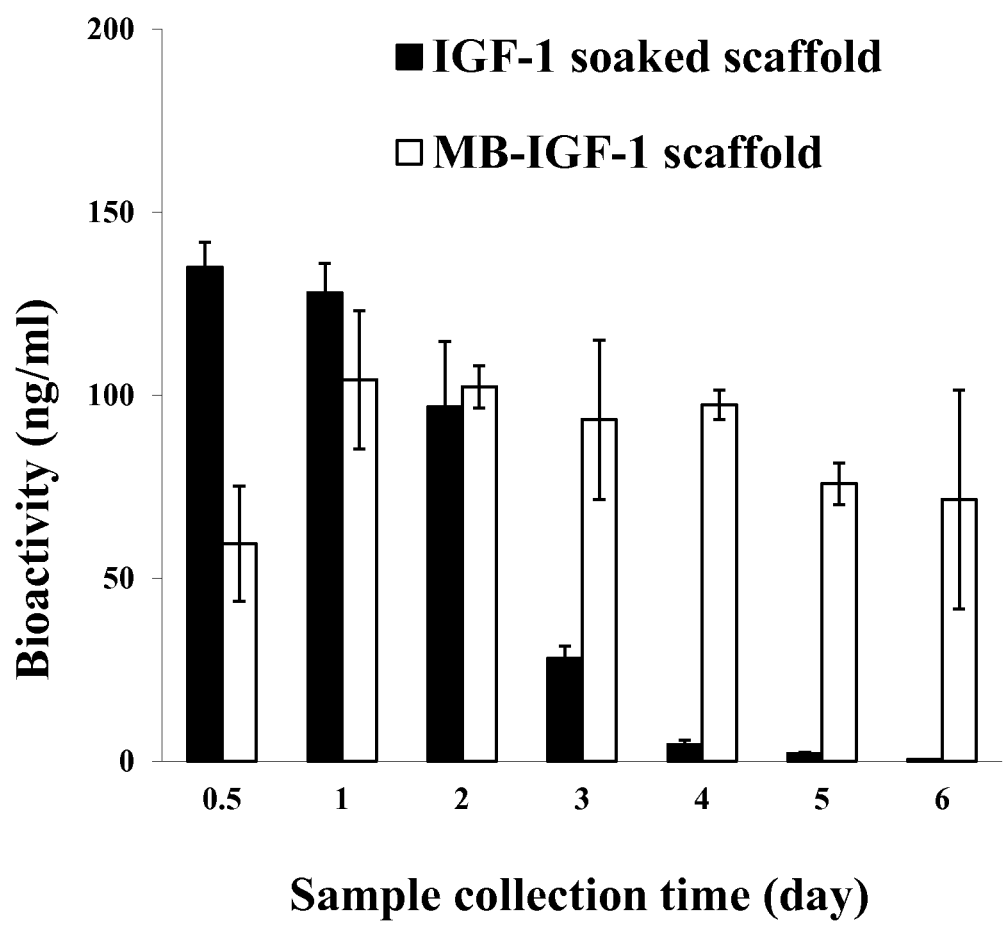
FIG. 10. (A). BSA microbubbles (MB) used as porogens to fabricate PLGA scaffolds. Microbubble image under a light microscope. (B) SEM image of BSA MB scaffolds showed large pores and honeycomb like pore wall structure. (C) Prominent blue protein stains were found in almost all walls of the large pores in BSA MB scaffold. (D) The bioactivity of IGF-1 released at various time points from MB-IGF-1 scaffolds and IGF-1 soaked scaffolds.

First MB embedded scaffolds showed pore sizes ranging from 100 to 150 μm with an interconnected matrix (FIG. 10A). Also, protein deposition was observed along the pores as indicated by commassie blue protein stain, which implies that MBs were responsible for the large pore sizes (FIG. 10B). It was then tested whether MBs could protect the growth factors from solvent inactivation during scaffold fabrication processes. For that, insulin-like growth factor-1 (IGF-1), a potent stimulator of collagen production, was chosen as model chemokine Indeed, MBs were able to protect the bioactivity of the growth factor even after exposure to organic solvents often used in scaffold fabrication. These IGF-1 loaded MBs were incorporated in PLGA scaffolds and release studies were conducted. IGF-1 released from MB scaffolds was three times more bioactive than IGF-1 soaked control scaffolds (FIG. 10B).

Example 4

Development of Injectable Cancer Cell Trap

Figure 11A:
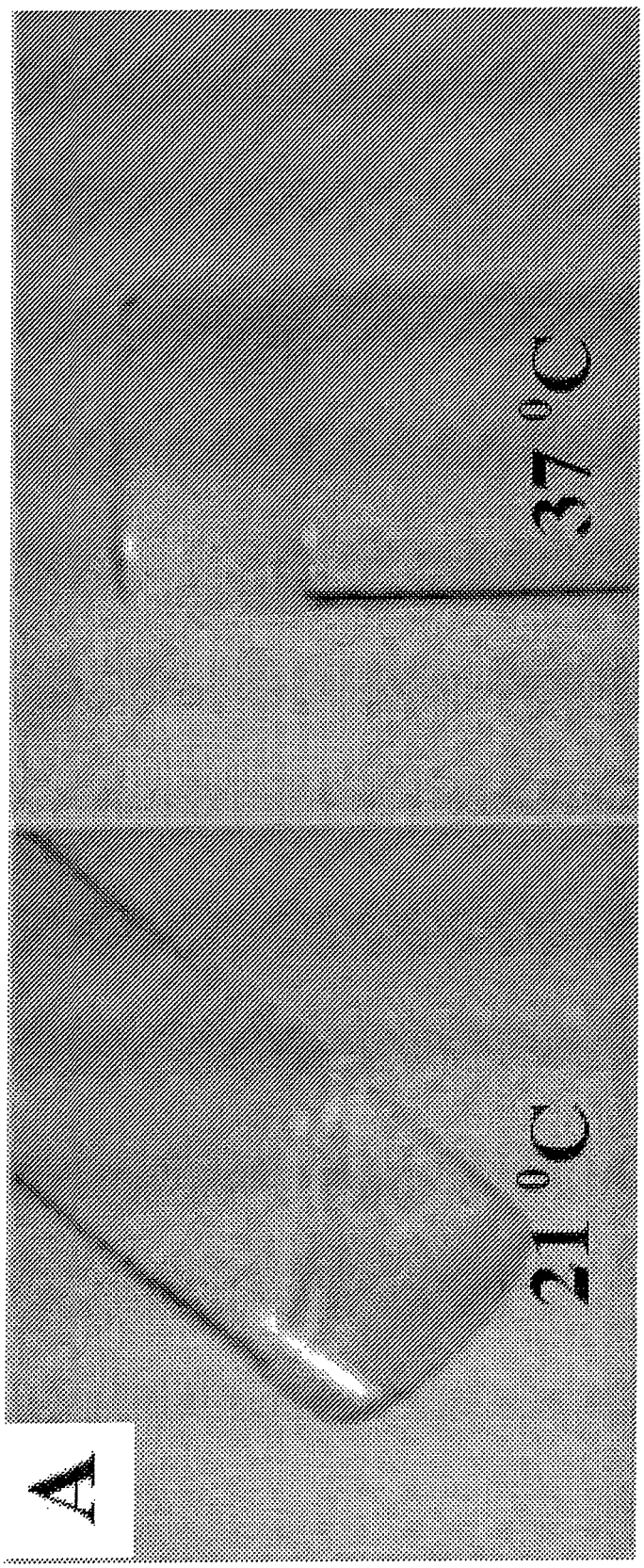
FIG. 11. (A). PEG-based hydrogel for controlled protein release. The fluid phase of hydrogel at room temperature becomes solid at 37° C. (B) PEG-based hydrogel for controlled protein release. Imaging of in vivo release of NIR-labeled BSA from various concentrations of hydrogel (0, 3, vs. 5%) with time. (C) PEG-based hydrogel for controlled protein release. The quantitative results show the controlled slow release properties of PEGd hydrogel.
Figure 11B:
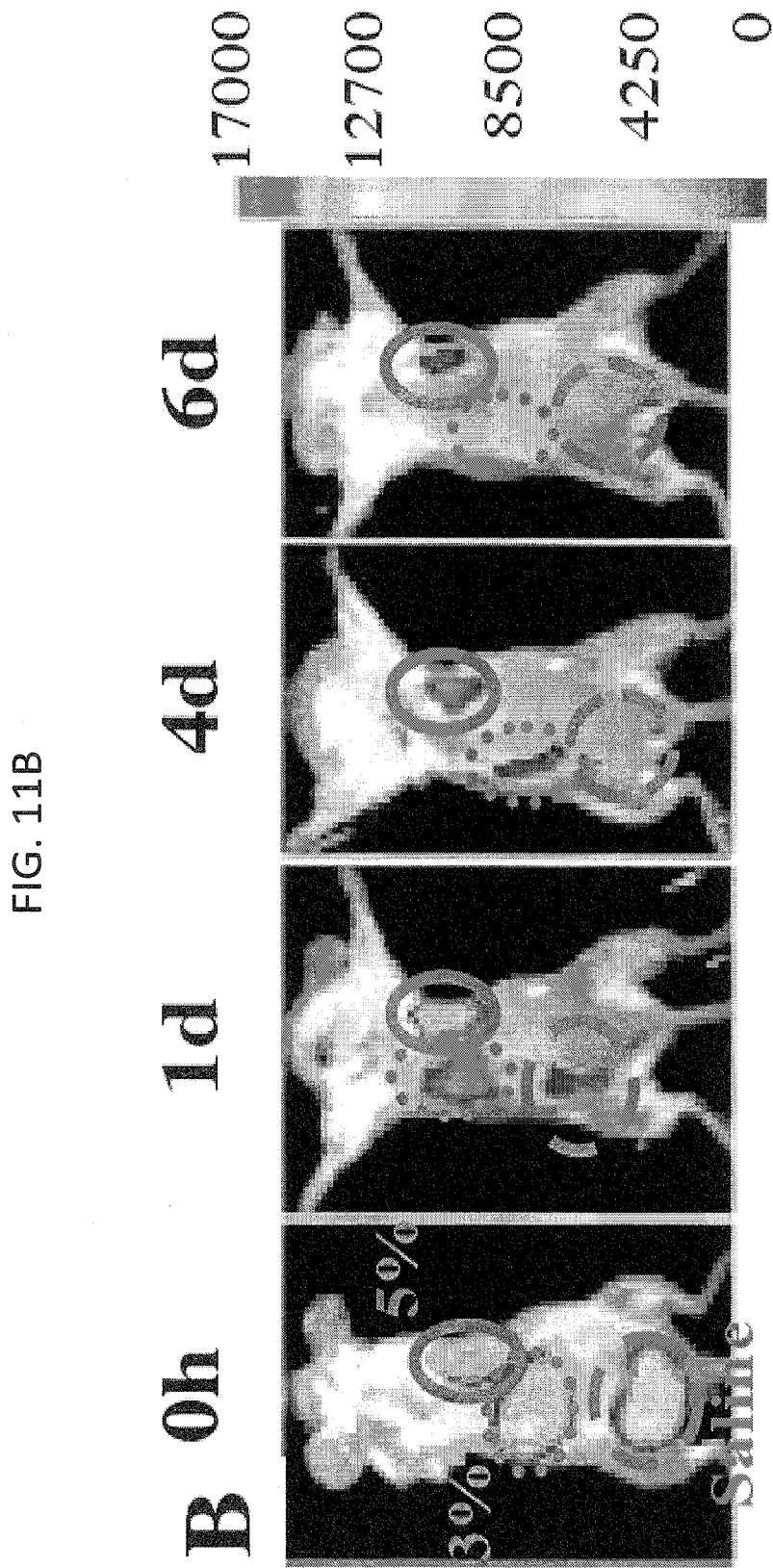
Figure 11C:
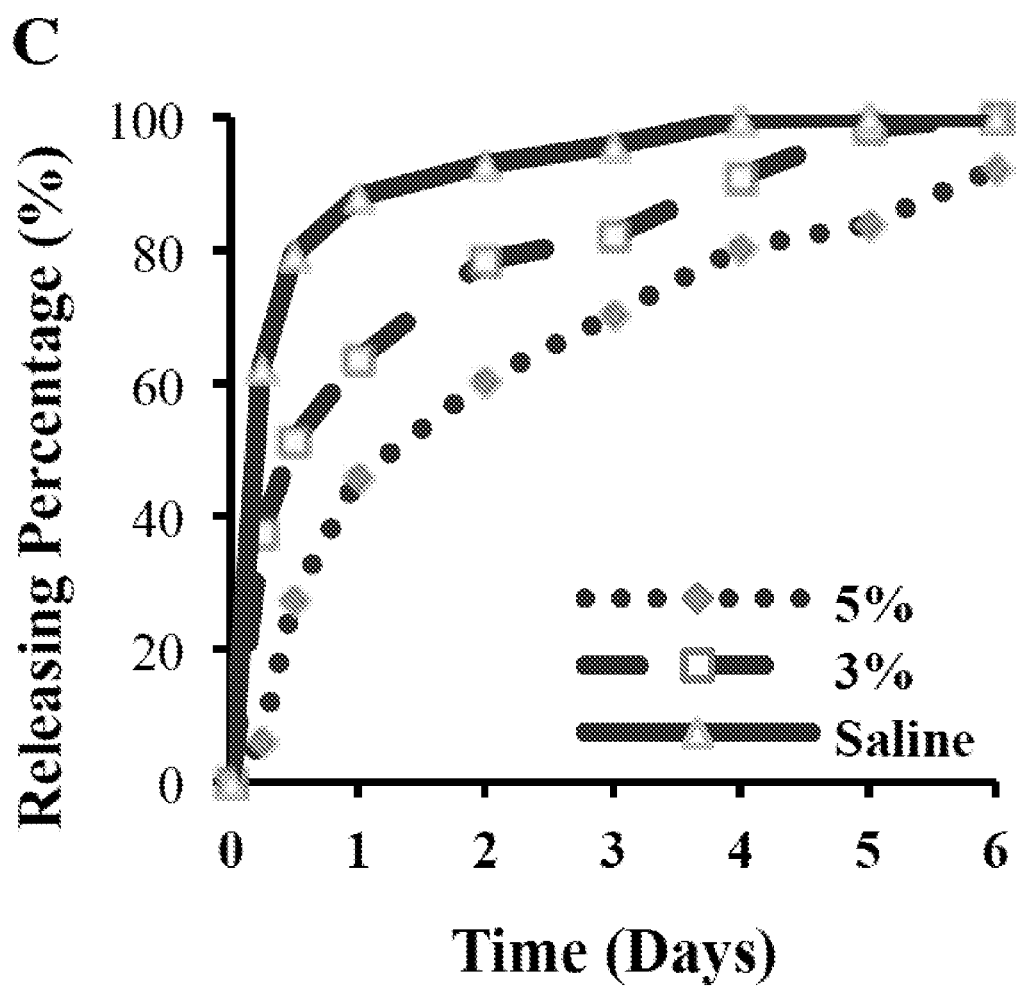
Figure 13:
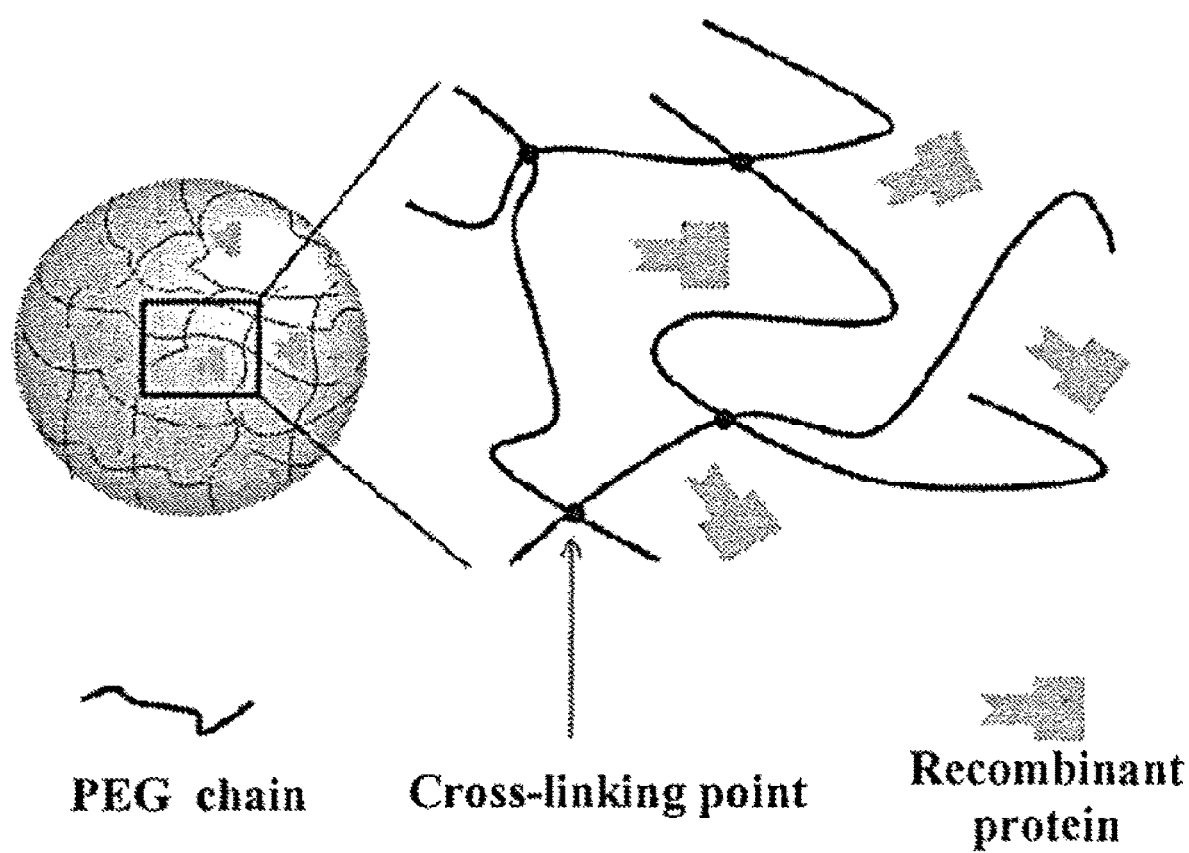
FIG. 13. Schematic illustration of protein-loaded PEG particle.

The main disadvantage of porous scaffold is that surgical procedure or trocar is needed for implantation. To improve the situation, studies have been launched to synthesize water based temperature sensitive hydrogel with protein release properties. The results of this effort have led to the production of polyethylene glycol-poly acrylic acid interpenetrating network (PEG-PAA-IPN) hydrogel. Polyethylene nanoparticles using a precipitation polymerization method were first synthesized. See Tong Cai, M. M., and Zhibing Hu, *Monodisperse Thermoresponsive Microgels of Poly(ethylene glycol) Analogue-Based Biopolymers*. Langmuir, 2007. 23(17): p. 8663-8666. The PEG nanoparticles were then used as seeds to form a secondary polyacrylic acid (PAA) network. At room temperature, PEG-PAA-IPN can be easily blended with a variety of chemokines and drugs. As the temperature increases following subcutaneous injection into the body the PEG-PAA nanoparticles swell to form a solid and porous implant (FIG. 11A). The release of NIR-labeled bovine serum albumin (BSA) from hydrogels containing 0, 3, vs. 5% nanoparticles was also monitored. As expected, PEG-PAA-IPN substantially prolonged the release of NIR-BSA (FIG. 11B). The duration of BSA release depends on polymer weight percentages (FIG. 11C). Similar controlled release properties were also found using other proteins, such as insulin, and EPO. Our results support the idea that PEG-PAA-IPN hydrogel can be easily made to release of a variety of proteins in controlled fashion.

Example 5

Fabrication of Microbubble Scaffolds

Chemokine/growth factor loaded PLGA scaffolds were fabricated using our protein microbubble fabrication method. Briefly, 2-20% w/v protein solution with various chemokines was overlaid with nitrogen gas and sonicated using a probe sonicator (Ultrasonix, Bothell, Wash.) at 20 kHz for 10 seconds. Protein solution can be composed of single proteins or protein mixtures in different ratios. The potential protein candidates including albumin, collagen, gelatin, immunoglobulins, extracellular matrix proteins, fibronectin, etc. Protein microbubble solutions can be added to PLGA (3-15% w/v in 1,4 dioxane) in a 1:1 ratio and gently agitated. They were then quenched in liquid nitrogen and lyophilized for 72 hours at 0.01-0.1 mBar vacuum in a Freezone 12 lyophilizer (Labconco, Kansas City, Mo., USA).

The microbubble (MB) scaffolds were analyzed using Scanning Electron Microscopy. Without the presence of any porogen, control phase separated scaffolds only possessed 20 μm pores (FIG. 12A). However, gelatin MB scaffolds showed the presence of large pores ranging 10-200 μm (FIG. 12B). Protein distribution and internal architecture of the scaffolds was determined by staining histological sections with Coomassie Blue as described earlier. As expected, without the presence of porogen, scaffold section does not retain Coomassie Blue dye (FIG. 12C). In contrast, Coomassie Blue staining of the gelatin MB scaffold sections indicated the presence of protein around the pores and throughout the matrix of the gelatin MB scaffolds (FIG. 12C). The compressive strength of the scaffolds was tested using an MTS Insight 2 machine fitted with a 500 N load cell. Samples (5 mm width and 5 mm thickness) were compressed to 10% strain at a deflection rate of 2 mm/min. The Young's modulus was calculated from the slope of the curve similar to our earlier publication. Despite of pore size difference, there was no difference in porosity between gelatin MB scaffolds and controls and the fabrication technique did not indicate towards a significant compromise on the compressive strength of the gelatin MB scaffolds (FIG. 12G). Finally, the release kinetics of cytokines/growth factors from MB scaffolds was determined using Oyster 800-conjugated EPO and Oyster 800-conjugated SDF. Interestingly, it was found that there was a bolus release (20%) of both chemokines within the first 24 hours. The scaffolds then had a sustained release of both chemokines for approximately 2% of total amounts per day (FIG. 12H).

Example 6

Hydrogel Cancer Cell Traps on Prostate Cancer Cell Recruitment

Figure 17:
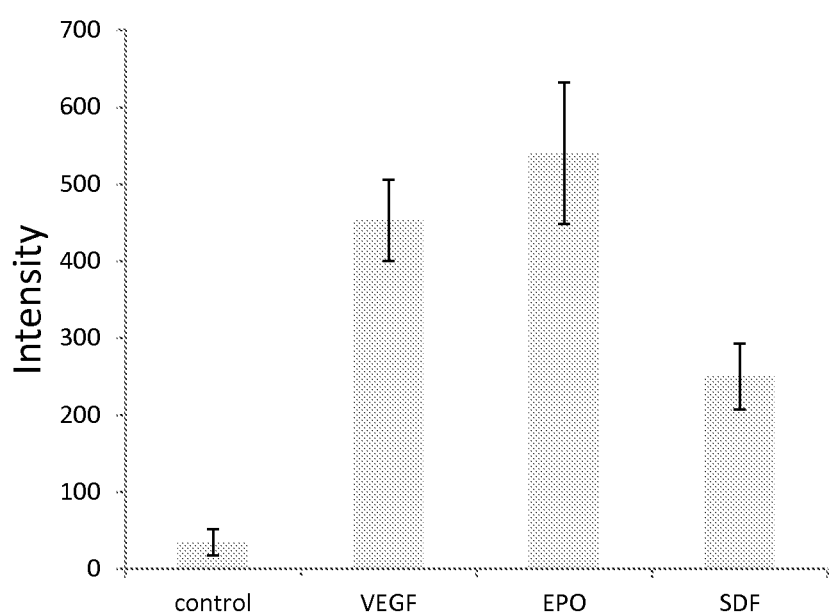
FIG. 17. Effect of localized release of VEGF, EPO or SDF-1α on PC3 Prostate Cancer cell recruitment. Following transplantation for 24 hours, the distribution of near infrared dye-labeled cells was then monitored using whole-body imaging system. PC3 cells were recruited to the implantation site of hydrogel cancer trap releasing various chemokines (VEGF, EPO and SDF-1α). The implant-associated fluorescence intensities were then quantified using by ImageJ software. (n=3).

Using near-infrared labeled PC3 prostate cell transplanted mice, the effect of hydrogel cancer cell traps in reducing cancer metastasis was studied. Specifically, PEG hydrogel was fabricated as following. Carboxyl-terminal PEG derivative polymer was synthesized using free radical polymerization. In brief, 4,4'-azobis(4-cyanovaleric acid) and various weight ratios (10:1-20:1) of 2-(2-Methoxyethoxy)ethyl methacrylate ($MEO_2MA$) and oligo(ethylene glycol)monomethyl ether methacrylates ($M_w$:475;OEOMA475) were dissolved in ethanol to form a 20 wt % monomer solution. The solution was purged with nitrogen gas for 10 min and incubated at 60° C. for 6 h. The solvent was then removed with evaporation under vacuum and the crude polymers are re-dissolved in DI water and were purified with exhaust dialysis against DI water and then lyophilized. The low critical solution temperature (LCST) of the carboxyl-terminal PEG derivative polymers was determined using an UV-vis spectrometer. By changing the molar ratios of $MEO_2MA$ to OEOMA475, the carboxyl-terminal PEG derivative polymer with LCST of 32° C. was achieved and the polymer used to fabricate thermogelling bioactive hydrogel scaffold as described below. Incorporation of chemokines/cytokines to PEG hydrogel was achieved by physical adsorption. PEG hydrogel was mixed with vascular endothelial growth factor (VEGF) (100 ng/ml), erythropoietin (EPO) (100 international unit/ml), stromal derived factor-1α (SDF-1α) or saline (as control). The hydrogel samples were then injected into the subcutaneous cavity (under the skin) of C57 mice via 20 gauge needles. The mice were then transplanted intravenously with PC3 prostate cancer cells ($5 \times 10^6$/mouse). After transplantation for 24 hours, large numbers of PC3 cells were found to accumulate at the hydrogel implant sites as reflected by the increase of fluorescence intensities. Our results show that the localized release of VEGF, EPO or SDF-1α increased the recruitment of PC3 prostate cancer cells to the implant sites (cancer cell traps). See FIG. 17.

Example 7

Hyaluronic Acid Particles' Protein Release Rate

Different sizes of hyaluronic acid (HA) particles (2, 10, 20 and 40 μm in diameter) were fabricated according to our published procedures (U.S. Pat. No. 7,601,704; Zou L, Nair A, Weng H, Tsai Y T, Hu Z, Tang L. Intraocular pressure changes: an important determinant of the biocompatibility of intravitreous implants. *PLoS One.* 2011; 6(12):e28720. PMCID: 3237488). The particles were produced as described as following. Acetone were added to a 0.5 wt % HA solution in a weight ratio of 100:80 (acetone:HA solution) and the mixture were stirred for 2 hours. Adipic acid dihydrazide (ADH) and EDAC (molar ratio of ADH to EDAC: 1:1) were added to the mixture in a weight ratio of 0.05:100 (ADH:HA) to form a crosslinked mixture. This mixture was then stirred at 20° C. for approximately 24 hours, and then the extra acetone in a weight ratio of approximately 160:100 (acetone: HA solution) were added to form the final mixture. The final mixture was stirred for 20 hours and dialyzed against distilled water to form HA particles. By changing HA concentration while keeping acetone/water weight ratio range from 2.5 to 3.8, HA particles with different size can then be made. By changing weight ratio of ADH to HA (0.01/100 to 0.20/100), a series of HA particles with varying cross-linking densities were then prepared.

To maximize the loading efficiency of various cancer cell chemokines, a "breathing-in" method was employed for the encapsulation of various macromolecules within HA particles (Blackburn W H, Dickerson E B, Smith M H, McDonald J F, Lyon L A. Peptide-functionalized nanogels for targeted siRNA delivery. *Bioconjugate chemistry.* 2009; 20(5):960-8. PMCID: 2765502). In brief, lyophilized HA particles were re-suspended in solutions containing the vascular endothelial growth factor (VEGF) (100 ng/ml), erythropoietin (EPO) (100 international unit/ml), stromal derived factor-1α (SDF-1α). Importantly, this was done using a loading solution volume that is almost completely imbibed by the swelling particles.

Figure 18:
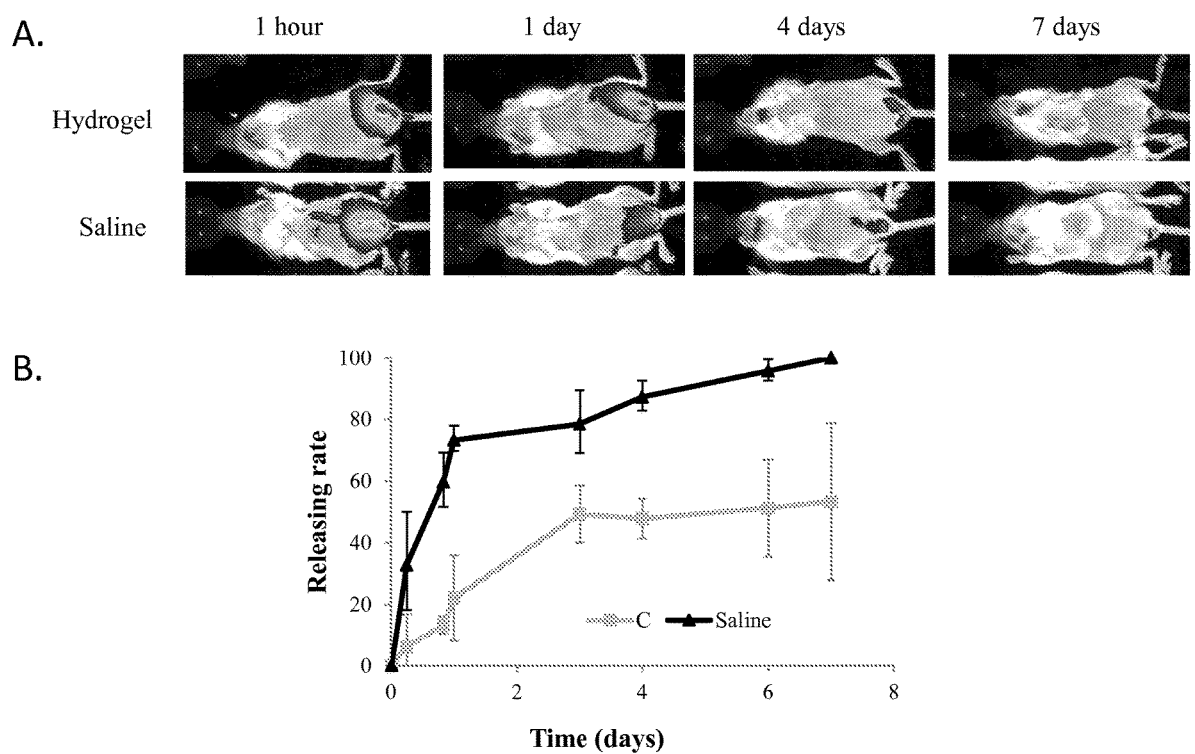
FIG. 18. (A) Representative images of BSA-NIR fluorescence intensities at the HA particle injection sites at different time. (B) The release kinetics of NIR dye-labeled BSA release from HA particles (labeled as "C") or saline (NIR dye+saline) at different time points.

Studies have been carried out to test whether HA particles can be used for subcutaneous protein delivery. Briefly, BSA-labeled with near-infrared (NIR) dye (Oyster®-800, Boca Scientific) following manufacture instruction was first synthesized. BSA-NIR was injected in the subcutaneous space (under the skin) of Balb/C mice with control (BSA-NIR) or BSA-NIR-loaded HA particles. The release of BSA-NIR was then monitored daily using Kodak In Vivo FX Pro system (f/stop, 2.5; excitation filter: 760 nm; emission filter: 830 nm: 4×4 binning) For imaging analyses, regions of interest were drawn over the injection sites in the fluorescence images, and the mean intensities for all pixels in the fluorescence imaging were calculated. It was found that the encapsulation of BSA into HA particles substantially prolonged the release rates of NIR-labeled BSA (Example #2) to >14 days. See FIGS. 18A-B.

Example 8

Cancer Cell Trap for Metastatic Cancer Treatment and Diagnosis

Cancer cell traps are implants designed to trigger the recruitment of metastatic cancer cells. Such device can be used for both cancer diagnosis and cancer treatment.

Figure 19:
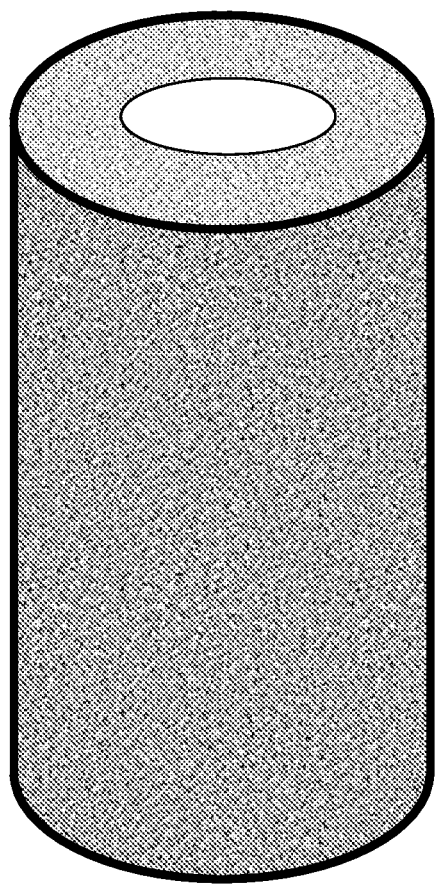
FIG. 19. Embodiment of a cancer cell trap for use as a diagnostic to detect metastatic cancer cells.

The recruited cancer cells can be extracted from cancer cell traps for diagnosis purpose. For that, cancer cell traps may be fabricated as a tubular structure with opening on one or both sides of the implants. See FIG. 19. The porous structure allows the infiltration of cancer cells from the sides and the opening to the inner lumen of the cancer cell trap. The cancer cells containing tissue fluid can then be recovered from the inner lumen of the cancer cell traps via a 18-23 gauge needles. The types of the recruited cells can then be determined using flow cytometry method.

Figure 20:
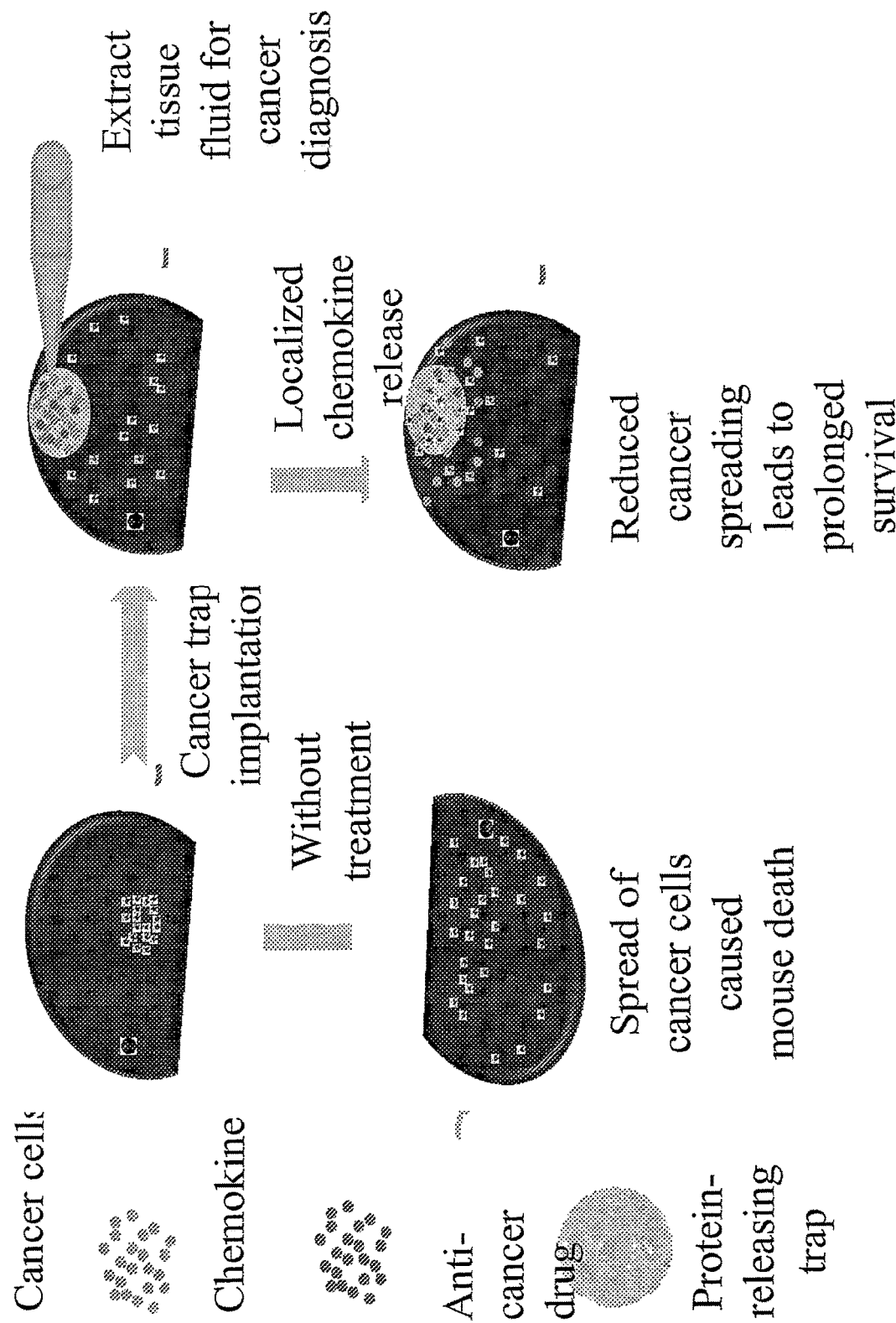
FIG. 20. Flowchart model depicting metastatic cancer diagnosis and treatment.

For cancer treatment purpose, cancer cell traps can be made to release anti-cancer drugs. Cancer cell traps can also be exposed to localization radiation. These methods will allow the recruited cancer cells to be eradicated at the implant sites. See FIG. 20.

Example 9

Cancer Cell Trap Design

| Cancer cell trap | Materials | Physical Property | Delivery Methods |
|---|---|---|---|
| Solid Implants | Polymers of water soluble polymers, including, but not limited to, dextran, derivatives of poly-methacrylamide, PEG, maleic acid, malic acid, and maleic acid anhydride and may | Tubular shape, disk shape | Injection via trocar, implantation via surgical procedure |

| Cancer cell trap | Materials | Physical Property | Delivery Methods |
|---|---|---|---|
| Particles | include these polymers and a suitable coupling agent, including 1-ethyl-3 (3-dimethylaminopropyl)- | Microparticles and nanoparticles | Injection via 19-23 gauge needles |
| Solution | carbodiimide, also referred to as carbodiimide. Polymers may be degradable or nondegradable or of a polyelectrolyte material. Degradable polymer materials include poly-L-glycolic acid (PLGA), poly-DL-glycolic, poly-L-lactic acid (PLLA), PLLA-PLGA copolymers, poly(DL-lactide)-block-methoxy polyethylene glycol, polycaprolacton, poly(caprolacton)-block-methoxy polyethylene glycol (PCL-MePEG), poly(DL-lactide-co-caprolactone)-block-methoxy polyethylene glycol (PDLLACL-MePEG), some polysaccharide (e.g., hyaluronic acid, polyglycan, chitoson), proteins (e.g., fibrinogen, albumin, collagen, extracellular matrix), peptides (e.g., RGD, polyhistidine), nucleic acids (e.g., RNA, DNA, single or double stranded), viruses, bacteria, cells and cell fragments, organic or carbon-containing materials, as examples. Nondegradable materials include natural or synthetic polymeric materials (e.g., polystyrene, polypropylene, polyethylene teraphthalate, polyether urethane, polyvinyl chloride, silica, polydimethyl siloxane, acrylates, arcylamides, poly (vinylpyridine), polyacroleine, polyglutaraldehyde), some polysaccharides (e.g., hydroxypropyl cellulose, cellulose derivatives, dextran ®, dextrose, sucrose, ficoll ®, percoll ®, arabinogalactan, starch), and hydrogels (e.g., polyethylene glycol, ethylene vinyl acetate, N-isopropylacrylamide, polyamine, polyethyleneimine, poly-aluminum chloride). | Hydrogel (solution with high viscosity or becoming solidified in body temperature) | Injection via 19-23 gauge needles |

Example 10

Chemokine Concentrations and Duration

The Experiments have been carried out to determine the release rates of various cancer stem cell chemokines/growth factors from cancer cell traps. The optimal release rates for each biomolecules are listed below.

| Biomolecules | Injection quantity | Release rates | Duration |
|---|---|---|---|
| Erythropoietin (EPO) | 600 international units/0.027 milliliter cancer trap gel or 1 cubic centimeters scaffold traps/kg body weight | 1.5-2.5 international units/1 milliliter of hydrogel/particle cancer traps or 1 cubic centimeters scaffold traps/days | >30 days |
| RANTES/CCL5 | 600 ng/1 ml cancer trap gel or 1 cubic centimeters scaffold traps/kg body weight | 10 ng/1 milliliter of hydrogel/particle cancer traps or 1 cubic centimeters scaffold traps/day | >21 days |
| Hepatocyte growth factor (HGF/SF) | 900 ng/1 ml cancer trap gel or 1 cubic centimeters scaffold traps/kg body weight | 15 ng/1 milliliter of hydrogel/particle cancer traps or 1 cubic centimeters scaffold traps/day | >28 days |

| Biomolecules | Injection quantity | Release rates | Duration |
|---|---|---|---|
| Stromal derived factor-1α (SDF-1α) | 10 μg/1 ml cancer trap gel or 1 cubic centimeters scaffold traps/kg body weight | 100 ng/1 milliliter of hydrogel/particle cancer traps or 1 cubic centimeters scaffold traps/day | >24 days |

Cancer cell trap size and dimension for human patients. All studies carried out thus far used mice cancer models. Since the cancer cells are recruited based on the chemokines gradient, localized concentrations, but not the systemic concentrations, are the determining factors. In other words, the effectiveness of the cancer cell traps are determined on the localized release rates as listed in the above table.

Example 11

Cancer Cell Trap Implantation Sites

Figure 21:
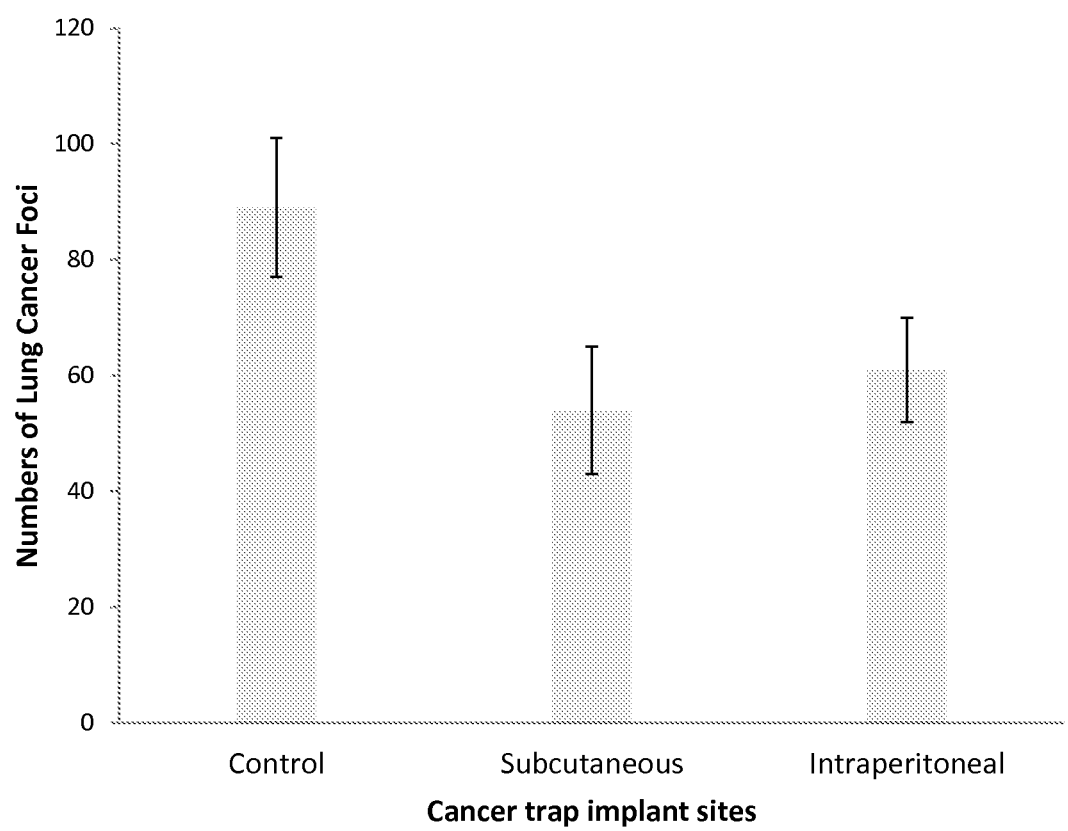
FIG. 21. The numbers of cancer foci were quantified on the lung of Lewis Lung Carcinoma cell transplanted animals without (control) or with hydrogel cancer cell traps implanted in either subcutaneous or intraperitoneal space.

Cancer cell traps can be implanted in the subcutaneous space and intraperitoneal cavities. The animal experiments were carried out using C57BL/6 mice (6-10 week old) from Jackson Laboratory (Bar Harbor, Me., USA). This murine cancer metastasis model is composed of two consecutive steps. First, Lewis Lung Carcinoma (LLC) cancer cells ($5 \times 10^5$ cells/0.2 ml/mouse) were transplanted into the animals via intravenous injection. Second, EPO-loaded nanoparticle cancer cell traps (600 international units/1 ml) were injected into the subcutaneous space or intraperitoneal space. After implantation of cancer cell traps for 4 weeks, the numbers of metastasis cancer foci in the lung were then quantified. It is found that the implantation of cancer cell traps in both of subcutaneous space (under the skin) and the intraperitoneal space (inside the peritoneal cavities) are both effective in reducing LLC cancer cell foci formation in the lung. See FIG. 21.

The fabrication of temperature sensitive hydrogel nanoparticles is described in the recent publication (Cai T, Hu P, Sun M, Zhou J, Tsai Y-T, Baker D W, Tang L. Novel thermogelling dispersions of polymer nanoparticles for controlled protein release. *Nanomedicine* 8 (8): 1301-8, 2012). Poly(oligo(ethylene glycol)) nanoparticles were prepared using a precipitation polymerization method. Specifically, 6.3 g OEGEEM, 0.86 g MEO$_4$MA, along with 0.02 g of ethylene glycol dimethacrylate (EGDMA) as a crosslinking agent, 0.08 g sodium dodecyl sulfate (SDS), and 0.61 g methacrylol-l-lysine were added into 400 g of distilled water in a three-neck flask, the flask was placed in a circulating bath of water at 70° C. under nitrogen gas for 30 minutes. 0.20 g of ammonium persulfate (APS) was dissolved in 5 g water and added to the solution to initiate polymerization. The reactions were carried out at 70° C. for 6 hours under N$_2$ gas. The resultant poly(oligo(ethylene glycol) nanoparticles were purified with dialysis against DI water for one week. The above-prepared nanoparticles were then used as seeds to form a second network based on polyacrylic acid (PAAc). 252 g of the Poly(oligo(ethylene glycol) nanoparticle solution were mixed with 0.3 g N,N-methylenebisacrylamide (BIS) and 3.0 g acrylic acid in a flask at 23° C. for 24 hours. 0.2 g TEMED and 0.2 g of ammonium persulfate (APS) were each then dissolved in 5 g of water and then added into the flask. The reaction was carried out in the nitrogen environment for 30 mins. The resultant nanoparticles were purified by dialyzing against DI water for one week and centrifuged for further use.

Example 12

Effectiveness of Cancer Cell Traps on Reducing Circulating Cancer Cells

Figure 22:
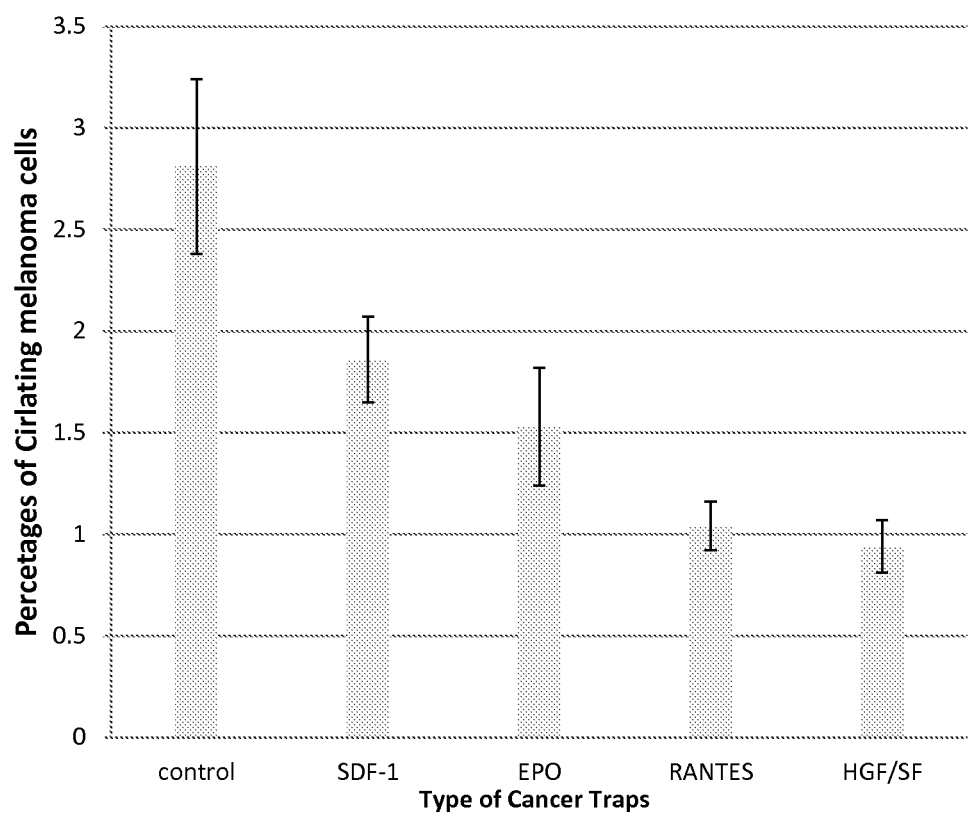
FIG. 22. Percentages of circulating melanoma cells were found in the peripheral blood from animals implanted with cancer cell traps released different cancer cell chemokines/growth factors.
Figure 23:
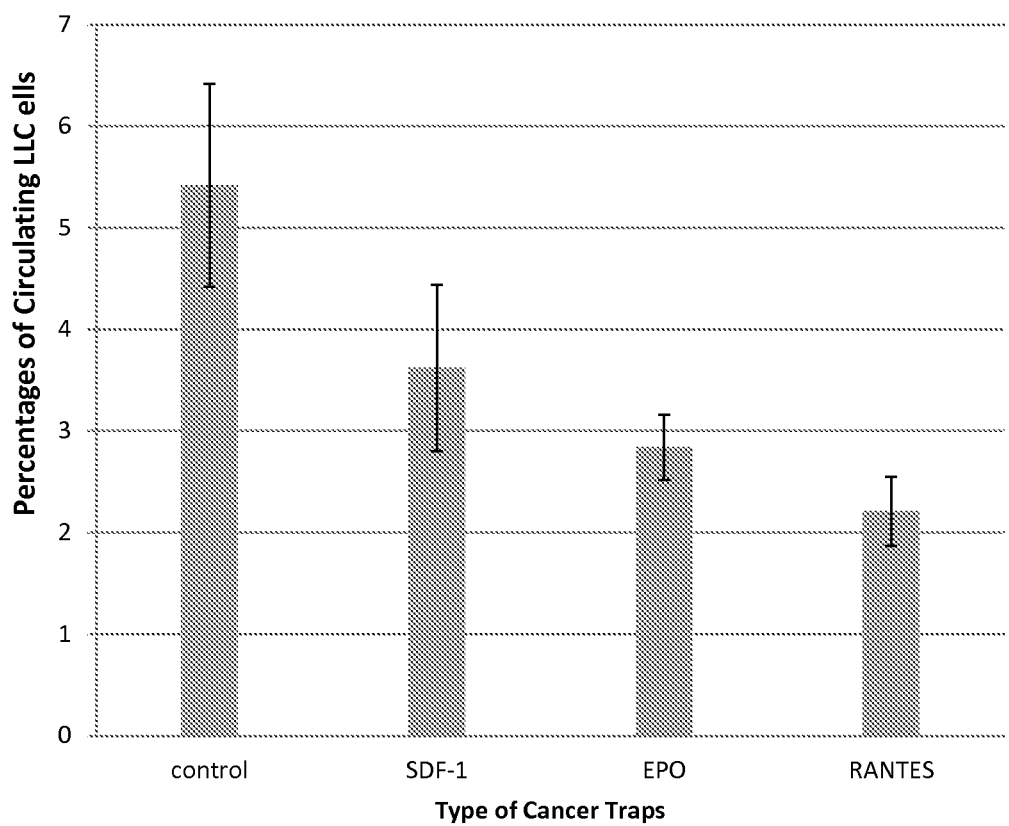
FIG. 23. Percentages of circulating Lewis Lung Carcinoma cancer cells were found in the peripheral blood from animals implanted with cancer cell traps released different cancer cell chemokines/growth factors.

The effectiveness of hydrogel cancer cell traps on reducing or eliminating circulating cancer cells were tested. The animal experiments were carried out using C57BL/6 mice (6-10 week old) from Jackson Laboratory (Bar Harbor, Me., USA). Near-infrared dye labeled B16F 10 melanoma cancer cells or LLC cancer cells ($5 \times 10^6$ cells/0.2 ml/mouse) were transplanted into the animals via intravenous injection. PEG hydrogel loaded with various chemokines/growth factors (EPO, 600 international units/1 ml; SDF-1α 10 μg/1 ml, RANTES/CCL5—600 ng/ml, or HGF/SF—900 ng/ml) were injected into the subcutaneous space on the back of the animals. After cancer cell transplantation for 24 hours, blood was drawn from each animals and the percentages of cancer cells among total number of white blood cells were then quantified using flow cytometry methods. It was found that various cancer cell traps were able to reduce the number of cancer cells in the circulation. See FIGS. 22 and 23.

Example 13

Chemokine Concentrations and Duration

Figure 24:
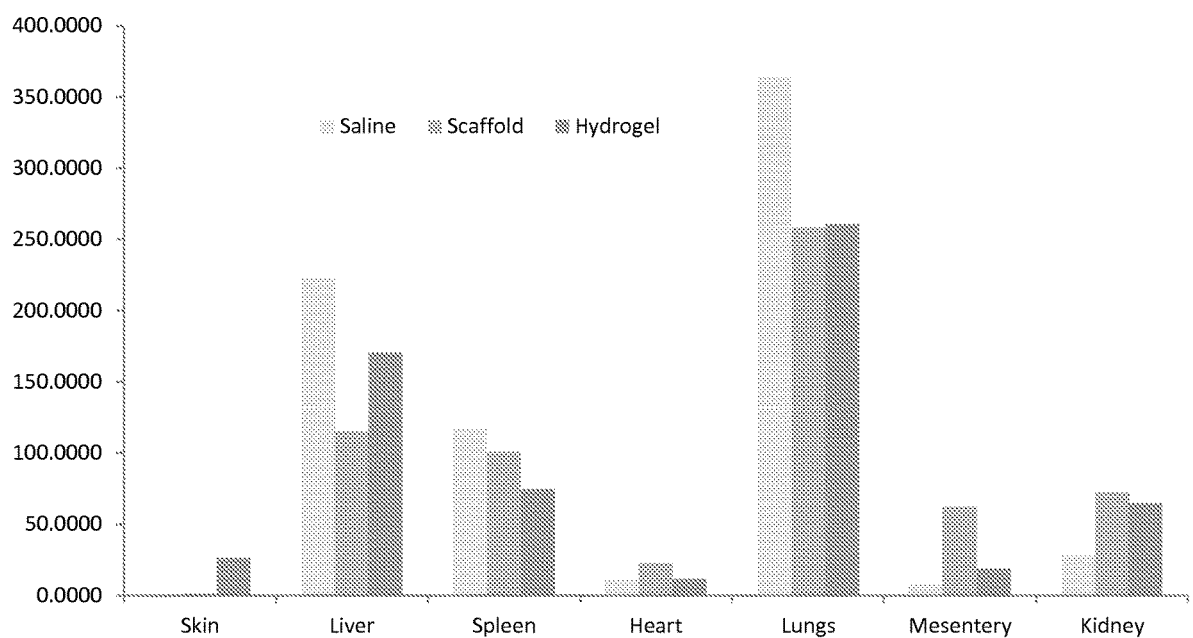
FIG. 24. Comparison of biodistribution of LLC cells in various organs isolated from animals bearing hydrogel cancer cell traps, scaffold cancer cell traps, or nothing (as controls).

Further studies were carried out to determine whether the implantation of cancer cell traps can reduce cancer cell spreading—metastasis. To find the answer, C57 mice were transplanted with near-infrared dye-labeled LLC cancer cells ($5 \times 10^6$ cells/0.2 ml/mouse) were transplanted into the animals via intravenous injection. EPO-loaded PEG hydrogel (600 international units/1 ml; labeled as hydrogel) and EPO loaded PLA scaffold (600 international units/1 ml; labeled as scaffolds) were injected or implanted into the subcutaneous space on the back of the animals, respectively. After cancer cell transplantation for 24 hours, all organs were isolated from the animals and the distribution of LLC cells in various organs was determined using Kodak In-Vivo Imaging Systems. Indeed, it was found that the implantation of hydrogel cancer cell traps and scaffold cancer cell traps substantially reduce the numbers of recruited cancer cells in the liver, spleen and lungs which are the main organs for LLC metastasis. See FIG. 24.

Example 14

Localized Release of Chemotherapy Drugs on Cancer Eradication.

The fabrication of temperature sensitive hydrogel nanoparticles is described in the recent publication (Cai T, Hu P, Sun M, Zhou J, Tsai Y-T, Baker D W, Tang L. Novel thermogelling dispersions of polymer nanoparticles for controlled protein release. *Nanomedicine* 8 (8): 1301-8, 2012). The nanoparticles were loaded with EPO (600 international units/1 ml) in the presence or absence of doxorubicine (300 μg/m1) and paclitaxel (30 mg/ml). For that, EPO (600 international units), doxorubicine (300 μg) or paclitaxel (30 mg) was mixed with 50 μg of hydrogel nanoparticles at room temperature. After implantation, the average in vivo release rates for doxorubicin and paclitaxel were measured at 10 μg/day and 1 mg/day, respectively.

Further studies were carried out to determine whether the implantation of chemotherapy drug-loaded cancer cell traps can kill cancer cells at the implant sites. To find the answer, C57 mice were transplanted with fluorescein isothiocyanate (FITC)-labeled LLC cancer cells ($5\times10^6$ cells/0.2 ml/mouse) or FITC-labeled melanoma cells via intravenous injection. After implantation for different periods of time (1, 2, 4, and 7 days), animals were sacrificed. Implants and surrounding tissues were isolated and then sectioned for histological analyses. To quantify cell recruitment, tissue section images were taken using a Leica fluorescence microscope (Leica Microsystems Wetzlar GmbH, Wetzlar, Germany) equipped with a QImaging Retiga-EXi CCD camera (QImaging, Surrey, BC, Canada). The tissue section images at a magnification of 400× (viewing area 0.24 mm$^2$) were then used to quantify the cell numbers per view field by cell counter plugin of ImageJ processing program.

Figure 25:
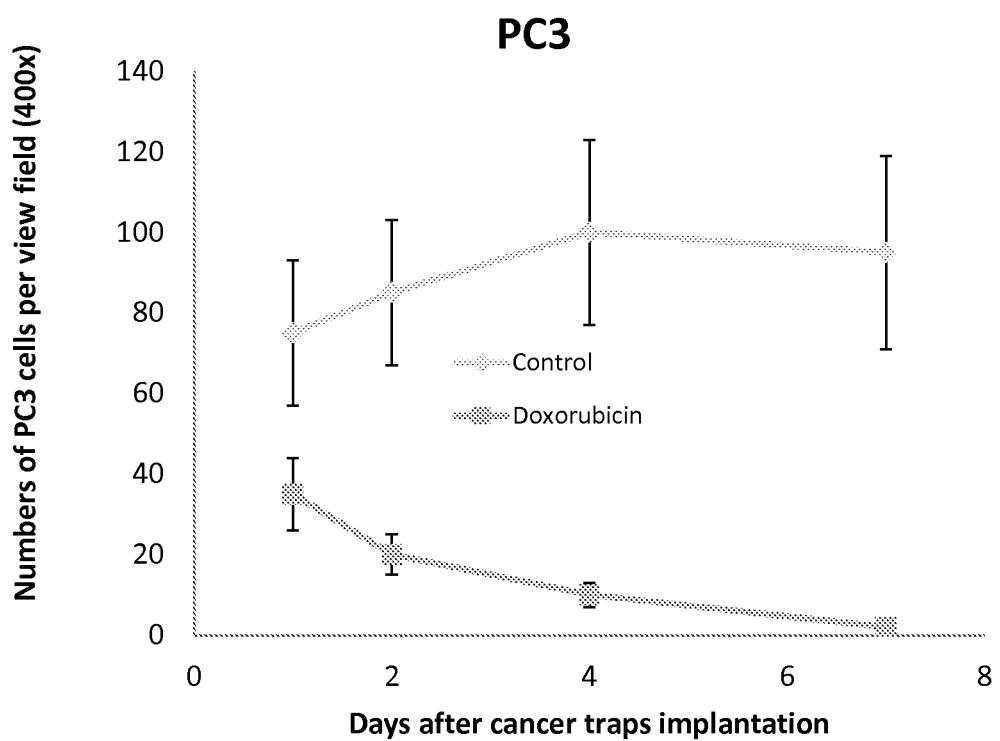
FIG. 25. Quantification of FITC-labeled PC3 prostate cancer cells recruited to the EPO-loaded particles vs. EPO+doxorubicin (300 µg/1 ml/implant)-loaded particles after implantation for different periods of time.
Figure 26:
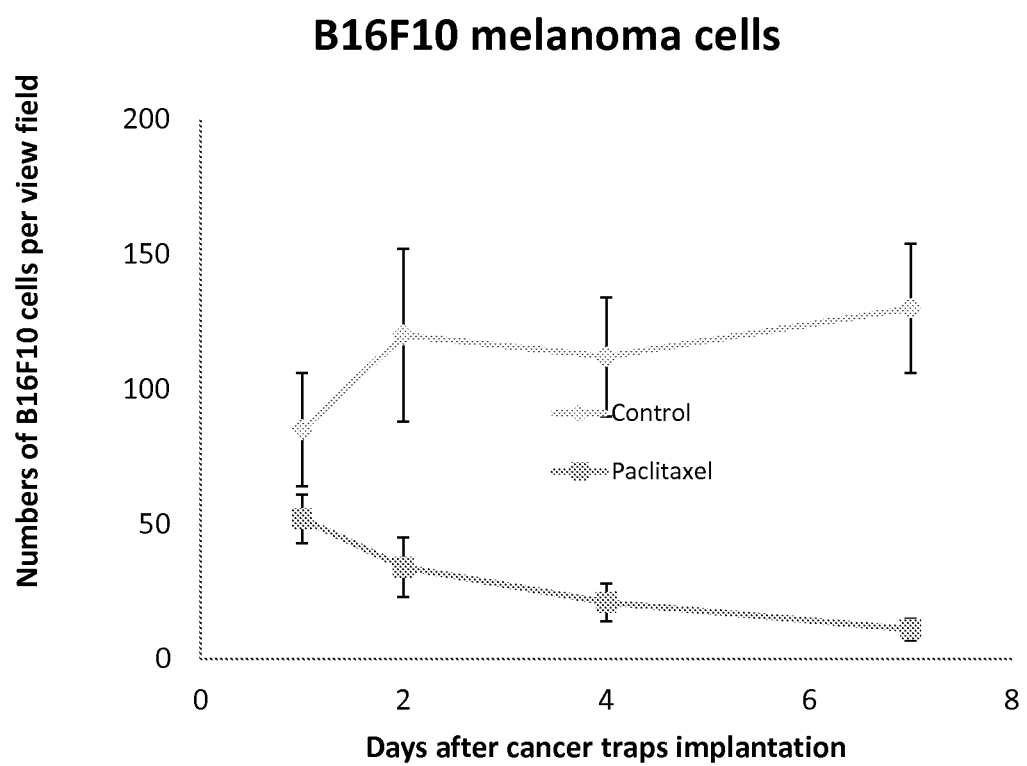
FIG. 26. Quantification of FITC-labeled B16F10 melanoma cancer cells recruited to the EPO-loaded particles vs. EPO+Paclitaxel (30 mg/ml/implant)-loaded particles after implantation for different periods of time.
Figure 27A:
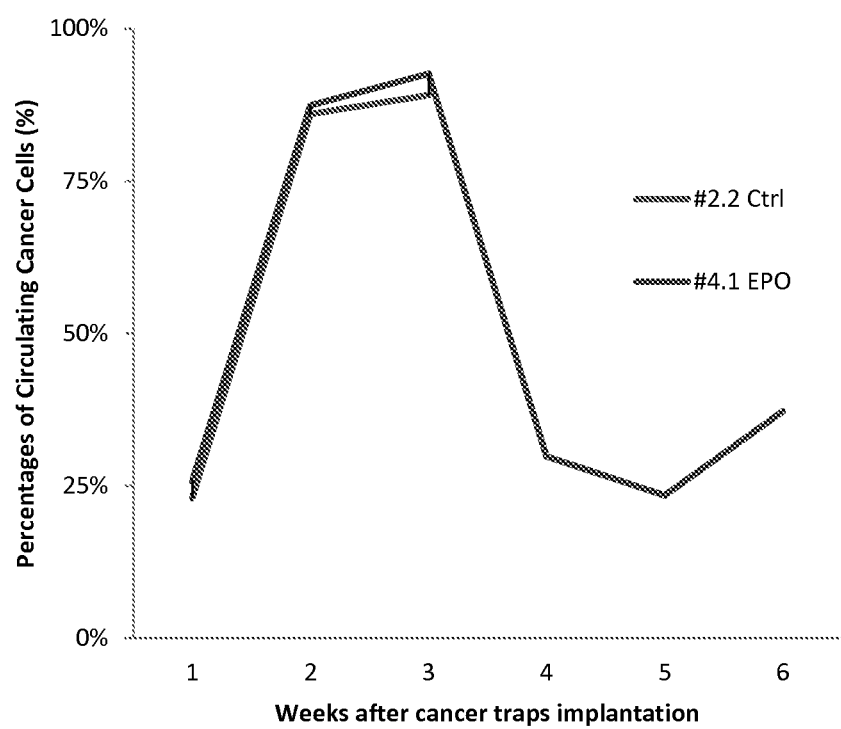
FIG. 27. Quantification of circulating AML cells following cancer cell traps implantation. Cancer cell traps were fabricated using EPO-loaded poly-glycolic acid scaffolds. Blank PLGA scaffolds were used as controls. Three pairs of animals (a single pair of animals in each of panels A-C is shown) were tested. All three sets of data showed that EPO-loaded cancer cell traps not only reduce the percentages of circulating cancer cells but also prolonged the life span of cancer-bearing animals.
Figure 27B:
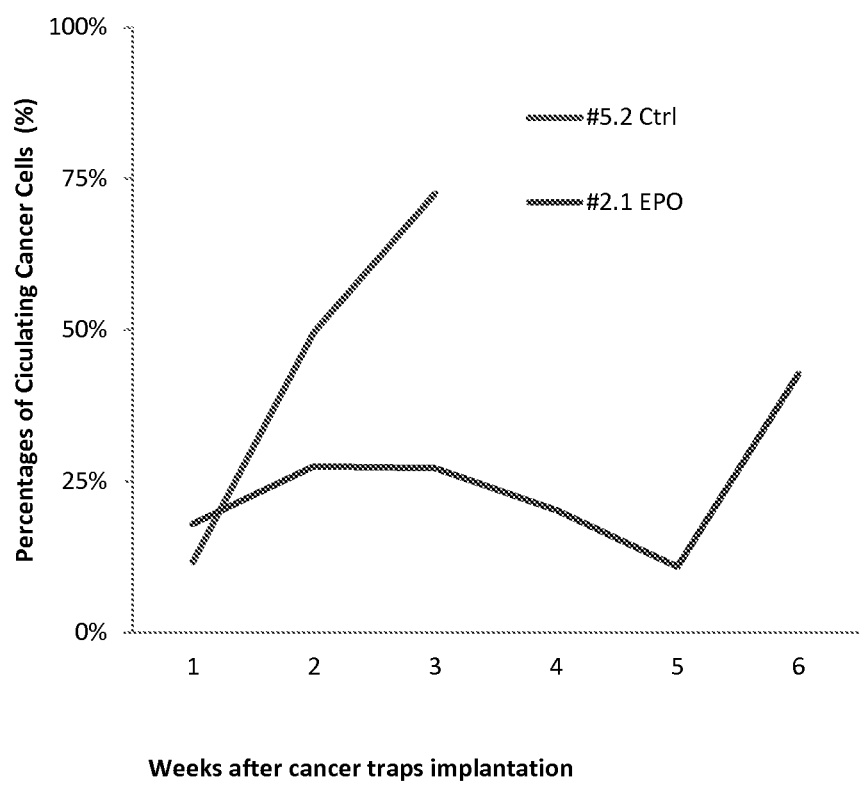
Figure 27C:
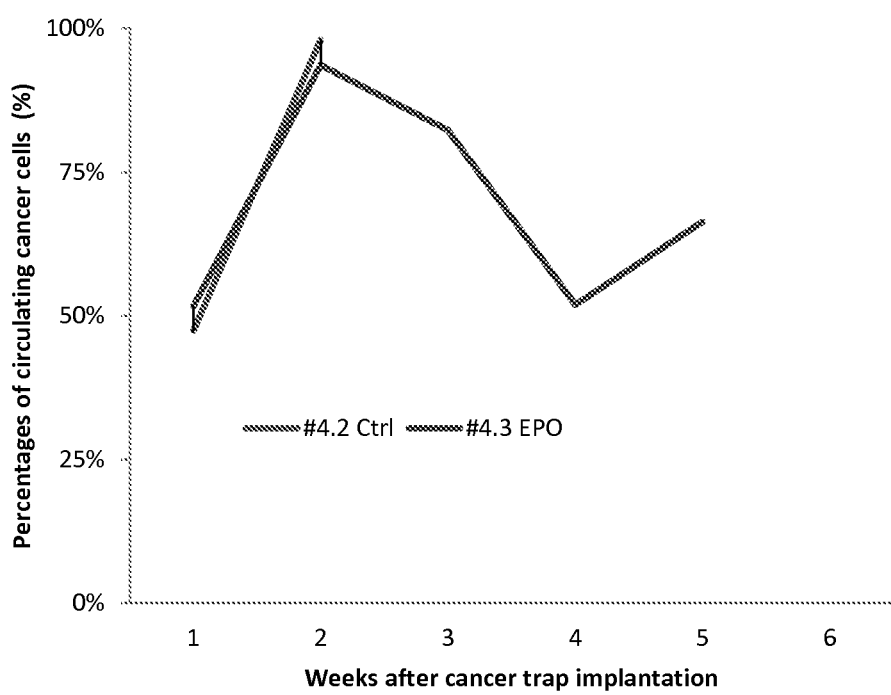
Figure 28A:
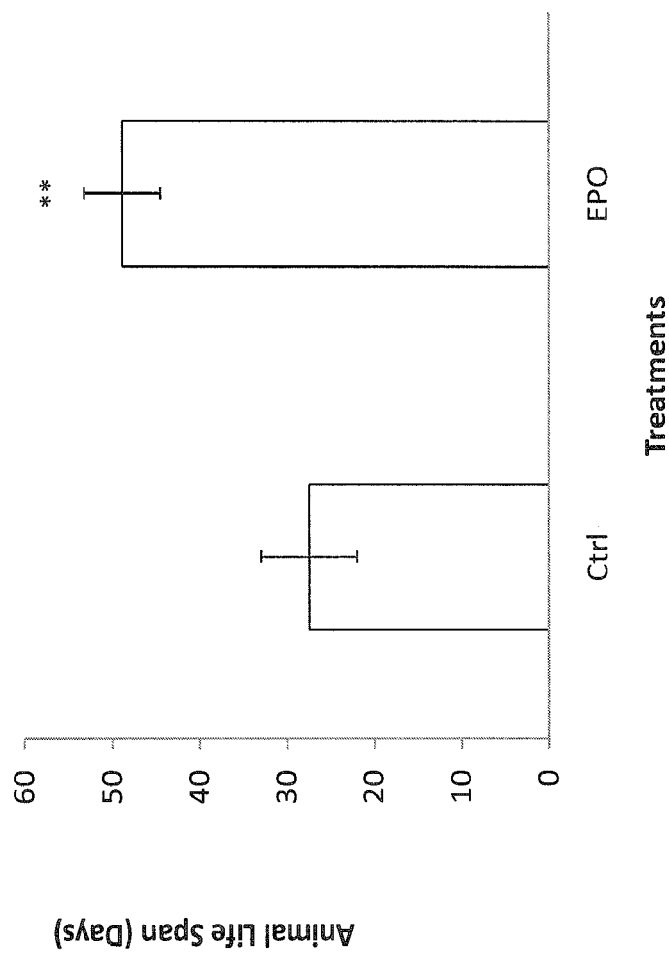
FIG. 28. The effectiveness of EPO-loaded cancer cell traps on prolonged the life span of AML model. The life span of the animals with or without cancer cell traps was determined based on either "days after trap implantation" (A) or "days after cancer cell transplantation" (B). Both sets of data show the substantial improvement of life span of animals following cancer cell trap implantation. The cancer cell trap implantation also improves the overall survival of cancer bearing mice (C).
Figure 28B:
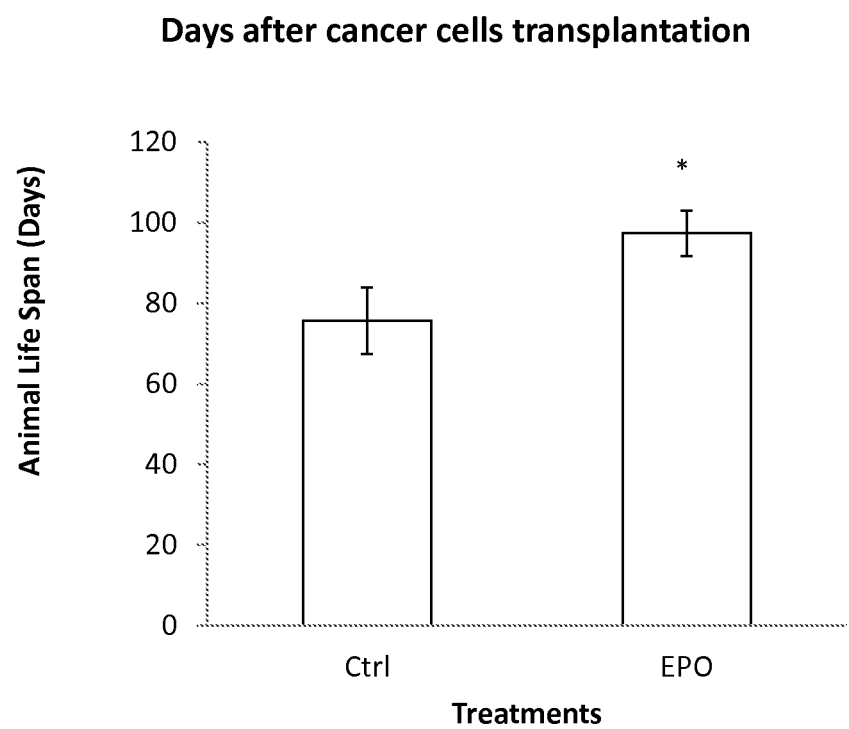
Figure 28C:
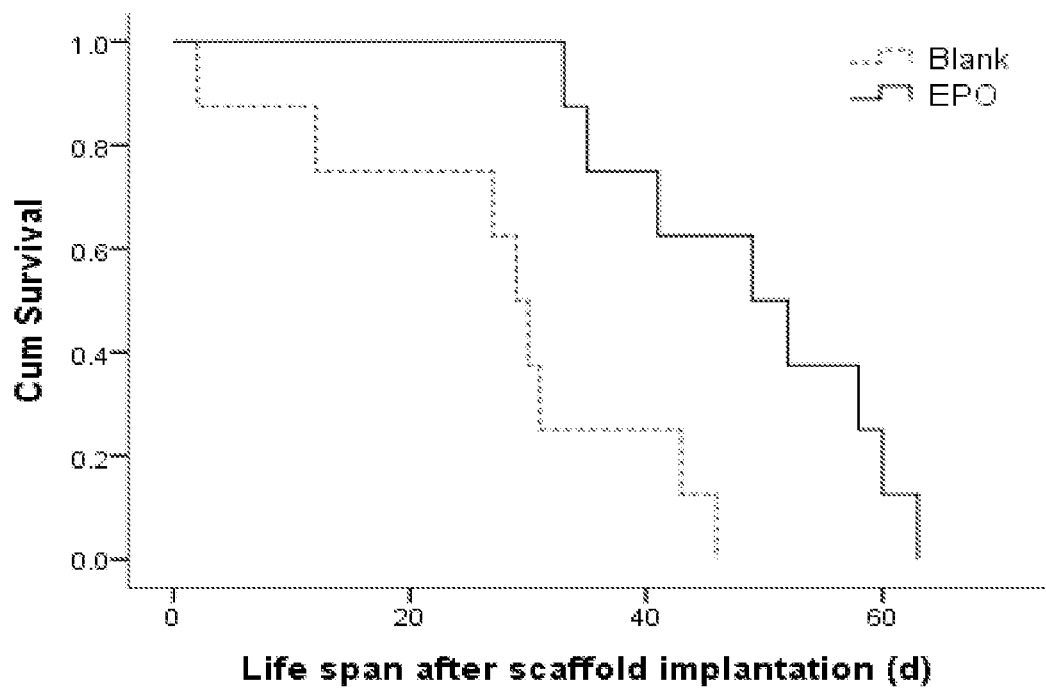

As anticipated, the supplement of chemotherapy drugs (doxorubicin and paclitaxel) substantially reduced the numbers of recruited PC3 cells and melanoma cells. These results support that the cancer cell traps can be used to eradicate (>95% in 7 days) circulating cancer cells at the implant sites. See FIGS. 25 and 26.

Example 15

Localized Chemotherapy Drugs

AE9 AML (acute myeloblastic leukemia) model was established by transplantation of $0.5\times10^5$ AE9 cells with $0.8\times10^5$ competitor cells in C57BL/6 mice after irradiation at 1 Gy. The animals were then kept in the cages until that the peripheral blood AML cells were detected >10% by flow cytometry. The mice were randomly paired and implanted with EPO-PLGA scaffold or blank PLGA scaffold. Cell numbers and life span after scaffold implantation was monitored. See FIGS. 27A-C and 28A-C.

Figure 29:
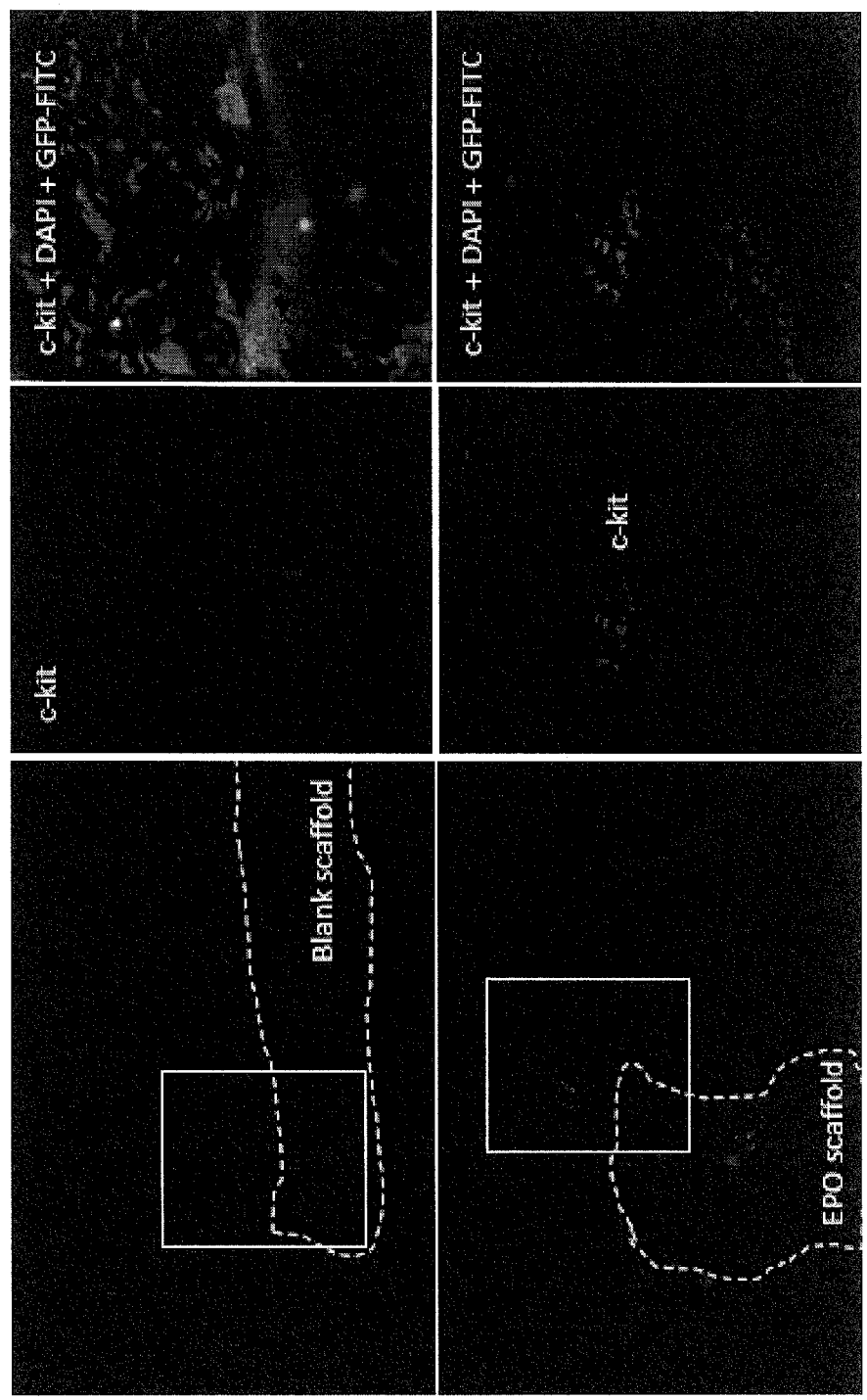
FIG. 29. Histology of cancer stem cells around scaffold implants.

Cancer cell traps were found recruit not only cancer cells but also cancer stem cells. It was discovered that many of the recruited AML cells possess a stem cell marker. These results support that cancer cell traps may substantially weaken cancer metastasis by specifically removing cancer stem cells from the circulation. C-kit staining and GFP+ shown in FIG. 29 includes cancer stain cells.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

The invention claimed is:

1. A method for treating cancer metastasis comprising administering to a subject in need thereof an effective amount of a cancer cell trap, wherein the cancer cell trap comprises
   i. microparticles;
   ii. nanoparticles;
   iii. a scaffold structure; or
   iv. a hydrogel,
wherein circulating cancer cells are recruited to the cancer cell trap;
   wherein the circulating cancer cells are selected from the group consisting of leukemia cells, melanoma cells, prostate cancer cells, and lung cancer cells,
   wherein the cancer cell trap comprises erythropoietin (EPO) that is released from the cancer cell trap, wherein the EPO enables recruitment and accumulation of circulating cancer cells in the cancer cell trap, and
   wherein the cancer cell trap further comprises a chemotherapeutic agent and/or the method further comprises subjecting the cancer cell trap to radiation.

2. The method of claim 1, wherein the scaffold structure comprises a degradable polymer and polypeptides.

3. The method of claim 1, wherein the cancer cell trap comprises PLGA, albumin, collagen, gelatin, immunoglobulins, extracellular matrix proteins, fibronectin and combinations thereof.

4. The method of claim 1, wherein the cancer cell trap is implanted into the subject.

5. The method of claim 1, wherein the cancer cell trap is injected into the subject.

6. The method of claim 1, wherein the subject is a human.

7. The method of claim 1, wherein the chemotherapeutic agent is a member selected from the group consisting of cytotoxic agents, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial, exotoxic agents, and combinations thereof.

* * * * *